(12) United States Patent
Sun

(10) Patent No.: US 6,680,379 B1
(45) Date of Patent: Jan. 20, 2004

(54) ORGANIC ANION TRANSPORTER GENES AND PROTEINS

(75) Inventor: William Sun, San Diego, CA (US)

(73) Assignee: Metabasis Therapeutics, Inc., San Diego, CA (US)

(*) Notice: Subject to any disclaimer, the term of this patent is extended or adjusted under 35 U.S.C. 154(b) by 0 days.

(21) Appl. No.: 09/614,891

(22) Filed: Jul. 12, 2000

Related U.S. Application Data

(60) Provisional application No. 60/143,771, filed on Jul. 12, 1999.

(51) Int. Cl.[7] .................. C07H 21/00; C07K 14/00; C12N 15/00; C12N 5/00

(52) U.S. Cl. .................. 536/23.2; 536/23.1; 536/24.3; 435/69.1; 435/320.1; 435/325; 530/350

(58) Field of Search .................. 435/69.1, 325, 435/91.2, 320.1; 530/350; 536/23.1, 23.2, 24.3

(56) References Cited

U.S. PATENT DOCUMENTS 5,972,702 A * 10/1999 Beier et al. .................. 435/325
6,432,631 B1    8/2002 Cihlar

OTHER PUBLICATIONS

Smith et al. The challenges of genome sequence annotation of "The devil is in the details". Nature Biotechnology 15:1222–1223 (1997).*
Bork. Powers and Pitfalls in Sequence Analysis: The 70% Hurdle. Genome Research 10:398–400 (2000).*
Brenner. Errors in genome annotation, Trends in Genetics 15:132–133 (1999).*
Bowie et al. Deciphering the Message in Protein Sequences: Tolerance to Amino Acid Substitutions. Science 247:1306–1310 (1990).*

* cited by examiner

*Primary Examiner*—Yvonne Eyler
*Assistant Examiner*—Regina M. DeBerry
(74) *Attorney, Agent, or Firm*—Paul, Hastings, Janofsky & Walker, LLP

(57) ABSTRACT

This invention relates to novel human organic anion transporter polypeptides and genes encoding such polypeptides. The invention is directed towards the isolation, characterization and use of human organic anion transporter polypeptides for pharmacological screening of substrates, analogues of substrates, and modulators of human organic anion proteins. This invention also provides cell cultures, which stably contain nucleic acid sequences encoding human organic anion transport polypeptides. Such cell lines are useful for screening compounds in vitro to identify and characterize modulators, inhibitors and substrates of human organic anion transporter polypeptides.

20 Claims, 31 Drawing Sheets

```
     CTGAGCTGACCTGACCCCCAAAGTGAAGGAGAAGCTGCAAGGGAAAAGGGAGGGACAGAT
  1  ---------+---------+---------+---------+---------+---------+  60
     GACTCGACTGGACTGGGGGTTTCACTTCCTCTTCGACGTTCCCTTTTCCCTCCCTGTCTA

CAGGGAGACCGGGGAAGAAGGAGGAGCAGCCAAGGAGGCTGCTGTCCCCCCACAGAGCAG
 61  ---------+---------+---------+---------+---------+---------+ 120
     GTCCCTCTGGCCCCTTCTTCCTCCTCGTCGGTTCCTCCGACGACAGGGGGGTGTCTCGTC

CTCGGACTCAGCTCCCGGAGCAACCCAGCTGCGGAGGCAACGGCAGTGCTGCTCCTCCAG
121  ---------+---------+---------+---------+---------+---------+ 180
     GAGCCTGAGTCGAGGGCCTCGTTGGGTCGACGCCTCCGTTGCCGTCACGACGAGGAGGTC

CGAAGGACAGCAGGCAGGCAGACAGACAGAGGTCCTGGGACTGGAAGGCCTCAGCCCCCA
181  ---------+---------+---------+---------+---------+---------+ 240
     GCTTCCTGTCGTCCGTCCGTCTGTCTGTCTCCAGGACCCTGACCTTCCGGAGTCGGGGGT

GCCACTGGGCTGGGCCTGGCCCAATGGCCTTTAATGACCTCCTGCAGCAGGTGGGGGGTG
241  ---------+---------+---------+---------+---------+---------+ 300
     CGGTGACCCGACCCGGACCGGGTTACCGGAAATTACTGGAGGACGTCGTCCACCCCCCAC

M  A  F  N  D  L  L  Q  Q  V  G  G  V -
     TCGGCCGCTTCCAGCAGATCCAGGTCACCCTGGTGGTCCTCCCCCTGCTCCTGATGGCTT
301  ---------+---------+---------+---------+---------+---------+ 360
     AGCCGGCGAAGGTCGTCTAGGTCCAGTGGGACCACCAGGAGGGGGACGAGGACTACCGAA

G  R  F  Q  Q  I  Q  V  T  L  V  V  L  P  L  L  L  M  A  S -
     CTCACAACACCCTGCAGAACTTCACTGCTGCCATCCCTACCCACCACTGCCGCCCGCCTG
361  ---------+---------+---------+---------+---------+---------+ 420
     GAGTGTTGTGGGACGTCTTGAAGTGACGACGGTAGGGATGGGTGGTGACGGCGGGCGGAC

H  N  T  L  Q  N  F  T  A  A  I  P  T  H  H  C  R  P  P  A -
     CCGATGCCAACCTCAGCAAGAACGGGGGGCTGGAGGTCTGGCTGCCCCGGGACAGGCAGG
421  ---------+---------+---------+---------+---------+---------+ 480
     GGCTACGGTTGGAGTCGTTCTTGCCCCCCGACCTCCAGACCGACGGGGCCCTGTCCGTCC

D  A  N  L  S  K  N  G  G  L  E  V  W  L  P  R  D  R  Q  G -
     GGCAGCCTGAGTCCTGCCTCCGCTTCACCTCCCCGCAGTGGGGACTGCCCTTTCTCAATG
481  ---------+---------+---------+---------+---------+---------+ 540
     CCGTCGGACTCAGGACGGAGGCGAAGTGGAGGGGCGTCACCCCTGACGGGAAAGAGTTAC

Q  P  E  S  C  L  R  F  T  S  P  Q  W  G  L  P  F  L  N  G -
     GCACAGAAGCCAATGGCACAGGGGCCACAGAGCCCTGCACCGATGGCTGGATCTATGACA
541  ---------+---------+---------+---------+---------+---------+ 600
     CGTGTCTTCGGTTACCGTGTCCCCGGTGTCTCGGGACGTGGCTACCGACCTAGATACTGT

T  E  A  N  G  T  G  A  T  E  P  C  T  D  G  W  I  Y  D  N -
     ACAGCACCTTCCCATCTACCATCGTGACTGAGTGGGACCTTGTGTGCTCTCACAGGGCCC
601  ---------+---------+---------+---------+---------+---------+ 660
```

FIG. 1A

```
                    TGTCGTGGAAGGGTAGATGGTAGCACTGACTCACCCTGGAACACACGAGAGTGTCCCGGG

S  T  F  P  S  T  I  V  T  E  W  D  L  V  C  S  H  R  A  L  -

TACGCCAGCTGGCCCAGTCCTTGTACATGGTGGGGGTGCTGCTCGGAGCCATGGTGTTCG
              661   ---------+---------+---------+---------+---------+---------+   720
                    ATGCGGTCGACCGGGTCAGGAACATGTACCACCCCCACGACGAGCCTCGGTACCACAAGC

R  Q  L  A  Q  S  L  Y  M  V  G  V  L  L  G  A  M  V  F  G  -

GCTACCTTGCAGACAGGCTAGGCCGCCGGAAGGTACTCATCTTGAACTACCTGCAGACAG
              721   ---------+---------+---------+---------+---------+---------+   780
                    CGATGGAACGTCTGTCCGATCCGGCGGCCTTCCATGAGTAGAACTTGATGGACGTCTGTC

Y  L  A  D  R  L  G  R  R  K  V  L  I  L  N  Y  L  Q  T  A  -

CTGTGTCAGGGACCTGCGCAGCCTTCGCACCCAACTTCCCCATCTACTGCGCCTTCCGGC
              781   ---------+---------+---------+---------+---------+---------+   840
                    GACACAGTCCCTGGACGCGTCGGAAGCGTGGGTTGAAGGGGTAGATGACGCGGAAGGCCG

V  S  G  T  C  A  A  F  A  P  N  F  P  I  Y  C  A  F  R  L  -

TCCTCTCGGGCATGGCTCTGGCTGGCATCTCCCTCAACTGCATGACACTGAATGTGGAGT
              841   ---------+---------+---------+---------+---------+---------+   900
                    AGGAGAGCCCGTACCGAGACCGACCGTAGAGGGAGTTGACGTACTGTGACTTACACCTCA

L  S  G  M  A  L  A  G  I  S  L  N  C  M  T  L  N  V  E  W  -

GGATGCCCATTCACACACGGGCCTGCGTGGGCACCTTGATTGGCTATGTCTACAGCCTGG
              901   ---------+---------+---------+---------+---------+---------+   960
                    CCTACGGGTAAGTGTGTGCCCGGACGCACCCGTGGAACTAACCGATACAGATGTCGGACC

M  P  I  H  T  R  A  C  V  G  T  L  I  G  Y  V  Y  S  L  G  -

GCCAGTTCCTCCTGGCTGGTGTGGCCTACGCTGTGCCCCACTGGCGCCACCTGCAGCTAC
              961   ---------+---------+---------+---------+---------+---------+   1020
                    CGGTCAAGGAGGACCGACCACACCGGATGCGACACGGGGTGACCGCGGTGGACGTCGATG

Q  F  L  L  A  G  V  A  Y  A  V  P  H  W  R  H  L  Q  L  L  -

TGGTCTCTGCGCCTTTTTTTGCCTTCTTCATCTACTCCTGGTTCTTCATTGAGTCGGCCC
              1021  ---------+---------+---------+---------+---------+---------+   1080
                    ACCAGAGACGCGGAAAAAAACGGAAGAAGTAGATGAGGACCAAGAAGTAACTCAGCCGGG

V  S  A  P  F  F  A  F  F  I  Y  S  W  F  F  I  E  S  A  R  -

GCTGGCACTCCTCCTCCGGGAGGCTGGACCTCACCCTGAGGGCCCTGCAGAGAGTCGCCC
              1081  ---------+---------+---------+---------+---------+---------+   1140
                    CGACCGTGAGGAGGAGGCCCTCCGACCTGGAGTGGGACTCCCGGGACGTCTCTCAGCGGG

W  H  S  S  S  G  R  L  D  L  T  L  R  A  L  Q  R  V  A  R  -

GGATCAATGGGAAGCGGGAAGAAGGAGCCAAATTGAGTATGGAGGTACTCCGGGCCAGTC
              1141  ---------+---------+---------+---------+---------+---------+   1200
```

*FIG. 1B*

```
                CCTAGTTACCCTTCGCCCTTCTTCCTCGGTTTAACTCATACCTCCATGAGGCCCGGTCAG

I  N  G  K  R  E  E  G  A  K  L  S  M  E  V  L  R  A  S  L -

TGCAGAAGGAGCTGACCATGGGCAAAGGCCAGGCATCGGCCATGGAGCTGCTGCGCTGCC
       1201    ---------+---------+---------+---------+---------+---------+     1260
                ACGTCTTCCTCGACTGGTACCCGTTTCCGGTCCGTAGCCGGTACCTCGACGACGCGACGG

Q  K  E  L  T  M  G  K  G  Q  A  S  A  M  E  L  L  R  C  P -

CCACCCTCCGCCACCTCTTCCTCTGCCTCTCCATGCTGTGGTTTGCCACTAGCTTTGCAT
       1261    ---------+---------+---------+---------+---------+---------+     1320
                GGTGGGAGGCGGTGGAGAAGGAGACGGAGAGGTACGACACCAAACGGTGATCGAAACGTA

T  L  R  H  L  F  L  C  L  S  M  L  W  F  A  T  S  F  A  Y -

ACTATGGGCTGGTCATGGACCTGCAGGGCTTTGGAGTCAGCATCTACCTAATCCAGGTGA
       1321    ---------+---------+---------+---------+---------+---------+     1380
                TGATACCCGACCAGTACCTGGACGTCCCGAAACCTCAGTCGTAGATGGATTAGGTCCACT

Y  G  L  V  M  D  L  Q  G  F  G  V  S  I  Y  L  I  Q  V  I -

TCTTTGGTGCTGTGGACCTGCCTGCCAAGCTTGTGGGCTTCCTTGTCATCAACTCCCTGG
       1381    ---------+---------+---------+---------+---------+---------+     1440
                AGAAACCACGACACCTGGACGGACGGTTCGAACACCCGAAGGAACAGTAGTTGAGGGACC

F  G  A  V  D  L  P  A  K  L  V  G  F  L  V  I  N  S  L  G -

GTCGCCGGCCTGCCCAGATGGCTGCACTGCTGCTGGCAGGCATCTGCATCCTGCTCAATG
       1441    ---------+---------+---------+---------+---------+---------+     1500
                CAGCGGCCGGACGGGTCTACCGACGTGACGACGACCGTCCGTAGACGTAGGACGAGTTAC

R  R  P  A  Q  M  A  A  L  L  L  A  G  I  C  I  L  L  N  G -

GGGTGATACCCCAGGACCAGTCCATTGTCCGAACCTCTCTTGCTGTGCTGGGGAAGGGTT
       1501    ---------+---------+---------+---------+---------+---------+     1560
                CCCACTATGGGGTCCTGGTCAGGTAACAGGCTTGGAGAGAACGACACGACCCCTTCCCAA

V  I  P  Q  D  Q  S  I  V  R  T  S  L  A  V  L  G  K  G  C -

GTCTGGCTGCCTCCTTCAACTGCATCTTCCTGTATACTGGGGAACTGTATCCCACAATGA
       1561    ---------+---------+---------+---------+---------+---------+     1620
                CAGACCGACGGAGGAAGTTGACGTAGAAGGACATATGACCCCTTGACATAGGGTGTTACT

L  A  A  S  F  N  C  I  F  L  Y  T  G  E  L  Y  P  T  M  I -

TCCGGCAGACAGGCATGGGAATGGGCAGCACCATGGCCCGAGTGGGCAGCATCGTGAGCC
       1621    ---------+---------+---------+---------+---------+---------+     1680
                AGGCCGTCTGTCCGTACCCTTACCCGTCGTGGTACCGGGCTCACCCGTCGTAGCACTCGG

R  Q  T  G  M  G  M  G  S  T  M  A  R  V  G  S  I  V  S  P -

CACTGGTGAGCATGACTGCCGAGCTCTACCCCTCCATGCCTCTCTTCATCTACGGTGCTG
       1681    ---------+---------+---------+---------+---------+---------+     1740
```

FIG. 1C

```
         GTGACCACTCGTACTGACGGCTCGAGATGGGGAGGTACGGAGAGAAGTAGATGCCACGAC
          L  V  S  M  T  A  E  L  Y  P  S  M  P  L  F  I  Y  G  A  V -

TTCCTGTGGCCGCCAGCGCTGTCACTGTCCTCCTGCCAGAGACCCTGGGCCAGCCACTGC
1741     ---------+---------+---------+---------+---------+---------+     1800
         AAGGACACCGGCGGTCGCGACAGTGACAGGAGGACGGTCTCTGGGACCCGGTCGGTGACG
          P  V  A  A  S  A  V  T  V  L  L  P  E  T  L  G  Q  P  L  P -

CAGACACGGTGCAGGACCTGGAGAGCAGGAAAGGGAAACAGACGCGACAGCAACAAGAGC
1801     ---------+---------+---------+---------+---------+---------+     1860
         GTCTGTGCCACGTCCTGGACCTCTCGTCCTTTCCCTTTGTCTGCGCTGTCGTTGTTCTCG
          D  T  V  Q  D  L  E  S  R  K  G  K  Q  T  R  Q  Q  Q  E  H -

ACCAGAAGTATATGGTCCCACTGCAGGCCTCAGCACAAGAGAAGAATGGACTCTGAGGAC
1861     ---------+---------+---------+---------+---------+---------+     1920
         TGGTCTTCATATACCAGGGTGACGTCCGGAGTCGTGTTCTCTTCTTACCTGAGACTCCTG
          Q  K  Y  M  V  P  L  Q  A  S  A  Q  E  K  N  G  L  *

TGAGAAGGGGCCTTACAGAACCCTAAAGGGAGGGAAGGTCCTACAGGTCTCCGGCCACCC
1921     ---------+---------+---------+---------+---------+---------+     1980
         ACTCTTCCCCGGAATGTCTTGGGATTTCCCTCCCTTCCAGGATGTCCAGAGGCCGGTGGG

ACACAAGGAGGAGGAAGAGGAAATGGTGACCCAAGTGTGGGGGTTGTGGTTCAGGAAAGC
1981     ---------+---------+---------+---------+---------+---------+     2040
         TGTGTTCCTCCTCCTTCTCCTTTACCACTGGGTTCACACCCCCAACACCAAGTCCTTTCG

ATCTTCCCAGGGGTCCACCTCCCTTTATAAACCCCACCAGAACCACATCATTAAAAGGTT
2041     ---------+---------+---------+---------+---------+---------+     2100
         TAGAAGGGTCCCCAGGTGGAGGGAAATATTTGGGGTGGTCTTGGTGTAGTAATTTTCCAA

TGACTGCGCACCAAAAAAAAAAAAAAAA
2101     ---------+---------+-------                                      2127
         ACTGACGCGTGGTTTTTTTTTTTTTTTT
```

FIG. 1D

```
     CTGCACCTGAAGCATTTGGTGGGTGAGCAGCATGGGCTTTGAGGAGCTGCTGGAGCAGGT
  1  ---------+---------+---------+---------+---------+---------+   60
     GACGTGGACTTCGTAAACCACCCACTCGTCGTACCCGAAACTCCTCGACGACCTCGTCCA

M  G  F  E  E  L  L  E  Q  V  -

GGGCGGCTTTGGGCCCTTCCAACTGCGGAATGTGGCACTGCTGGCCCTGCCCCGAGTGCT
 61  ---------+---------+---------+---------+---------+---------+  120
     CCCGCCGAAACCCGGGAAGGTTGACGCCTTACACCGTGACGACCGGGACGGGGCTCACGA

G  G  F  G  P  F  Q  L  R  N  V  A  L  L  A  L  P  R  V  L  -

GCTACCACTGCACTTCCTCCTGCCCATCTTCCTGGCTGCCGTGCCTGCCCACCGATGTGC
121  ---------+---------+---------+---------+---------+---------+  180
     CGATGGTGACGTGAAGGAGGACGGGTAGAAGGACCGACGGCACGGACGGGTGGCTACACG

L  P  L  H  F  L  L  P  I  F  L  A  A  V  P  A  H  R  C  A  -

CCTGCCGGGTGCCCCTGCCAACTTCAGCCATCAGGATGTGTGGCTGGAGGCCCATCTTCC
181  ---------+---------+---------+---------+---------+---------+  240
     GGACGGCCCACGGGGACGGTTGAAGTCGGTAGTCCTACACACCGACCTCCGGGTAGAAGG

L  P  G  A  P  A  N  F  S  H  Q  D  V  W  L  E  A  H  L  P  -

CCGGGAGCCTGATGGCACGCTCAGCTCCTGCCTCCGCTTTGCCTATCCCCAGGCTCTCCC
241  ---------+---------+---------+---------+---------+---------+  300
     GGCCCTCGGACTACCGTGCGAGTCGAGGACGGAGGCGAAACGGATAGGGGTCCGAGAGGG

R  E  P  D  G  T  L  S  S  C  L  R  F  A  Y  P  Q  A  L  P  -

CAACACCACGTTGGGGGAAGAAAGGCAGAGCCGTGGGGAGCTGGAGGATGAACCTGCCAC
301  ---------+---------+---------+---------+---------+---------+  360
     GTTGTGGTGCAACCCCCTTCTTTCCGTCTCGGCACCCCTCGACCTCCTACTTGGACGGTG

N  T  T  L  G  E  E  R  Q  S  R  G  E  L  E  D  E  P  A  T  -

AGTGCCCTGCTCTCAGGGCTGGGAGTACGACCACTCAGAATTCTCCTCTACCATTGCAAC
361  ---------+---------+---------+---------+---------+---------+  420
     TCACGGGACGAGAGTCCCGACCCTCATGCTGGTGAGTCTTAAGAGGAGATGGTAACGTTG

V  P  C  S  Q  G  W  E  Y  D  H  S  E  F  S  S  T  I  A  T  -

TGAGTGGGATCTGGTGTGTGAGCAGAAAGGTCTGAACAGAGCTGCGTCCACTTTCTTCTT
421  ---------+---------+---------+---------+---------+---------+  480
     ACTCACCCTAGACCACACACTCGTCTTTCCAGACTTGTCTCGACGCAGGTGAAAGAAGAA

E  W  D  L  V  C  E  Q  K  G  L  N  R  A  A  S  T  F  F  F  -

CGCCGGTGTGCTGGTGGGGGCTGTGGCCTTTGGATATCTGTCCGACAGGTTTGGGCGGCG
481  ---------+---------+---------+---------+---------+---------+  540
     GCGGCCACACGACCACCCCCGACACCGGAAACCTATAGACAGGCTGTCCAAACCCGCCGC

```
     GCGTCTGCTGCTGGTAGCCTACGTGAGTACCCTGGTGCTGGGCCTGGCATCTGCAGCCTC
541  ---------+---------+---------+---------+---------+---------+  600
     CGCAGACGACGACCATCGGATGCACTCATGGGACCACGACCCGGACCGTAGACGTCGGAG

R  L  L  L  V  A  Y  V  S  T  L  V  L  G  L  A  S  A  A  S -

CGTCAGCTATGTAATGTTTGCCATCACCCGCACCCTTACTGGCTCAGCCCTGGCTGGTTT
601  ---------+---------+---------+---------+---------+---------+  660
     GCAGTCGATACATTACAAACGGTAGTGGGCGTGGGAATGACCGAGTCGGGACCGACCAAA

V  S  Y  V  M  F  A  I  T  R  T  L  T  G  S  A  L  A  G  F -

TACCATCATCGTGATGCCACTGGAGCTGGAGTGGCTGGATGTGGAGCACCGCACCGTGGC
661  ---------+---------+---------+---------+---------+---------+  720
     ATGGTAGTAGCACTACGGTGACCTCGACCTCACCGACCTACACCTCGTGGCGTGGCACCG

T  I  I  V  M  P  L  E  L  E  W  L  D  V  E  H  R  T  V  A -

TGGAGTCCTGAGCAGCACCTTCTGGACAGGGGGCGTGATGCTGCTGGCACTGGTTGGGTA
721  ---------+---------+---------+---------+---------+---------+  780
     ACCTCAGGACTCGTCGTGGAAGACCTGTCCCCCGCACTACGACGACCGTGACCAACCCAT

G  V  L  S  S  T  F  W  T  G  G  V  M  L  L  A  L  V  G  Y -

CCTGATACGGGACTGGCGATGGCTTCTGCTAGCTGTCACCCTGCCTTGTGCCCCAAGCAT
781  ---------+---------+---------+---------+---------+---------+  840
     GGACTATGCCCTGACCGCTACCGAAGACGATCGACAGTGGGACGGAACACGGGGTTCGTA

L  I  R  D  W  R  W  L  L  L  A  V  T  L  P  C  A  P  S  I -

CCTCAGCCTCTGGTGGGTGCCTGAGTCTGCACGCTGGCTTCTGACCCAAGGCCATGTGAA
841  ---------+---------+---------+---------+---------+---------+  900
     GGAGTCGGAGACCACCCACGGACTCAGACGTGCGACCGAAGACTGGGTTCCGGTACACTT

L  S  L  W  W  V  P  E  S  A  R  W  L  L  T  Q  G  H  V  K -

AGAGGCCCACAGGTACTTGCTCCACTGTGCCAGGCTCAATGGGCGGCCAGTGTGTGAGGA
901  ---------+---------+---------+---------+---------+---------+  960
     TCTCCGGGTGTCCATGAACGAGGTGACACGGTCCGAGTTACCCGCCGGTCACACACTCCT

E  A  H  R  Y  L  L  H  C  A  R  L  N  G  R  P  V  C  E  D -

CAGCTTCAGCCAGGAGGCTGTGAGCAAAGTGGCCGCCGGGGAACGGGTGGTCCGAAGACC
961  ---------+---------+---------+---------+---------+---------+  1020
     GTCGAAGTCGGTCCTCCGACACTCGTTTCACCGGCGGCCCCTTGCCCACCAGGCTTCTGG

S  F  S  Q  E  A  V  S  K  V  A  A  G  E  R  V  V  R  R  P -

TTCATACCTAGACCTGTTCCGCACACCACGGCTCCGACACATCTCACTGTGCTGCGTGGT
1021 ---------+---------+---------+---------+---------+---------+  1080
     AAGTATGGATCTGGACAAGGCGTGTGGTGCCGAGGCTGTGTAGAGTGACACGACGCACCA

```
     GGTGTGGTTCGGAGTGAACTTCTCCTATTACGGCCTGAGTCTGGATGTGTCGGGGCTGGG
1081 ---------+---------+---------+---------+---------+---------+ 1140
     CCACACCAAGCCTCACTTGAAGAGGATAATGCCGGACTCAGACCTACACAGCCCCGACCC

V  W  F  G  V  N  F  S  Y  Y  G  L  S  L  D  V  S  G  L  G  -

GCTGAACGTGTACCAGACACAGCTGTTGTTCGGGGCTGTGGAACTGCCCTCCAAGCTGCT
1141 ---------+---------+---------+---------+---------+---------+ 1200
     CGACTTGCACATGGTCTGTGTCGACAACAAGCCCCGACACCTTGACGGGAGGTTCGACGA

L  N  V  Y  Q  T  Q  L  L  F  G  A  V  E  L  P  S  K  L  L  -

GGTCTACTTGTCGGTGCGCTACGCAGGACGCCGCCTCACGCAAGCCGGGACACTGCTGGG
1201 ---------+---------+---------+---------+---------+---------+ 1260
     CCAGATGAACAGCCACGCGATGCGTCCTGCGGCGGAGTGCGTTCGGCCCTGTGACGACCC

V  Y  L  S  V  R  Y  A  G  R  R  L  T  Q  A  G  T  L  L  G  -

CACGGCCCTGGCGTTCGGCACTAGACTGCTAGTGTCCTCCGATATGAAGTCCTGGAGCAC
1261 ---------+---------+---------+---------+---------+---------+ 1320
     GTGCCGGGACCGCAAGCCGTGATCTGACGATCACAGGAGGCTATACTTCAGGACCTCGTG

T  A  L  A  F  G  T  R  L  L  V  S  S  D  M  K  S  W  S  T  -

TGTCCTGGCAGTGATGGGGAAAGCTTTTTCTGAAGCTGCCTTCACCACTGCCTACCTGTT
1321 ---------+---------+---------+---------+---------+---------+ 1380
     ACAGGACCGTCACTACCCCTTTCGAAAAAGACTTCGACGGAAGTGGTGACGGATGGACAA

V  L  A  V  M  G  K  A  F  S  E  A  A  F  T  T  A  Y  L  F  -

CACTTCAGAGTTGTACCCTACGGTGCTCAGACAGACAGGGATGGGGCTGACTGCACTGGT
1381 ---------+---------+---------+---------+---------+---------+ 1440
     GTGAAGTCTCAACATGGGATGCCACGAGTCTGTCTGTCCCTACCCCGACTGACGTGACCA

T  S  E  L  Y  P  T  V  L  R  Q  T  G  M  G  L  T  A  L  V  -

GGGCCGGCTGGGGGGCTCTTTGGCCCCACTGGCGGCCTTGCTGGATGGAGTGTGGCTGTC
1441 ---------+---------+---------+---------+---------+---------+ 1500
     CCCGGCCGACCCCCCGAGAAACCGGGGTGACCGCCGGAACGACCTACCTCACACCGACAG

G  R  L  G  G  S  L  A  P  L  A  A  L  L  D  G  V  W  L  S  -

ACTGCCCAAGCTTACTTATGGGGGGATCGCCCTGCTGGCTGCCGGCACCGCCCTCCTGCT
1501 ---------+---------+---------+---------+---------+---------+ 1560
     TGACGGGTTCGAATGAATACCCCCCTAGCGGGACGACCGACGGCCGTGGCGGGAGGACGA

L  P  K  L  T  Y  G  G  I  A  L  L  A  A  G  T  A  L  L  L  -

GCCAGAGACGAGGCAGGCACAGCTGCCAGAGACCATCCAGGACGTGGAGAGAAAGAGTGC
1561 ---------+---------+---------+---------+---------+---------+ 1620
     CGGTCTCTGCTCCGTCCGTGTCGACGGTCTCTGGTAGGTCCTGCACCTCTCTTTCTCACG

```
1621  CCCAACCAGTCTTCAGGAGGAAGAGATGCCCATGAAGCAGGTCCAGAACTAAGTGGGAGT  1680
      ---------+---------+---------+---------+---------+---------+
      GGGTTGGTCAGAAGTCCTCCTTCTCTACGGGTACTTCGTCCAGGTCTTGATTCACCCTCA

P  T  S  L  Q  E  E  E  M  P  M  K  Q  V  Q  N  *

1681  GGAGGCAGGCCCTCCACAGAAGCTCTGCAGCAGGGGCTGGGAGAGCAGAAGGGCAGGCCC  1740
      ---------+---------+---------+---------+---------+---------+
      CCTCCGTCCGGGAGGTGTCTTCGAGACGTCGTCCCCGACCCTCTCGTCTTCCCGTCCGGG

1741  TGCAACTCAGGCTGGGAGTATCGAACCCTCTGCCTAGGGCCGGAGTTGCTGCCAGTACCC  1800
      ---------+---------+---------+---------+---------+---------+
      ACGTTGAGTCCGACCCTCATAGCTTGGGAGACGGATCCCGGCCTCAACGACGGTCATGGG

1801  GCTCCCTCTGCTCATCCATCCTTGATTATTTGGCTTCTAGGAACAGTTGACTTCCCAGAA  1860
      ---------+---------+---------+---------+---------+---------+
      CGAGGGAGACGAGTAGGTAGGAACTAATAAACCGAAGATCCTTGTCAACTGAAGGGTCTT

1861  TGCAGTGGGCTGCTGGGCACCCCTCTCACGGTTGGGGAGGATTCTGTAAATAAAGGTGCC  1920
      ---------+---------+---------+---------+---------+---------+
      ACGTCACCCGACGACCCGTGGGGAGAGTGCCAACCCCTCCTAAGACATTTATTTCCACGG

1921  CCTTGGGTTGGGGCAATGGTGACGAGCTGTGGGAAGAGCCCTGGATAGGAAGCCACTGAG  1980
      ---------+---------+---------+---------+---------+---------+
      GGAACCCAACCCCGTTACCACTGCTCGACACCCTTCTCGGGACCTATCCTTCGGTGACTC

1981  TCTGCCCTGGGCTCTGATAAAACCTTCACCATTAACTTGCTGTGTGACCTTGGGCATGTG  2040
      ---------+---------+---------+---------+---------+---------+
      AGACGGGACCCGAGACTATTTTGGAAGTGGTAATTGAACGACACACTGGAACCCGTACAC

2041  GCTTTCCCTCTCTGGCCTCAGTCTGTTCATCTCCCAAATGGATAATGAAGCCTCTTGGGA  2100
      ---------+---------+---------+---------+---------+---------+
      CGAAAGGGAGAGACCGGAGTCAGACAAGTAGAGGGTTTACCTATTACTTCGGAGAACCCT

2101  GGCCCTACCATAGGATCTGTTGCCATGCTCAAATGAGTTACTGAATAAGGTGCTTCTGCT  2160
      ---------+---------+---------+---------+---------+---------+
      CCGGGATGGTATCCTAGACAACGGTACGAGTTTACTCAATGACTTATTCCACGAAGACGA

2161  TCTTCTAGAGATGGTGCTAAAGAAAGGACTAGCATATGAGACTTCTGGTACCAATGGGGC  2220
      ---------+---------+---------+---------+---------+---------+
      AGAAGATCTCTACCACGATTTCTTTCCTGATCGTATACTCTGAAGACCATGGTTACCCCG

2221  TGGTGGGCATGCTGTCCACTGTGTGGTGCTAGGACTGCCAATGCCAGGCCCAAGGGACAA  2280
      ---------+---------+---------+---------+---------+---------+
      ACCACCCGTACGACAGGTGACACACCACGATCCTGACGGTTACGGTCCGGGTTCCCTGTT

2281  AAAGAACAGAGCTTTTTGTTCTCATGGCTGGCCCTGCTACCTCCGAGGCACCCTGCAGGG  2340
      ---------+---------+---------+---------+---------+---------+
      TTTCTTGTCTCGAAAAACAAGAGTACCGACCGGGACGATGGAGGCTCCGTGGGACGTCCC

2341  CAATGCATGTCATCCCAACCCCCACACTCCCCATCCTCCAACCCACTGGTCTCATGCCCA  2400
      ---------+---------+---------+---------+---------+---------+
      GTTACGTACAGTAGGGTTGGGGGTGTGAGGGGTAGGAGGTTGGGTGACCAGAGTACGGGT
```

FIG. 2D

```
         AAGAAGAGTTGAAGGCATGGGAGCCAACATTTTATTGAAGAAGCCACAGAGGCTGAAATT
2401     ---------+---------+---------+---------+---------+---------+   2460
         TTCTTCTCAACTTCCGTACCCTCGGTTGTAAAATAACTTCTTCGGTGTCTCCGACTTTAA

CAATAAACACAAGTTTTATGAGTAAAAAAAAAAAAAAAAA
2461     ---------+---------+---------+---------+-   2501
         GTTATTTGTGTTCAAAATACTCATTTTTTTTTTTTTTTTT
```

FIG. 2E

```
     CTGCACCTGAAGCATTTGGTGGGTGAGCAGCATGGGCTTTGAGGAGCTGCTGGAGCAGGT
  1  ---------+---------+---------+---------+---------+---------+   60
     GACGTGGACTTCGTAAACCACCCACTCGTCGTACCCGAAACTCCTCGACGACCTCGTCCA

M  G  F  E  E  L  L  E  Q  V  -

GGGCGGCTTTGGGCCCTTCCAACTGCGGAATGTGGCACTGCTGGCCCTGCCCCGAGTGCT
 61  ---------+---------+---------+---------+---------+---------+   120
     CCCGCCGAAACCCGGGAAGGTTGACGCCTTACACCGTGACGACCGGGACGGGGCTCACGA

G  G  F  G  P  F  Q  L  R  N  V  A  L  L  A  L  P  R  V  L  -

GCTACCACTGCACTTCCTCCTGCCCATCTTCCTGGCTGCCGTGCCTGCCCACCGATGTGC
121  ---------+---------+---------+---------+---------+---------+   180
     CGATGGTGACGTGAAGGAGGACGGGTAGAAGGACCGACGGCACGGACGGGTGGCTACACG

L  P  L  H  F  L  L  P  I  F  L  A  A  V  P  A  H  R  C  A  -

CCTGCCGGGTGCCCCTGCCAACTTCAGCCATCAGGATGTGTGGCTGGAGGCCCATCTTCC
181  ---------+---------+---------+---------+---------+---------+   240
     GGACGGCCCACGGGGACGGTTGAAGTCGGTAGTCCTACACACCGACCTCCGGGTAGAAGG

L  P  G  A  P  A  N  F  S  H  Q  D  V  W  L  E  A  H  L  P  -

CCGGGAGCCTGATGGCACGCTCAGCTCCTGCCTCCGCTTTGCCTATCCCCAGGCTCTCCC
241  ---------+---------+---------+---------+---------+---------+   300
     GGCCCTCGGACTACCGTGCGAGTCGAGGACGGAGGCGAAACGGATAGGGGTCCGAGAGGG

R  E  P  D  G  T  L  S  S  C  L  R  F  A  Y  P  Q  A  L  P  -

CAACACCACGTTGGGGGAAGAAAGGCAGAGCCGTGGGGAGCTGGAGGATGAACCTGCCAC
301  ---------+---------+---------+---------+---------+---------+   360
     GTTGTGGTGCAACCCCCTTCTTTCCGTCTCGGCACCCCTCGACCTCCTACTTGGACGGTG

N  T  T  L  G  E  E  R  Q  S  R  G  E  L  E  D  E  P  A  T  -

AGTGCCCTGCTCTCAGGGCTGGGAGTACGACCACTCAGAATTCTCCTCTACCATTGCAAC
361  ---------+---------+---------+---------+---------+---------+   420
     TCACGGGACGAGAGTCCCGACCCTCATGCTGGTGAGTCTTAAGAGGAGATGGTAACGTTG

V  P  C  S  Q  G  W  E  Y  D  H  S  E  F  S  S  T  I  A  T  -

TGAGTGGGATCTGGTGTGTGAGCAGAAAGGTCTGAACAGAGCTGCGTCCACTTTCTTCTT
421  ---------+---------+---------+---------+---------+---------+   480
     ACTCACCCTAGACCACACACTCGTCTTTCCAGACTTGTCTCGACGCAGGTGAAAGAAGAA

E  W  D  L  V  C  E  Q  K  G  L  N  R  A  A  S  T  F  F  F  -

CGCCGGTGTGCTGGTGGGGGCTGTGGCCTTTGGATATCTGTCCGACAGGTTTGGGCGGCG
481  ---------+---------+---------+---------+---------+---------+   540
     GCGGCCACACGACCACCCCCGACACCGGAAACCTATAGACAGGCTGTCCAAACCCGCCGC

```
      GCGTCTGCTGCTGGTAGCCTACGTGAGTACCCTGGTGCTGGGCCTGGCATCTGCAGCCTC
541   ---------+---------+---------+---------+---------+---------+   600
      CGCAGACGACGACCATCGGATGCACTCATGGGACCACGACCCGGACCGTAGACGTCGGAG

R  L  L  L  V  A  Y  V  S  T  L  V  L  G  L  A  S  A  A  S  -

CGTCAGCTATGTAATGTTTGCCATCACCCGCACCCTTACTGGCTCAGCCCTGGCTGGTTT
601   ---------+---------+---------+---------+---------+---------+   660
      GCAGTCGATACATTACAAACGGTAGTGGGCGTGGGAATGACCGAGTCGGGACCGACCAAA

V  S  Y  V  M  F  A  I  T  R  T  L  T  G  S  A  L  A  G  F  -

TACCATCATCGTGATGCCACTGGAGCTGGAGTGGCTGGATGTGGAGCACCGCACCGTGGC
661   ---------+---------+---------+---------+---------+---------+   720
      ATGGTAGTAGCACTACGGTGACCTCGACCTCACCGACCTACACCTCGTGGCGTGGCACCG

T  I  I  V  M  P  L  E  L  E  W  L  D  V  E  H  R  T  V  A  -

TGGAGTCCTGAGCAGCACCTTCTGGACAGGGGGCGTGATGCTGCTGGCACTGGTTGGGTA
721   ---------+---------+---------+---------+---------+---------+   780
      ACCTCAGGACTCGTCGTGGAAGACCTGTCCCCCGCACTACGACGACCGTGACCAACCCAT

G  V  L  S  S  T  F  W  T  G  G  V  M  L  L  A  L  V  G  Y  -

CCTGATACGGGACTGGCGATGGCTTCTGCTAGCTGTCACCCTGCCTTGTGCCCCAAGCAT
781   ---------+---------+---------+---------+---------+---------+   840
      GGACTATGCCCTGACCGCTACCGAAGACGATCGACAGTGGGACGGAACACGGGGTTCGTA

L  I  R  D  W  R  W  L  L  L  A  V  T  L  P  C  A  P  S  I  -

CCTCAGCCTCTGGTGGGTGCCTGAGTCTGCACGCTGGCTTCTGACCCAAGGCCATGTGAA
841   ---------+---------+---------+---------+---------+---------+   900
      GGAGTCGGAGACCACCCACGGACTCAGACGTGCGACCGAAGACTGGGTTCCGGTACACTT

L  S  L  W  W  V  P  E  S  A  R  W  L  L  T  Q  G  H  V  K  -

AGAGGCCCACAGGTACTTGCTCCACTGTGCCAGGCTCAATGGGCGGCCAGTGTGTGAGGA
901   ---------+---------+---------+---------+---------+---------+   960
      TCTCCGGGTGTCCATGAACGAGGTGACACGGTCCGAGTTACCCGCCGGTCACACACTCCT

E  A  H  R  Y  L  L  H  C  A  R  L  N  G  R  P  V  C  E  D  -

CAGCTTCAGCCAGGAGGCTGTGAGCAAAGTGGCCGCCGGGGAACGGGTGGTCCGAAGACC
961   ---------+---------+---------+---------+---------+---------+   1020
      GTCGAAGTCGGTCCTCCGACACTCGTTTCACCGGCGGCCCCTTGCCCACCAGGCTTCTGG

S  F  S  Q  E  A  V  S  K  V  A  A  G  E  R  V  V  R  R  P  -

TTCATACCTAGACCTGTTCCGCACACCACGGCTCCGACACATCTCACTGTGCTGCGTGGT
1021  ---------+---------+---------+---------+---------+---------+   1080
      AAGTATGGATCTGGACAAGGCGTGTGGTGCCGAGGCTGTGTAGAGTGACACGACGCACCA

```
        GGTGTGGTTCGGAGTGAACTTCTCCTATTACGGCCTGAGTCTGGATGTGTCGGGGCTGGG
1081    ------------------------------------------------------------    1140
        CCACACCAAGCCTCACTTGAAGAGGATAATGCCGGACTCAGACCTACACAGCCCCGACCC

V  W  F  G  V  N  F  S  Y  Y  G  L  S  L  D  V  S  G  L  G  -

GCTGAACGTGTACCAGACACAGCTGTTGTTCGGGGCTGTGGAACTGCCCTCCAAGCTGCT
1141    ------------------------------------------------------------    1200
        CGACTTGCACATGGTCTGTGTCGACAACAAGCCCCGACACCTTGACGGGAGGTTCGACGA

L  N  V  Y  Q  T  Q  L  L  F  G  A  V  E  L  P  S  K  L  L  -

GGTCTACTTGTCGGTGCGCTACGCAGGACGCCGCCTCACGCAAGCCGGGACACTGCTGGG
1201    ------------------------------------------------------------    1260
        CCAGATGAACAGCCACGCGATGCGTCCTGCGGCGGAGTGCGTTCGGCCCTGTGACGACCC

V  Y  L  S  V  R  Y  A  G  R  R  L  T  Q  A  G  T  L  L  G  -

CACGGCCCTGGCGTTCGGCACTAGACTGCTAGTGTCCTCCGATATGAAGTCCTGGAGCAC
1261    ------------------------------------------------------------    1320
        GTGCCGGGACCGCAAGCCGTGATCTGACGATCACAGGAGGCTATACTTCAGGACCTCGTG

T  A  L  A  F  G  T  R  L  L  V  S  S  D  M  K  S  W  S  T  -

TGTCCTGGCAGTGATGGGGAAAGCTTTTTCTGAAGCTGCCTTCACCACTGCCTACCTGTT
1321    ------------------------------------------------------------    1380
        ACAGGACCGTCACTACCCCTTTCGAAAAAGACTTCGACGGAAGTGGTGACGGATGGACAA

V  L  A  V  M  G  K  A  F  S  E  A  A  F  T  T  A  Y  L  F  -

CACTTCAGAGTTGTACCCTACGGTGCTCAGACAGACAGGGATGGGGCTGACTGCACTGGT
1381    ------------------------------------------------------------    1440
        GTGAAGTCTCAACATGGGATGCCACGAGTCTGTCTGTCCCTACCCCGACTGACGTGACCA

T  S  E  L  Y  P  T  V  L  R  Q  T  G  M  G  L  T  A  L  V  -

GGGCCGGCTGGGGGGCTCTTTGGCCCCACTGGCGGCCTTGCTGGATGGAGTGTGGCTGTC
1441    ------------------------------------------------------------    1500
        CCCGGCCGACCCCCCGAGAAACCGGGGTGACCGCCGGAACGACCTACCTCACACCGACAG

G  R  L  G  G  S  L  A  P  L  A  A  L  L  D  G  V  W  L  S  -

ACTGCCCAAGCTTACTTATGGGGGATCGCCCTGCTGGCTGCCGGCACCGCCCTCCTGCT
1501    ------------------------------------------------------------    1560
        TGACGGGTTCGAATGAATACCCCCCTAGCGGGACGACCGACGGCCGTGGCGGGAGGACGA

L  P  K  L  T  Y  G  G  I  A  L  L  A  A  G  T  A  L  L  L  -

GCCAGAGACGAGGCAGGCACAGCTGCCAGAGACCATCCAGGACGTGGAGAGAAAGAGAGA
1561    ------------------------------------------------------------    1620
        CGGTCTCTGCTCCGTCCGTGTCGACGGTCTCTGGTAGGTCCTGCACCTCTCTTTCTCTCT

```
       TGGTGCTAAAGAAAGGACTAGCATATGAGACTTCTGGTACCAATGGGGCTGGTGGGCATG
1621   ---------+---------+---------+---------+---------+---------+   1680
       ACCACGATTTCTTTCCTGATCGTATACTCTGAAGACCATGGTTACCCCGACCACCCGTAC

G   A   K   E   R   T   S   I   *

CTGTCCACTGTGTGGTGCTAGGACTGCCAATGCCAGGCCCAAGGGACAAAAAGAACAGAG
1681   ---------+---------+---------+---------+---------+---------+   1740
       GACAGGTGACACACCACGATCCTGACGGTTACGGTCCGGGTTCCCTGTTTTTCTTGTCTC

CTTTTTGTTCTCATGGCTGGCCCTGCTACCTCCGAGGCACCCTGCAGGGCAATGCATGTC
1741   ---------+---------+---------+---------+---------+---------+   1800
       GAAAAACAAGAGTACCGACCGGGACGATGGAGGCTCCGTGGGACGTCCCGTTACGTACAG

ATCCCAACCCCCACACTCCCCATCCTCCAACCCACTGGTCTCATGCCCAAAGAAGAGTTG
1801   ---------+---------+---------+---------+---------+---------+   1860
       TAGGGTTGGGGGTGTGAGGGGTAGGAGGTTGGGTGACCAGAGTACGGGTTTCTTCTCAAC

AAGGCATGGGAGCCAACATTTTATTGAAGAAGCCACAGAGGCTGAAATTCAATAAACACA
1861   ---------+---------+---------+---------+---------+---------+   1920
       TTCCGTACCCTCGGTTGTAAAATAACTTCTTCGGTGTCTCCGACTTTAAGTTATTTGTGT

AGTTTTATGAGTAAAAAAAAAAAAAAAAAA
1921   ---------+---------+---------+   1950
       TCAAAATACTCATTTTTTTTTTTTTTTTTT
```

FIG. 3D

```
    GCAGGGACCTCAACTACACTGATCACCAGCCCCATCGGATCCAGACCCGGCCACCAGTGC
1   ---------+---------+---------+---------+---------+---------+   60
    CGTCCCTGGAGTTGATGTGACTAGTGGTCGGGGTAGCCTAGGTCTGGGCCGGTGGTCACG

CATGACCTTCTCGGAGATCCTGGACCGTGTGGGAAGCATGGGCCATTTCCAGTTCCTGCA
61  ---------+---------+---------+---------+---------+---------+   120
    GTACTGGAAGAGCCTCTAGGACCTGGCACACCCTTCGTACCCGGTAAAGGTCAAGGACGT
      M  T  F  S  E  I  L  D  R  V  G  S  M  G  H  F  Q  F  L  H -

TGTAGCCATACTGGGCCTCCCGATCCTCAACATGGCCAACCACAACCTGCTGCAGATCTT
121 ---------+---------+---------+---------+---------+---------+   180
    ACATCGGTATGACCCGGAGGGCTAGGAGTTGTACCGGTTGGTGTTGGACGACGTCTAGAA

CACAGCCGCCACCCCTGTCCACCACTGTCGCCCGCCCCACAATGCCTCCACAGGGCCTTG
181 ---------+---------+---------+---------+---------+---------+   240
    GTGTCGGCGGTGGGGACAGGTGGTGACAGCGGGCGGGGTGTTACGGAGGTGTCCCGGAAC

GGTGCTCCCCATGGGCCCAAATGGGAAGCCTGAGAGGTGCCTCCGTTTTGTACATCCGCC
241 ---------+---------+---------+---------+---------+---------+   300
    CCACGAGGGGTACCCGGGTTTACCCTTCGGACTCTCCACGGAGGCAAAACATGTAGGCGG

CAATGCCAGCCTGCCCAATGACACCCAGAGGGCCATGGAGCCATGCCTGGATGGCTGGGT
301 ---------+---------+---------+---------+---------+---------+   360
    GTTACGGTCGGACGGGTTACTGTGGGTCTCCCGGTACCTCGGTACGGACCTACCGACCCA

CTACAACAGCACCAAGGACTCCATTGTGACAGAGTGGGACTTGGTGTGCAACTCCAACAA
361 ---------+---------+---------+---------+---------+---------+   420
    GATGTTGTCGTGGTTCCTGAGGTAACACTGTCTCACCCTGAACCACACGTTGAGGTTGTT

ACTGAAGGAGATGGCCCAGTCTATCTTCATGGCAGGTATACTGATTGGAGGGCTCGTGCT
421 ---------+---------+---------+---------+---------+---------+   480
    TGACTTCCTCTACCGGGTCAGATAGAAGTACCGTCCATATGACTAACCTCCCGAGCACGA

TGGAGACCTGTCTGACAGGTTTGGCCGCAGGCCCATCCTGACCTGCAGCTACCTGCTGCT
481 ---------+---------+---------+---------+---------+---------+   540
    ACCTCTGGACAGACTGTCCAAACCGGCGTCCGGGTAGGACTGGACGTCGATGGACGACGA

GGCAGCCAGCGGCTCCGGTGCAGCCTTCAGCCCCACCTTCCCCATCTACATGGTCTTCCG
541 ---------+---------+---------+---------+---------+---------+   600
```

*FIG. 4A*

```
                CCGTCGGTCGCCGAGGCCACGTCGGAAGTCGGGGTGGAAGGGGTAGATGTACCAGAAGGC

A  A  S  G  S  G  A  A  F  S  P  T  F  P  I  Y  M  V  F  R  -

CTTCCTGTGTGGCTTTGGCATCTCAGGCATTACCCTGAGCACCGTCATCTTGAATGTGGA
  601   ---------+---------+---------+---------+---------+---------+  660
        GAAGGACACACCGAAACCGTAGAGTCCGTAATGGGACTCGTGGCAGTAGAACTTACACCT

F  L  C  G  F  G  I  S  G  I  T  L  S  T  V  I  L  N  V  E  -

ATGGGTGCCTACCCGGATGCGGGCCATCATGTCGACAGCACTCGGGTACTGCTACACCTT
  661   ---------+---------+---------+---------+---------+---------+  720
        TACCCACGGATGGGCCTACGCCCGGTAGTACAGCTGTCGTGAGCCCATGACGATGTGGAA

W  V  P  T  R  M  R  A  I  M  S  T  A  L  G  Y  C  Y  T  F  -

TGGCCAGTTCATTCTGCCCGGCCTGGCCTACGCCATCCCCCAGTGGCGTTGGCTGCAGTT
  721   ---------+---------+---------+---------+---------+---------+  780
        ACCGGTCAAGTAAGACGGGCCGGACCGGATGCGGTAGGGGGTCACCGCAACCGACGTCAA

G  Q  F  I  L  P  G  L  A  Y  A  I  P  Q  W  R  W  L  Q  L  -

AACTGTGTCCATTCCCTTCTTCGTCTTCTTCCTATCATCCTGGTGGACACCAGAGTCCAT
  781   ---------+---------+---------+---------+---------+---------+  840
        TTGACACAGGTAAGGGAAGAAGCAGAAGAAGGATAGTAGGACCACCTGTGGTCTCAGGTA

T  V  S  I  P  F  F  V  F  F  L  S  S  W  W  T  P  E  S  I  -

ACGCTGGTTGGTCTTGTCTGGAAAGTCCTCGAAGGCCCTGAAGATACTCCGGCGGGTGGC
  841   ---------+---------+---------+---------+---------+---------+  900
        TGCGACCAACCAGAACAGACCTTTCAGGAGCTTCCGGGACTTCTATGAGGCCGCCCACCG

R  W  L  V  L  S  G  K  S  S  K  A  L  K  I  L  R  R  V  A  -

TGTCTTCAATGGCAAGAAGGAAGAGGGAGAAAGGCTCAGCTTGGAGGAGCTCAAACTCAA
  901   ---------+---------+---------+---------+---------+---------+  960
        ACAGAAGTTACCGTTCTTCCTTCTCCCTCTTTCCGAGTCGAACCTCCTCGAGTTTGAGTT

V  F  N  G  K  K  E  E  G  E  R  L  S  L  E  E  L  K  L  N  -

CCTGCAGAAGGAGATCTCCTTGGCCAAGGCCAAGTACACCGCAAGTGACCTGTTCCGGAT
  961   ---------+---------+---------+---------+---------+---------+  1020
        GGACGTCTTCCTCTAGAGGAACCGGTTCCGGTTCATGTGGCGTTCACTGGACAAGGCCTA

L  Q  K  E  I  S  L  A  K  A  K  Y  T  A  S  D  L  F  R  I  -

ACCCATGCTGCGCCGCATGACCTTCTGTCTTTCCCTGGCCTGGTTTGCTACCGGTTTTGC
  1021  ---------+---------+---------+---------+---------+---------+  1080
        TGGGTACGACGCGGCGTACTGGAAGACAGAAAGGGACCGGACCAAACGATGGCCAAAACG

P  M  L  R  R  M  T  F  C  L  S  L  A  W  F  A  T  G  F  A  -

CTACTATAGTTTGGCTATGGGTGTGGAAGAATTTGGAGTCAACCTCTACATCCTCCAGAT
  1081  ---------+---------+---------+---------+---------+---------+  1140
```

FIG. 4B

```
              GATGATATCAAACCGATACCCACACCTTCTTAAACCTCAGTTGGAGATGTAGGAGGTCTA
               Y  Y  S  L  A  M  G  V  E  E  F  G  V  N  L  Y  I  L  Q  I  -

CATCTTTGGTGGGGTCGATGTCCCAGCCAAGTTCATCACCATCCTCTCCTTAAGCTACCT
       1141   ---------+---------+---------+---------+---------+---------+   1200
              GTAGAAACCACCCCAGCTACAGGGTCGGTTCAAGTAGTGGTAGGAGAGGAATTCGATGGA
               I  F  G  G  V  D  V  P  A  K  F  I  T  I  L  S  L  S  Y  L  -

GGGCCGGCATACCACTCAGGCCGCTGCCCTGCTCCTGGCAGGAGGGGCCATCTTGGCTCT
       1201   ---------+---------+---------+---------+---------+---------+   1260
              CCCGGCCGTATGGTGAGTCCGGCGACGGGACGAGGACCGTCCTCCCCGGTAGAACCGAGA
               G  R  H  T  T  Q  A  A  A  L  L  L  A  G  G  A  I  L  A  L  -

CACCTTTGTGCCCTTGGACTTGCAGACCGTGAGGACAGTATTGGCTGTGTTTGGGAAGGG
       1261   ---------+---------+---------+---------+---------+---------+   1320
              GTGGAAACACGGGAACCTGAACGTCTGGCACTCCTGTCATAACCGACACAAACCCTTCCC
               T  F  V  P  L  D  L  Q  T  V  R  T  V  L  A  V  F  G  K  G  -

ATGCCTATCCAGCTCCTTCAGCTGCCTCTTCCTCTACACAAGTGAATTATACCCCACAGT
       1321   ---------+---------+---------+---------+---------+---------+   1380
              TACGGATAGGTCGAGGAAGTCGACGGAGAAGGAGATGTGTTCACTTAATATGGGGTGTCA
               C  L  S  S  S  F  S  C  L  F  L  Y  T  S  E  L  Y  P  T  V  -

CATCAGGCAAACAGGTATGGGCGTAAGTAACCTGTGGACCCGCGTGGGAAGCATGGTGTC
       1381   ---------+---------+---------+---------+---------+---------+   1440
              GTAGTCCGTTTGTCCATACCCGCATTCATTGGACACCTGGGCGCACCCTTCGTACCACAG
               I  R  Q  T  G  M  G  V  S  N  L  W  T  R  V  G  S  M  V  S  -

CCCGCTGGTGAAAATCACGGGTGAGGTACAGCCCTTCATCCCCAATATCATCTACGGGAT
       1441   ---------+---------+---------+---------+---------+---------+   1500
              GGGCGACCACTTTTAGTGCCCACTCCATGTCGGGAAGTAGGGGTTATAGTAGATGCCCTA
               P  L  V  K  I  T  G  E  V  Q  P  F  I  P  N  I  I  Y  G  I  -

CACCGCCCTCCTCGGGGCAGTGCTGCCCTCTTCCTGCCTGAGACCCTGAATCAGCCCTT
       1501   ---------+---------+---------+---------+---------+---------+   1560
              GTGGCGGGAGGAGCCCCCGTCACGACGGGAGAAGGACGGACTCTGGGACTTAGTCGGGAA
               T  A  L  L  G  G  S  A  A  L  F  L  P  E  T  L  N  Q  P  L  -

GCCAGAGACTATCGAAGACCTGGAAAACTGGTCCCTGCGGGCAAAGAAGCCAAAGCAGGA
       1561   ---------+---------+---------+---------+---------+---------+   1620
              CGGTCTCTGATAGCTTCTGGACCTTTTGACCAGGGACGCCCGTTTCTTCGGTTTCGTCCT
               P  E  T  I  E  D  L  E  N  W  S  L  R  A  K  K  P  K  Q  E  -

GCCAGAGGTGGAAAAGGCCTCCCAGAGGATCCCTCTACAGCCTCACGGACCAGGCCTGGG
       1621   ---------+---------+---------+---------+---------+---------+   1680
```

*FIG. 4C*

```
              CGGTCTCCACCTTTTCCGGAGGGTCTCCTAGGGAGATGTCGGAGTGCCTGGTCCGGACCC

P   E   V   E   K   A   S   Q   R   I   P   L   Q   P   H   G   P   G   L   G   -

CTCCAGCTGAGGACAACGGAACCCCCTTTCCCTGCCCTCCAGAGACTGATCCTAGCCAGG
  1681    ---------+---------+---------+---------+---------+---------+   1740
          GAGGTCGACTCCTGTTGCCTTGGGGGAAAGGGACGGGAGGTCTCTGACTAGGATCGGTCC

S   S   *

CACCTTAGGAGTATAGGGAGGCCCCATATAGGTCCATCCTCCTAGGATGAAGCCTTCTGA
  1741    ---------+---------+---------+---------+---------+---------+   1800
          GTGGAATCCTCATATCCCTCCGGGGTATATCCAGGTAGGAGGATCCTACTTCGGAAGACT

GAGCTTGGTGAAGGTGTCTCCATCACCACCACCAGAGCCTCCTGCCCAGCCCTGGCCAGT
  1801    ---------+---------+---------+---------+---------+---------+   1860
          CTCGAACCACTTCCACAGAGGTAGTGGTGGTGGTCTCGGAGGACGGGTCGGGACCGGTCA

TCAAAGGTTCAAGCCATCCCTGCCCTTGTTCTCCCTGCAACCCAAGCCCTGCCATTCTTC
  1861    ---------+---------+---------+---------+---------+---------+   1920
          AGTTTCCAAGTTCGGTAGGGACGGGAACAAGAGGGACGTTGGGTTCGGGACGGTAAGAAG

TGTCTAGCCCTTCCCCACTGGCCAACTTCCCCCACTGTCCCGGTCCTCTTCCCCTGAGGT
  1921    ---------+---------+---------+---------+---------+---------+   1980
          ACAGATCGGGAAGGGGTGACCGGTTGAAGGGGGTGACAGGGCCAGGAGAAGGGGACTCCA

CCCCTGATATCCCCTGGCTCAGTCCTAACAAGACTGAGTCTTAACAAGATGAGAAGTCCT
  1981    ---------+---------+---------+---------+---------+---------+   2040
          GGGGACTATAGGGGACCGAGTCAGGATTGTTCTGACTCAGAATTGTTCTACTCTTCAGGA

CCCCTTCTTGCCTCCCACACTTTTCTTTGATGGGAGGTTTCAATAAACAGCGATAAGAAC
  2041    ---------+---------+---------+---------+---------+---------+   2100
          GGGGAAGAACGGAGGGTGTGAAAAGAAACTACCCTCCAAAGTTATTTGTCGCTATTCTTG

TCTAAAAAAAAAAAAAAAAAA
  2101    ---------+---------+-   2121
          AGATTTTTTTTTTTTTTTTTT
```

FIG. 4D

```
     CAAATTATTTCTTACGTGACTTTAGAGAAAACGGCTACCTATCTGACCCCAAAACGACTT
1    ---------+---------+---------+---------+---------+---------+  60
     GTTTAATAAAGAATGCACTGAAATCTCTTTTGCCGATGGATAGACTGGGGTTTTGCTGAA

GAGGAAACTGTTTCCACGGTCCTGCTGCAGGGGGGAAGCACAGTCGTCAAGAAGAGAGTG
61   ---------+---------+---------+---------+---------+---------+  120
     CTCCTTTGACAAAGGTGCCAGGACGACGTCCCCCCTTCGTGTCAGCAGTTCTTCTCTCAC

GGGTCAGGATCAAAACACATTTAGTGTGACTTAGGGAAAGAAAACATTTTCCCTCTTTGA
121  ---------+---------+---------+---------+---------+---------+  180
     CCCAGTCCTAGTTTTGTGTAAATCACACTGAATCCCTTTCTTTTGTAAAAGGGAGAAACT

ACCTCTCTGGATACAGTCATTTTGCCTCTACTTGAGGATCAACTGTTCAACCTCAATGGC
181  ---------+---------+---------+---------+---------+---------+  240
     TGGAGAGACCTATGTCAGTAAAACGGAGATGAACTCCTAGTTGACAAGTTGGAGTTACCG
                                                              M  A -

CTTTCAGGACCTCCTGGGTCACGCTGGTGACCTGTGGAGATTCCAGATCCTTCAGACTGT
241  ---------+---------+---------+---------+---------+---------+  300
     GAAAGTCCTGGAGGACCCAGTGCGACCACTGGACACCTCTAAGGTCTAGGAAGTCTGACA
      F  Q  D  L  L  G  H  A  G  D  L  W  R  F  Q  I  L  Q  T  V -

TTTTCTCTCAATCTTTGCTGTTGCTACATACCTTCATTTTATGCTGGAGAACTTCACTGC
301  ---------+---------+---------+---------+---------+---------+  360
     AAAAGAGAGTTAGAAACGACAACGATGTATGGAAGTAAAATACGACCTCTTGAAGTGACG
      F  L  S  I  F  A  V  A  T  Y  L  H  F  M  L  E  N  F  T  A -

ATTCATACCTGGCCATCGCTGCTGGGTCCACATCCTGGACAATGACACTGTCTCTGACAA
361  ---------+---------+---------+---------+---------+---------+  420
     TAAGTATGGACCGGTAGCGACGACCCAGGTGTAGGACCTGTTACTGTGACAGAGACTGTT
      F  I  P  G  H  R  C  W  V  H  I  L  D  N  D  T  V  S  D  N -

TGACACTGGGGCCCTCAGCCAAGATGCACTCTTGAGAATCTCCATCCCACTGGACTCAAA
421  ---------+---------+---------+---------+---------+---------+  480
     ACTGTGACCCCGGGAGTCGGTTCTACGTGAGAACTCTTAGAGGTAGGGTGACCTGAGTTT
      D  T  G  A  L  S  Q  D  A  L  L  R  I  S  I  P  L  D  S  N -

CATGAGGCCAGAGAAGTGTCGTCGCTTTGTTCATCCTCAGTGGCAGCTCCTTCACCTGAA
481  ---------+---------+---------+---------+---------+---------+  540
     GTACTCCGGTCTCTTCACAGCAGCGAAACAAGTAGGAGTCACCGTCGAGGAAGTGGACTT
      M  R  P  E  K  C  R  R  F  V  H  P  Q  W  Q  L  L  H  L  N -

TGGGACCTTCCCCAACACAAGTGACGCAGACATGGAGCCCTGTGTGGATGGCTGGGTGTA
541  ---------+---------+---------+---------+---------+---------+  600
     ACCCTGGAAGGGGTTGTGTTCACTGCGTCTGTACCTCGGGACACACCTACCGACCCACAT
      G  T  F  P  N  T  S  D  A  D  M  E  P  C  V  D  G  W  V  Y -
```

*FIG. 5A*

```
     TGACAGAATCTCCTTCTCATCCACCATCGGTGACCTGAAGTGGGATCTGGTATGTGACTC
601  ------------+---------+---------+---------+---------+---------+  660
     ACTGTCTTAGAGGAAGAGTAGGTGGTAGCCACTGGACTTCACCCTAGACCATACACTGAG

D  R  I  S  F  S  S  T  I  G  D  L  K  W  D  L  V  C  D  S  -

TCAATCACTGACTTCAGTGGCTAAATTTGTATTCATGGCTGGAATGATGTTGGGAGGCAT
661  ------------+---------+---------+---------+---------+---------+  720
     AGTTAGTGACTGAAGTCACCGATTTAAACATAAGTACCGACCTTACTACAACCCTCCGTA

Q  S  L  T  S  V  A  K  F  V  F  M  A  G  M  M  L  G  G  I  -

CCAGGTTGCCATTGTTGGCACTTGTGCAGCGTTGGCTCCCACTTTCCTCATTTACTGCTC
721  ------------+---------+---------+---------+---------+---------+  780
     GGTCCAACGGTAACAACCGTGAACACGTCGCAACCGAGGGTGAAAGGAGTAAATGACGAG

L  G  V  H  L  S  D  R  F  G  R  S  F  V  L  R  W  C  Y  L  -

CCAGGTTGCCATTGTTGGCACTTGTGCAGCGTTGGCTCCCACTTTCCTCATTTACTGCTC
781  ------------+---------+---------+---------+---------+---------+  840
     GGTCCAACGGTAACAACCGTGAACACGTCGCAACCGAGGGTGAAAGGAGTAAATGACGAG

Q  V  A  I  V  G  T  C  A  A  L  A  P  T  F  L  I  Y  C  S  -

AGTACGCTTCTTGTCTGGGATTGCTGCAATGAGCTTCATAACAAATACTATTATGTTAAT
841  ------------+---------+---------+---------+---------+---------+  900
     TCATGCGAAGAACAGACCCTAACGACGTTACTCGAAGTATTGTTTATGATAATACAATTA

V  R  F  L  S  G  I  A  A  M  S  F  I  T  N  T  I  M  L  I  -

AGCCGAGTGGGCAACACACAGATTCCAGGCCATGGGAATTACATTGGGAATGTGCCCTTC
901  ------------+---------+---------+---------+---------+---------+  960
     TCGGCTCACCCGTTGTGTGTCTAAGGTCCGGTACCCTTAATGTAACCCTTACACGGGAAG

A  E  W  A  T  H  R  F  Q  A  M  G  I  T  L  G  M  C  P  S  -

TGGTATTGCATTTATGACCCTGGCAGGCCTGGCTTTTGCCATTCGAGACTGGCATATCCT
961  ------------+---------+---------+---------+---------+---------+  1020
     ACCATAACGTAAATACTGGGACCGTCCGGACCGAAAACGGTAAGCTCTGACCGTATAGGA

G  I  A  F  M  T  L  A  G  L  A  F  A  I  R  D  W  H  I  L  -

CCAGCTGGTGGTGTCTGTACCATACTTTGTGATCTTTCTGACCTCAAGTTGGCTGCTAGA
1021 ------------+---------+---------+---------+---------+---------+  1080
     GGTCGACCACCACAGACATGGTATGAAACACTAGAAAGACTGGAGTTCAACCGACGATCT

Q  L  V  V  S  V  P  Y  F  V  I  F  L  T  S  S  W  L  L  E  -

GTCTGCTCGGTGGCTCATTATCAACAATAAACCAGAGGAAGGCTTAAAGGAACTTAGAAA
1081 ------------+---------+---------+---------+---------+---------+  1140
     CAGACGAGCCACCGAGTAATAGTTGTTATTTGGTCTCCTTCCGAATTTCCTTGAATCTTT

```
      AGCTGCACACAGGAGTGGAATGAAGAATGCCAGAGACACCCTAACCCTGGAGATTTTGAA
1141  ---------+---------+---------+---------+---------+---------+  1200
      TCGACGTGTGTCCTCACCTTACTTCTTACGGTCTCTGTGGGATTGGGACCTCTAAAACTT

A  A  H  R  S  G  M  K  N  A  R  D  T  L  T  L  E  I  L  K  -

ATCCACCATGAAAAAAGAACTGGAGGCAGCACAAAAAAAAAAACCTTCTCTGTGTGAAAT
1201  ---------+---------+---------+---------+---------+---------+  1260
      TAGGTGGTACTTTTTTCTTGACCTCCGTCGTGTTTTTTTTTTGGAAGAGACACACTTTA

S  T  M  K  K  E  L  E  A  A  Q  K  K  K  P  S  L  C  E  M  -

GCTCCACATGCCCAACATATGTAAAAGGATCTCCCTCCTGTCCTTTACGAGATTTGCAAA
1261  ---------+---------+---------+---------+---------+---------+  1320
      CGAGGTGTACGGGTTGTATACATTTTCCTAGAGGGAGGACAGGAAATGCTCTAAACGTTT

L  H  M  P  N  I  C  K  R  I  S  L  L  S  F  T  R  F  A  N  -

CTTTATGGCCTATTTTGGCCTTAATCTCCATGTCCAGCATCTGGGGAACAATGTTTTCCT
1321  ---------+---------+---------+---------+---------+---------+  1380
      GAAATACCGGATAAAACCGGAATTAGAGGTACAGGTCGTAGACCCCTTGTTACAAAAGGA

F  M  A  Y  F  G  L  N  L  H  V  Q  H  L  G  N  N  V  F  L  -

GTTGCAGACTCTCTTTGGTGCAGTCATCCTCCTGGCCAACTGTGTTGCACCTTGGGCACT
1381  ---------+---------+---------+---------+---------+---------+  1440
      CAACGTCTGAGAGAAACCACGTCAGTAGGAGGACCGGTTGACACAACGTGGAACCCGTGA

L  Q  T  L  F  G  A  V  I  L  L  A  N  C  V  A  P  W  A  L  -

GAAATACATGAACCGTCGAGCAAGCCAGATGCTTCTCATGTTCCTACTGGCAATCTGCCT
1441  ---------+---------+---------+---------+---------+---------+  1500
      CTTTATGTACTTGGCAGCTCGTTCGGTCTACGAAGAGTACAAGGATGACCGTTAGACGGA

K  Y  M  N  R  R  A  S  Q  M  L  L  M  F  L  L  A  I  C  L  -

TCTGGCCATCATATTTGTGCCACAAGAAATGCAGACGCTGCGTGAGGTTTTGGCAACACT
1501  ---------+---------+---------+---------+---------+---------+  1560
      AGACCGGTAGTATAAACACGGTGTTCTTTACGTCTGCGACGCACTCCAAAACCGTTGTGA

L  A  I  I  F  V  P  Q  E  M  Q  T  L  R  E  V  L  A  T  L  -

GGGCTTAGGAGCGTCTGCTCTTGCCAATACCCTTGCTTTTGCCCATGGAAATGAAGTAAT
1561  ---------+---------+---------+---------+---------+---------+  1620
      CCCGAATCCTCGCAGACGAGAACGGTTATGGGAACGAAAACGGGTACCTTTACTTCATTA

G  L  G  A  S  A  L  A  N  T  L  A  F  A  H  G  N  E  V  I  -

TCCCACCATAATCAGGGCAAGAGCTATGGGATCAATGCAACCTTTGCTAATATAGCAGG
1621  ---------+---------+---------+---------+---------+---------+  1680
      AGGGTGGTATTAGTCCCGTTCTCGATACCCCTAGTTACGTTGGAAACGATTATATCGTCC

```
       AGCCCTGGCTCCCCTCATGATGATCCTAAGTGTGTATTCTCCACCCCTGCCCTGGATCAT
1681   ---------+---------+---------+---------+---------+---------+   1740
       TCGGGACCGAGGGGAGTACTACTAGGATTCACACATAAGAGGTGGGGACGGGACCTAGTA

A  L  A  P  L  M  M  I  L  S  V  Y  S  P  P  L  P  W  I  I  -

CTATGGAGTCTTCCCCTTCATCTCTGGCTTTGCTTTCCTCCTCCTTCCTGAAACCAGGAA
1741   ---------+---------+---------+---------+---------+---------+   1800
       GATACCTCAGAAGGGGAAGTAGAGACCGAAACGAAAGGAGGAGGAAGGACTTTGGTCCTT

Y  G  V  F  P  F  I  S  G  F  A  F  L  L  L  P  E  T  R  N  -

CAAGCCTCTGTTTGACACCATCCAGGATGAGAAAAATGAGAGAAAAGACCCCAGAGAACC
1801   ---------+---------+---------+---------+---------+---------+   1860
       GTTCGGAGACAAACTGTGGTAGGTCCTACTCTTTTTACTCTCTTTTCTGGGGTCTCTTGG

K  P  L  F  D  T  I  Q  D  E  K  N  E  R  K  D  P  R  E  P  -

AAAGCAAGAGGATCCGAGAGTGGAAGTGACGCAGTTTTAAGGAATTCCAGGAGCTGACTG
1861   ---------+---------+---------+---------+---------+---------+   1920
       TTTCGTTCTCCTAGGCTCTCACCTTCACTGCGTCAAAATTCCTTAAGGTCCTCGACTGAC

K  Q  E  D  P  R  V  E  V  T  Q  F  *

CCGATCAATGAGCCAGATGAAGGGAACAATCAGGACTATTCCTAGACACTAGCAAAA
1921   ---------+---------+---------+---------+---------+-------      1977
       GGCTAGTTACTCGGTCTACTTCCCTTGTTAGTCCTGATAAGGATCTGTGATCGTTTT
```

FIG. 5D

```
    CTCCTGATAGCAAAAGAACTGAGGAAGCTCTTTCCACTACGGCTGTATTGCACTGGTGAG
1   ------------+---------+---------+---------+---------+---------+  60
    GAGGACTATCGTTTTCTTGACTCCTTCGAGAAAGGTGATGCCGACATAACGTGACCACTC

TCCGGGCCCATGGATGAGAAATTGATGCGAGGATCAATACAAGCTTAATTTGAATTAATA
61  ------------+---------+---------+---------+---------+---------+  120
    AGGCCCGGGTACCTACTCTTTAACTACGCTCCTAGTTATGTTCGAATTAAACTTAATTAT

AAAGGAAATATTTTCTCCCTTTGAACTTATCTCCGTAAAGCCATTGTGCCTCCTCTTGGG
121 ------------+---------+---------+---------+---------+---------+  180
    TTTCCTTTATAAAAGAGGGAAACTTGAATAGAGGCATTTCGGTAACACGGAGGAGAACCC

GGTCACGTGTTCACAATCAATGGCCTTTGAGGAGCTCTTGAGTCAAGTTGGAGGCCTTGG
181 ------------+---------+---------+---------+---------+---------+  240
    CCAGTGCACAAGTGTTAGTTACCGGAAACTCCTCGAGAACTCAGTTCAACCTCCGGAACC

M  A  F  E  E  L  L  S  Q  V  G  G  L  G -

GAGATTTCAGATGCTTCATCTGGTTTTTATTCTTCCCTCTCTCATGTTATTAATCCCTCA
241 ------------+---------+---------+---------+---------+---------+  300
    CTCTAAAGTCTACGAAGTAGACCAAAAATAAGAAGGGAGAGAGTACAATAATTAGGGAGT

R  F  Q  M  L  H  L  V  F  I  L  P  S  L  M  L  L  I  P  H -

TATACTGCTAGAGAACTTTGCTGCAGCCATTCCTGGTCATCGTTGCTGGGTCCACATGCT
301 ------------+---------+---------+---------+---------+---------+  360
    ATATGACGATCTCTTGAAACGACGTCGGTAAGGACCAGTAGCAACGACCCAGGTGTACGA

I  L  L  E  N  F  A  A  A  I  P  G  H  R  C  W  V  H  M  L -

GGACAATAATACTGGATCTGGTAATGAAACTGGAATCCTCAGTGAAGATGCCCTCTTGAG
361 ------------+---------+---------+---------+---------+---------+  420
    CCTGTTATTATGACCTAGACCATTACTTTGACCTTAGGAGTCACTTCTACGGGAGAACTC

D  N  N  T  G  S  G  N  E  T  G  I  L  S  E  D  A  L  L  R -

AATCTCTATCCCACTAGACTCAAATCTGAGGCCAGAGAAGTGTCGTCGCTTTGTCCATCC
421 ------------+---------+---------+---------+---------+---------+  480
    TTAGAGATAGGGTGATCTGAGTTTAGACTCCGGTCTCTTCACAGCAGCGAAACAGGTAGG

I  S  I  P  L  D  S  N  L  R  P  E  K  C  R  R  F  V  H  P -

CCAGTGGCAGCTTCTTCACCTGAATGGGACTATCCACAGCACAAGTGAGGCAGACACAGA
481 ------------+---------+---------+---------+---------+---------+  540
    GGTCACCGTCGAAGAAGTGGACTTACCCTGATAGGTGTCGTGTTCACTCCGTCTGTGTCT

Q  W  Q  L  L  H  L  N  G  T  I  H  S  T  S  E  A  D  T  E -

ACCCTGTGTGGATGGCTGGGTATATGATCAAAGCTACTTCCCTTCGACCATTGTGACTAA
541 ------------+---------+---------+---------+---------+---------+  600
    TGGGACACACCTACCGACCCATATACTAGTTTCGATGAAGGGAAGCTGGTAACACTGATT

```
     GTGGGACCTGGTATGTGATTATCAGTCACTGAAATCAGTGGTTCAATTCCTACTTCTGAC
601  ------------+---------+---------+---------+---------+---------+  660
     CACCCTGGACCATACACTAATAGTCAGTGACTTTAGTCACCAAGTTAAGGATGAAGACTG

W  D  L  V  C  D  Y  Q  S  L  K  S  V  V  Q  F  L  L  L  T  -

TGGAATGCTGGTGGGAGGCATCATAGGTGGCCATGTCTCAGACAGGTTTGGGCGAAGATT
661  ------------+---------+---------+---------+---------+---------+  720
     ACCTTACGACCACCCTCCGTAGTATCCACCGGTACAGAGTCTGTCCAAACCCGCTTCTAA

G  M  L  V  G  G  I  I  G  G  H  V  S  D  R  F  G  R  R  F  -

TATTCTCAGATGGTGTTTGCTCCAGCTTGCCATTACTGACACCTGCGCTGCCTTCGCTCC
721  ------------+---------+---------+---------+---------+---------+  780
     ATAAGAGTCTACCACAAACGAGGTCGAACGGTAATGACTGTGGACGCGACGGAAGCGAGG

I  L  R  W  C  L  L  Q  L  A  I  T  D  T  C  A  A  F  A  P  -

CACCTTCCCTGTTTACTGTGTACTACGCTTCTTGGCAGGTTTTTCTTCCATGATCATTAT
781  ------------+---------+---------+---------+---------+---------+  840
     GTGGAAGGGACAAATGACACATGATGCGAAGAACCGTCCAAAAAGAAGGTACTAGTAATA

T  F  P  V  Y  C  V  L  R  F  L  A  G  F  S  S  M  I  I  -

ATCAAATAATTCTTTGCCCATTACTGAGTGGATAAGGCCCAACTCTAAAGCCCTGGTAGT
841  ------------+---------+---------+---------+---------+---------+  900
     TAGTTTATTAAGAAACGGGTAATGACTCACCTATTCCGGGTTGAGATTTCGGGACCATCA

S  N  N  S  L  P  I  T  E  W  I  R  P  N  S  K  A  L  V  V  -

AATATTGTCATCTGGTGCCCTTAGTATTGGACAGATAATCCTGGGAGGCTTGGCTTATGT
901  ------------+---------+---------+---------+---------+---------+  960
     TTATAACAGTAGACCACGGGAATCATAACCTGTCTATTAGGACCCTCCGAACCGAATACA

I  L  S  S  G  A  L  S  I  G  Q  I  I  L  G  G  L  A  Y  V  -

CTTCCGAGACTGGCAAACCCTGCACGTGGTGGCGTCAGTACCTTTCCTTGGCCTCCTTCT
961  ------------+---------+---------+---------+---------+---------+ 1020
     GAAGGCTCTGACCGTTTGGGACGTGCACCACCGCAGTCATGGAAAGGAACCGGAGGAAGA

F  R  D  W  Q  T  L  H  V  V  A  S  V  P  F  L  G  L  L  L  -

CCTTCAAAGGTGGCTGGTGGAATCTGCTCGGTGGTTGATAATCACCAATAAACTAGATGA
1021 ------------+---------+---------+---------+---------+---------+ 1080
     GGAAGTTTCCACCGACCACCTTAGACGAGCCACCAACTATTAGTGGTTATTTGATCTACT

L  Q  R  W  L  V  E  S  A  R  W  L  I  I  T  N  K  L  D  E  -

GGGCTTAAAGGCACTTAGAAAAGTTGCACGCACAAATGGAATAAAGAATGCTGAAGAAAC
1081 ------------+---------+---------+---------+---------+---------+ 1140
     CCCGAATTTCCGTGAATCTTTTCAACGTGCGTGTTTACCTTATTTCTTACGACTTCTTTG

```
     CCTGAACATAGAGGTTGTAAGATCCACCATGCAGGAGGAGCTGGATGCAGCACAGACCAA
1141 ---------+---------+---------+---------+---------+---------+ 1200
     GGACTTGTATCTCCAACATTCTAGGTGGTACGTCCTCCTCGACCTACGTCGTGTCTGGTT

L  N  I  E  V  V  R  S  T  M  Q  E  E  L  D  A  A  Q  T  K  -

AACTACTGTGTGTGACTTGTTCCGCAACCCCAGTATGCGTAAAAGGATCTGTATCCTGGT
1201 ---------+---------+---------+---------+---------+---------+ 1260
     TTGATGACACACACTGAACAAGGCGTTGGGGTCATACGCATTTTCCTAGACATAGGACCA

T  T  V  C  D  L  F  R  N  P  S  M  R  K  R  I  C  I  L  V  -

ATTTTTGAGATTTGCAAACACAATACCTTTTTATGGTACCATGGTCAATCTTCAGCATGT
1261 ---------+---------+---------+---------+---------+---------+ 1320
     TAAAAACTCTAAACGTTTGTGTTATGGAAAAATACCATGGTACCAGTTAGAAGTCGTACA

F  L  R  F  A  N  T  I  P  F  Y  G  T  M  V  N  L  Q  H  V  -

GGGGAGCAACATTTTCCTGTTGCAGGTACTTTATGGAGCTGTCGCTCTCATAGTTCGATG
1321 ---------+---------+---------+---------+---------+---------+ 1380
     CCCCTCGTTGTAAAAGGACAACGTCCATGAAATACCTCGACAGCGAGAGTATCAAGCTAC

G  S  N  I  F  L  L  Q  V  L  Y  G  A  V  A  L  I  V  R  C  -

TCTTGCTCTTTTGACACTAAATCATATGGGCCGTCGAATAAGCCAGATATTGTTCATGTT
1381 ---------+---------+---------+---------+---------+---------+ 1440
     AGAACGAGAAAACTGTGATTTAGTATACCCGGCAGCTTATTCGGTCTATAACAAGTACAA

L  A  L  L  T  L  N  H  M  G  R  R  I  S  Q  I  L  F  M  F  -

CCTGGTGGGCCTTTCCATTTTGGCCAACACGTTTGTGCCCAAAGAAATGCAGACCCTGCG
1441 ---------+---------+---------+---------+---------+---------+ 1500
     GGACCACCCGGAAAGGTAAAACCGGTTGTGCAAACACGGGTTTCTTTACGTCTGGGACGC

L  V  G  L  S  I  L  A  N  T  F  V  P  K  E  M  Q  T  L  R  -

TGTGGCTTTGGCATGTCTGGGAATCGGCTGTTCTGCTGCTACTTTTTCCAGTGTTGCTGT
1501 ---------+---------+---------+---------+---------+---------+ 1560
     ACACCGAAACCGTACAGACCCTTAGCCGACAAGACGACGATGAAAAAGGTCACAACGACA

V  A  L  A  C  L  G  I  G  C  S  A  A  T  F  S  S  V  A  V  -

TCACTTCATTGAACTCATCCCCACTGTTCTCAGGGCAAGAGCTTCAGGAATAGATTTAAC
1561 ---------+---------+---------+---------+---------+---------+ 1620
     AGTGAAGTAACTTGAGTAGGGGTGACAAGAGTCCCGTTCTCGAAGTCCTTATCTAAATTG

H  F  I  E  L  I  P  T  V  L  R  A  R  A  S  G  I  D  L  T  -

GGCTAGTAGGATTGGAGCAGCACTGGCTCCCCTCTTGATGACCTTAACGGTATTTTTTAC
1621 ---------+---------+---------+---------+---------+---------+ 1680
     CCGATCATCCTAACCTCGTCGTGACCGAGGGGAGAACTACTGGAATTGCCATAAAAAATG

```
         CACTTTGCCATGGATCATTTATGGAATCTTCCCCATCATTGGTGGCCTTATTGTCTTCCT
1681     ---------+---------+---------+---------+---------+---------+    1740
         GTGAAACGGTACCTAGTAAATACCTTAGAAGGGGTAGTAACCACCGGAATAACAGAAGGA

T  L  P  W  I  I  Y  G  I  F  P  I  I  G  G  L  I  V  F  L  -

CCTACCAGAAACCAAGAATCTGCCTTTGCCTGACACCATCAAGGATGTGGAAAATCAAAA
1741     ---------+---------+---------+---------+---------+---------+    1800
         GGATGGTCTTTGGTTCTTAGACGGAAACGGACTGTGGTAGTTCCTACACCTTTTAGTTTT

L  P  E  T  K  N  L  P  L  P  D  T  I  K  D  V  E  N  Q  K  -

AAAAAATCTCAAGGAAAAGGCATAAAAATGATTGCTACACAAAAGTGACCAAATTTTAAG
1801     ---------+---------+---------+---------+---------+---------+    1860
         TTTTTTAGAGTTCCTTTTCCGTATTTTTACTAACGATGTGTTTTCACTGGTTTAAAATTC

K  N  L  K  E  K  A  *

AAGCCTTCATGAGCTGATTGGTGGGGAAATTCAGAAAAAAAAATACAGGAAAAGAACACA
1861     ---------+---------+---------+---------+---------+---------+    1920
         TTCGGAAGTACTCGACTAACCACCCCTTTAAGTCTTTTTTTTTATGTCCTTTTCTTGTGT

CCAGAAGGGTTTTTTTCCCTACAACCAGCAAGAACATATATTAGATACATGAATCTCAAT
1921     ---------+---------+---------+---------+---------+---------+    1980
         GGTCTTCCCAAAAAAGGGATGTTGGTCGTTCTTGTATATAATCTATGTACTTAGAGTTA

TATAATTATGGCATTAATTTGCATTTTATTTCAAAATTAACTTGTGGGGACATGTAATCT
1981     ---------+---------+---------+---------+---------+---------+    2040
         ATATTAATACCGTAATTAAACGTAAAATAAAGTTTTAATTGAACACCCCTGTACATTAGA

CTTGAGCAATCTGATATTTTTGGGAAGTCCTTTAAAAAGTTACAAATTTATCAATAAATT
2041     ---------+---------+---------+---------+---------+---------+    2100
         GAACTCGTTAGACTATAAAAACCCTTCAGGAAATTTTTCAATGTTTAAATAGTTATTTAA

ACTAGTAGATAAGATGATTCAGAAACAAAGGAAAATCACAGAATTAGGATGTGGCTGGCT
2101     ---------+---------+---------+---------+---------+---------+    2160
         TGATCATCTATTCTACTAAGTCTTTGTTTCCTTTTAGTGTCTTAATCCTACACCGACCGA

TGGTGTATGAAGCACCATGTGATGAATTCATAAAGTTGCAAAAGTCAAAACAATACTGTA
2161     ---------+---------+---------+---------+---------+---------+    2220
         ACCACATACTTCGTGGTACACTACTTAAGTATTTCAACGTTTTCAGTTTTGTTATGACAT

CATGCAACCAGAAATCAAATTAAATCCAGAAATAGAGACCTATATAAATGCATTTAATAC
2221     ---------+---------+---------+---------+---------+---------+    2280
         GTACGTTGGTCTTTAGTTTAATTTAGGTCTTTATCTCTGGATATATTTACGTAAATTATG

ATGATACTTTTGACATATTAAGCCATTGGAAAACGGAAGGATTAGATACTTAAATAACAT
2281     ---------+---------+---------+---------+---------+---------+    2340
         TACTATGAAAACTGTATAATTCGGTAACCTTTTGCCTTCCTAATCTATGAATTTATTGTA

TGCTATCTCTTTGTAAATACAGTCACTAAATGATGTTAGTTACTTTTCCATGGTGGAATT
2341     ---------+---------+---------+---------+---------+---------+    2400
         ACGATAGAGAAACATTTATGTCAGTGATTTACTACAATCAATGAAAAGGTACCACCTTAA
```

*FIG. 6D*

```
       TTAATTACTTTTTCTTTGTAATTTTTCTCTCTGTATATTTTAAACAAATAGCTGGTATAG
2401   ---------+---------+---------+---------+---------+---------+  2460
       AATTAATGAAAAAGAAACATTAAAAAGAGAGACATATAAAATTTGTTTATCGACCATATC

TTTACAATATTATAAAGATATTGTTCAAATTGAAGGGCAAAGGCCAGGTTCAGCAATTTT
2461   ---------+---------+---------+---------+---------+---------+  2520
       AAATGTTATAATATTTCTATAACAAGTTTAACTTCCCGTTTCCGGTCCAAGTCGTTAAAA

CAAACTGTATGTACATTTAATAAAATAACTATAAATTAAAAAATTATATTTCAAATGATG
2521   ---------+---------+---------+---------+---------+---------+  2580
       GTTTGACATACATGTAAATTATTTTATTGATATTTAATTTTTTAATATAAAGTTTACTAC

TGACTAATAAATGAAAGTACATATAGTAGTAAAGTAATTTCAGGCAAACCTATATAACCA
2581   ---------+---------+---------+---------+---------+---------+  2640
       ACTGATTATTTACTTTCATGTATATCATCATTTCATTAAAGTCCGTTTGGATATATTGGT

AAATATAAACTTTCATTTTAAACAGCAAAAAAAAAAAAAAAAA
2641   ---------+---------+---------+---------+----  2684
       TTTATATTTGAAAGTAAAATTTGTCGTTTTTTTTTTTTTTTTTT
```

*FIG. 6E* hOAT1 hOAT2 hOAT3 hOAT4

… # ORGANIC ANION TRANSPORTER GENES AND PROTEINS

RELATED APPLICATIONS

This application claims the benefit of U.S. Ser. No. 60/143,771, entitled "Organic Anion Transporter Genes and Proteins," which was filed Jul. 12, 1999 and which is incorporated by reference herein in its entirety, including figures.

FIELD OF THE INVENTION

The present invention relates to specific proteins as well as recombinant versions of these proteins which are organic anion transporters. These proteins include human membrane proteins. preferentially found in kidney and liver cells. The present invention also relates to nucleotide sequences encoding these novel organic anion transporters. In another aspect, the present invention relates to methods for using these proteins as in vitro screening agents to identify substrates for the proteins and inhibitors which block transport activity. In yet another aspect, these proteins may be used in in vitro assays to predict drug pharmacokinetics, drug distribution and drug toxicity. The invention also discloses antibodies that specifically bind to these proteins and which may be used in diagnostic assays.

BACKGROUND OF THE INVENTION

The following describes certain relevant art, none of which is admitted to be prior art to the inventions described herein.

The liver and kidney are two organs that can extract a variety of organic anions from circulation, including endogenous compounds such as bile acids and bilirubin and xenobiotics such as sulfobromophthalein (BSP) and p-aminohippurate (PAH). The liver and kidney thus have the critical functions of bile secretion, detoxification, and drug elimination. Since the cell membrane represents a hydrophobic barrier that prevents influx of charged or hydrophilic molecules, hepatocytes and kidney epithelial cells express proteins on their basolateral membranes to facilitate transport of organic anions into the cell. The liver and kidney contain membrane proteins that transport very specific compounds such as taurocholic acid or prostaglandins. However, they also have proteins that exhibit a wider substrate specificity. Recently, transporters of the latter type have been cloned from rat liver and kidney. One such protein is called the organic anion transporting polypeptide, oatp (Jacquemin et al. (1994) *PNAS* 91:133–37). This protein belongs to a family of related transporters, members of which consists of oatp1, oatp2, oatp3, and prostaglandin transporters. These proteins share homology at the amino acid level (Noe et al. (1997) *PNAS* 94: 10346–50; Kanai et al. (1995) *Science* 268: 866–69; Abe et al. (1998) *J. Biol. Chem.* 273: 22395–401). When expressed in Xenopus oocytes or in mammalian cells, members of the oatp family were shown to transport many types of organic anions including taurocholic acid, BSP, and conjugated steroid hormones. The related prostaglandin transporters show high affinity transport of prostaglandins.

Shortly after the cloning of oatp1, members of another organic anion transporter family, OAT1 and OAT2, were isolated from rat kidney and liver, respectively (Sekine et al. (1997) *J. Biol. Chem* 272: 18526–29; Sekine et al. (1998) *FEBS Letters* 429: 179–82). Rat OAT1 and OAT2 are homologous to each other but show no significant homology to members of the oatp family. However, they show some homology to the family of organic cation transporters (OCTs), suggesting that these two families of proteins share a common origin. Rat OAT1 and OAT2 can transport many different organic anions. OAT1, when expressed in oocytes, can transport p-aminohippurate (PAH), methotrexate, and glutarate. OAT1 is most likely the molecular entity responsible for the classical p-aminohippurate/α-ketoglutarate exchanger found in the kidney proximal tubule. OAT2, expressed predominantly in the liver, has been shown to transport organic anions such as salicylate, methotrexate, and α-ketoglutarate. Therefore, OAT1 and OAT2 belong to yet another family of multi-specific organic anion transporters distinct from the oatp family.

SUMMARY OF THE INVENTION

The present invention is directed to a group of polypeptides, preferentially expressed in the liver and kidneys of humans and which have activity as organic anion transporters. We refer to these polypeptides as "human organic anion transporters" or "hOAT polypeptides". These proteins and their properties are described in detail below.

The invention also concerns, nucleic acids encoding hOAT polypeptides, cells, tissues and animals containing such nucleic acids, antibodies to the polypeptides, assays utilizing the polypeptides, and methods relating to all of the foregoing.

A first aspect of the invention features an isolated, enriched, or purified nucleic acid molecule encoding an hOAT polypeptide or encoding a fragment of an hOAT polypeptide.

In preferred embodiments the isolated nucleic acid comprises a nucleic acid sequence set forth in SEQ ID NO:1, SEQ ID NO:2, SEQ ID NO:3, SEQ ID NO:4, SEQ ID NO:5, SEQ ID NO:6, or a functional derivative thereof, a nucleic acid sequence that hybridizes to the nucleic acid sequence set forth in SEQ ID NO:1, SEQ ID NO:2, SEQ ID NO:3, SEQ ID NO:4, SEQ ID NO:5, SEQ ID NO:6, or a functional derivative thereof.

The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer. Preferably, the nucleic acid is isolated from mammalian kidney or brain, most preferably from liver.

Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

In another preferred embodiment, the nucleic acid molecules of the invention comprise nucleotide sequences that (a) have the nucleic acid sequences set forth in SEQ ID NO:1, SEQ ID NO:2, SEQ ID NO:3, SEQ ID NO:4, SEQ ID NO:5, SEQ ID NO:6, or a functional derivative thereof, or encode polypeptides having the full-length amino acid sequences set forth in SEQ ID NO:7, SEQ ID NO:8; SEQ ID NO:9, SEQ ID NO:10, SEQ ID NO:11, SEQ ID NO:12, or a functional derivative thereof, (b) is the complement of the nucleotide sequence of (a); (c) hybridizes under highly stringent conditions to the nucleotide molecules of (a) and encodes a naturally occurring hOAT polypeptide; (d) encodes an hOAT polypeptide having the full-length amino acid sequence of the sequence set forth in SEQ ID NO:7, SEQ ID NO:8, SEQ ID NO:9, SEQ ID NO:10, SEQ ID NO:11, or SEQ ID NO:12 except that it lacks one or more of the domains selected from the group consisting of an extracellular domain, a transmembrane domain, and an intracellular domain; or (e) is the complement of the nucleotide sequence of (d).

The nucleic acid molecules of the invention are isolated, enriched, or purified preferably from a mammal, more preferably from a human.

Hybridization techniques may be used to isolate a nucleic acid molecule of interest. Various low or high stringency hybridization conditions may be used depending upon the specificity and selectivity desired. Stringency is controlled by varying salt or denaturant concentrations. Highly stringent conditions may mean conditions that are at least as stringent as the following: hybridization in 50% formamide, 5×SSC, 50 mM $NaH_3PO_4$, pH 6.8, 0.5% SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C. Those skilled in the art will recognize how such conditions can be varied to vary specificity and selectivity.

Particularly preferred embodiments of this aspect of the invention are naturally or non-naturally occurring variants of the nucleic acids of the invention. Among variants in this regard are variants that differ from the aforementioned nucleic acid molecules by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Such nucleic acid molecules are identifiable as being able to hybridize to or which are at least about 60–65% percent identical, preferably at least about 70–75% percent identical, more preferably at least about 80–83% percent identical, and even more preferably at least about 87–95% percent identical to the nucleic acid molecules shown in SEQ ID NO:1, SEQ ID NO:2, SEQ ID NO:3, SEQ ID NO:4, SEQ ID NO:5 or SEQ ID NO:6.

Among the particularly preferred embodiments of the invention in this regard are nucleic acid molecules encoding polypeptides having the amino acid sequences set forth in SEQ ID NO:7, SEQ ID NO:8, SEQ ID NO:9, SEQ ID NO:10, SEQ ID NO:11, SEQ ID NO:12; variants, analogs, derivatives and fragments thereof, and fragments of the variants, analogs and derivatives.

Further particularly preferred in this regard are nucleic acid molecules encoding OAT variants, analogs, derivatives and fragments, and variants, analogs and derivatives of the fragments, which have the amino acid sequence for the hOAT polypeptides of SEQ ID NO:7, SEQ ID NO:8, SEQ ID NO:9, SEQ ID NO:10, SEQ ID NO:11, SEQ ID NO:12 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the OAT polypeptides. Also especially preferred in this regard are conservative substitutions. In one embodiment, the polypeptide encoded by the nucleic acid molecule is at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more identical to the amino acid sequence of SEQ ID NO:7, SEQ ID NO:8, SEQ ID NO:9, SEQ ID NO:10, SEQ ID NO:11, or SEQ ID NO:12.

In still another embodiment, the nucleic acid molecule encodes a naturally occurring variant of the polypeptide of SEQ ID NO:7, SEQ ID NO:8, SEQ ID NO:9, SEQ ID NO:10, SEQ ID NO:11, or SEQ ID NO:12 and hybridizes under stringent conditions to a nucleic acid molecule comprising SEQ ID NO:1, SEQ ID NO:2, SEQ ID NO:3, SEQ ID NO:4, SEQ ID NO:5 or SEQ ID NO:6, respectively.

Further preferred embodiments are variants of the herein described nucleic acid molecules in which the transporting activity of the polypeptides is altered. Such alterations can result in either increased, or decreased transport of substrates recognized by hOAT polypeptides. Further, variants can be made that result in OAT polypeptides which are no longer responsive to cellular signals, for example, protein kinase C deactivation of transport.

Especially preferred are nucleic acid molecules encoding OATs which are expressed on the basolateral (sinusoid) membrane of hepatocyte cells.

Included in the invention are all possible nucleic acid sequences that encode the amino acid sequences of the hOAT polypeptides of the invention. As it is recognized that alternate codons will encode the same amino acid for most amino acids due to the degeneracy of the genetic code, the sequences of this aspect includes nucleic acid sequences utilizing such alternate codon usage for one or more codons of a coding sequence. For example, all four nucleic acid sequences GCT, GCC, GCA, and GCG encode the amino acid, alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified (e.g., a nucleic acid sequence from an hOAT as specified above) to form a second nucleic acid sequence encoding the same polypeptide as encoded by the first nucleic acid sequence using routine procedures and without undue experimentation. Thus, all possible nucleic acid sequences that encode the amino acid sequences of the hOAT polypeptides of the invention are included in the present invention and are described, as if all were written out in full, taking into account the codon usage.

The alternate codon descriptions are available in common textbooks, for example, Stryer, BIOCHEMISTRY $3^{rd}$ ed., and Lehninger, BIOCHEMISTRY $3^{rd}$ ed. Codon preference tables for various types of organisms are available in the literature. Because of the number of sequence variations involving alternate codon usage, for the sake of brevity, individual sequences are not separately listed herein. Instead the alternate sequences are described by reference to the natural sequence with replacement of one or more (up to all) of the degenerate codons with alternate codons from the alternate codon table, preferably with selection according to preferred codon usage for the normal host organism or a host organism in which a sequence is intended to be expressed. Those skilled in the art also understand how to alter the alternate codons to be used for expression in organisms where certain codons code differently than shown in the "universal" codon table.

In a second aspect, the invention relates to a nucleic acid vector comprising a nucleic acid molecule encoding an hOAT polypeptide and a promoter element effective to initiate transcription in a host cell.

Those skilled in the art would recognize that a nucleic acid vector can contain many other nucleic acid elements besides the promoter element and the hOAT nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. These methods involve a variety of techniques, such as treating the cells with high concentrations of salt, an electric field, or detergent, to render the host cell outer membrane or wall permeable to nucleic acid molecules of interest.

In a third aspect, the invention features a nucleic acid probe for the detection of a nucleic acid encoding an hOAT polypeptide, fragment or analogue in a sample. The nucleic acid probe contains nucleotides that will hybridize specifically to a sequence of at least 14 contiguous nucleotides set forth in SEQ ID NO:1, SEQ ID NO:2, SEQ ID NO:3, SEQ ID NO:4, SEQ ID. NO:5, or SEQ ID NO:6, or a functional derivative thereof. The probe is preferably at least 14 or more bases in length and selected to hybridize specifically to a unique region of an hOAT encoding nucleic acid.

In preferred embodiments, the nucleic acid probe hybridizes to at least 14 nucleotides of a nucleic acid encoding the full-length sequence set forth in SEQ ID NO:7, SEQ ID NO:8, SEQ ID NO:9, SEQ ID NO:10, SEQ ID NO:11, SEQ ID NO:12, or a functional derivative thereof. Various low or high stringency hybridization conditions may be used depending upon the specificity and selectivity desired. Under highly stringent hybridization conditions, only highly complementary nucleic acid sequences hybridize. Preferably, such conditions prevent hybridization of nucleic acids having 1 or 2 mismatches out of 20 contiguous nucleotides.

In another preferred embodiment, the nucleic acid is an isolated conserved or unique region, for example, those useful for the design of hybridization probes to facilitate identification and cloning of additional polypeptides, or for the design of PCR probes to facilitate amplification or cloning of additional polypeptides. Such a nucleic acid may contain additional sequences in addition to the conserved or unique region, preferably 10–20 additional nucleotides on each side of the conserved or unique region, more preferably 30–40 additional nucleotides, and most preferably 75–100 additional nucleotides.

Methods for using the probes include detecting the presence or amount of hOAT polypeptide RNA in a sample by contacting the sample with a nucleic acid probe under conditions such that hybridization occurs and detecting the presence or amount of the probe bound to hOAT polypeptide RNA. The nucleic acid duplex formed between the probe and a nucleic acid sequence coding for an hOAT polypeptide may be used in the identification of the sequence of the nucleic acid detected (for example see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container having disposed therein a nucleic acid probe.

Another feature of the invention is a nucleic acid molecule as set forth in SEQ ID NO:1, SEQ ID NO:2, SEQ ID NO:3, SEQ ID NO:4, SEQ ID NO:5, or SEQ ID NO:6, or fragments thereof, comprising one or more regions that encode an hOAT polypeptide or an hOAT domain polypeptide, where the hOAT polypeptide or the hOAT domain polypeptide is fused to a non-hOAT polypeptide or amino-terminal tag. Possible non-hOAT polypeptide or amino-terminal tag fusion partners include, for example, but are not limited to, glutathione-S-transferase (GST)-fusion proteins, green fluorescent protein (GFP) and fusions with histidine residues as described by Janknecht et al., 1991, Proc. Natl. Sci. USA 88:8972–8976.

The invention also features recombinant nucleic acid, preferably in a cell or an organism. The recombinant nucleic acid may contain a sequence set forth in SEQ ID NO:1, SEQ ID NO:2, SEQ ID NO:3, SEQ ID NO:4, SEQ ID NO:5, or SEQ ID NO:6 or a functional derivative thereof and a vector or a promoter effective to initiate transcription in a host cell. The recombinant nucleic acid can alternatively contain a transcriptional initiation region functional in a cell, a sequence complimentary to an RNA sequence encoding an hOAT polypeptide and a transcriptional termination region functional in a cell.

Another aspect of the invention relates to a recombinant cell or tissue comprising a nucleic acid molecule encoding an hOAT polypeptide or hOAT polypeptide fragment. The recombinant cell may comprise a nucleic acid molecule encoding an hOAT polypeptide; an hOAT domain polypeptide; an hOAT polypeptide fragment or an hOAT polypeptide or polypeptide fragment fused to a non-hOAT polypeptide. The recombinant cell can harbor a nucleic acid vector that is extragenomic or intragenomic.

Extragenomic vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell.

Multiple intragenomic vectors are available to those skilled in the art and contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

A new combination of genes or nucleic acid molecules can be introduced into an organism using a wide array of nucleic acid manipulation techniques available to those skilled in the art.

In yet another aspect, the invention features an isolated, enriched, or purified hOAT polypeptide.

It is also advantageous for some purposes that an amino acid sequence be in purified form. Purification of at least one order of magnitude, preferably two or three orders, and more preferably four or five orders of magnitude is expressly contemplated. The substance is preferably free of contamination at a functionally significant level, for example 90%, 95%, or 99% pure. The hOAT polypeptides, or fragments thereof, of the present invention are preferably isolated, purified, or enriched from a mammal or a mammalian cell. The mammal is as defined herein and preferably is a mouse, and most preferably is a human. These polypeptides may be isolated, purified, or enriched from a cell that comprises an endogenous nucleic acid molecule that encodes the polypeptide, or from a cell that is transformed with a nucleic acid molecule that encodes the polypeptide. The polypeptide may also be chemically synthesized. Procedures for obtaining polypeptides using the above methods are well known to those skilled in the art.

The polypeptides of the invention comprise an amino acid sequence having (a) the full-length amino acid sequence encoded by the nucleic acid sequences set forth in SEQ ID NO:1, SEQ ID NO:2, SEQ ID NO:3, SEQ ID NO:4, SEQ ID NO:5, SEQ ID NO:6, or functional derivatives thereof, or the amino acid sequences set forth in SEQ ID NO:7, SEQ ID NO:8; SEQ ID NO:9, SEQ ID NO:10, SEQ ID NO:11, SEQ ID NO:12, or functional derivatives thereof.

The invention also features an isolated, enriched, or purified hOAT polypeptide fragment.

Examples of polypeptide fragments include hOAT domains, and hOAT-specific epitopes. Such fragments may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein can be used as antigens for the production of hOAT-specific antibodies, or used as competitors of substrates for hOAT polypeptides. It is understood that such fragments may retain one or more characterizing portions of the native complex. Examples of such retained characteristics include: transporting activity; substrate specificity; interaction with other molecules in the intact cell; regulatory functions; or binding with an antibody specific for the native complex, or an epitope thereof.

Well-known examples of domains are the SH2 (Src Homology 2) domain (Sadowski, et al., (1986) *Mol. Cell. Biol.* 6:4396; Pawson and Schlessinger, (1993) *Curr. Biol.* 3:434), the SH3 domain (Mayer, et al., (1988) *Nature* 332:272; Pawson and Schlessinger, (1993) *Curr. Biol.* 3:434), and pleckstrin (PH) domain (Ponting, (1996) *TIBS* 21:245; Hasiam, et al., (1993) *Nature* 363:309), all of which are domains that mediate protein:protein interaction, and the kinase catalytic domain (Hanks and Hunter, (1995) *FASEB J* 9:576–595). The relative homology is at least 20%, more preferably at least 30% and most preferably at least 35%. Computer programs designed to detect such homologies are well known in the art.

Comparisons between the sequences of two or more polynucleotides or polypeptides can be performed using the local homology algorithm of Smith and Waterman, (1981) *Adv. Appl. Math.* 2:482, by the homology alignment algorithm of Needleman and Wunsch, (1970) *J. Mol. Biol.* 48:443, or the method of Pearson and Lipman, (1988) *PNAS* 85:2444. Computer programs implementing these methods can be used and include, BLAST, GAP, BESTFIT, FASTA, and TFASTA which are offered in the Wisconsin Genetics Software Package, Genetics Computer Group, 575 Science Dr., Madison, Wis.

Protein motifs can be identified using computer programs readily available to those skilled in the art. One such computer program is offered by the Institute for Chemical Research at Kyoto University. The Kyoto computer program is offered at the following world wide web site (motif.genome.ad.jp/).

Protein topology, such as the orientation and location of transmembrane helixes can also be identified using readily available computer programs. One such program is Top-Pred2 offered by Stockholm University and offered at the following world wide web site (biokemi.su.se/~server/toppred2/).

Another aspect of the invention features an isolated, enriched or purified hOAT polypeptide analog.

The hOAT polypeptide analogs of the present invention preferably have a substantially similar biological activity to the proteins encoded by the full-length nucleic acid sequence set forth in SEQ ID NO:1, SEQ ID NO:2, SEQ ID NO:3, SEQ ID NO:4, SEQ ID NO:5, or SEQ ID NO:6, or the amino acid sequence set forth in SEQ ID NO:7, or SEQ ID NO:8; SEQ ID NO:9, SEQ ID NO:10, SEQ ID NO:11, or SEQ ID NO:12.

A sequence that is substantially similar will preferably have at least 85% identity (more preferably at least 90% and most preferably 95–100%) to the amino acid sequence encoded by the nucleic acid sequence set forth in SEQ ID NO:1, SEQ ID NO:2, SEQ. ID NO:3, SEQ ID NO:4, SEQ ID NO:5, or SEQ ID NO:6, or the amino acid sequence set forth in SEQ ID NO:7, SEQ ID NO:8; SEQ ID NO:9, SEQ ID NO:10, SEQ ID NO:11, or SEQ ID NO:12.

An hOAT polypeptide analog will retain some useful function such as, for example, substrate binding, transport activity, or the ability to bind to an hOAT specific antibody (as defined below). The hOAT polypeptide analog may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such analogs having added, substituted and/or additional amino acids retain one or more characterizing portions of the native hOAT polypeptides.

Examples of hOAT polypeptides analogs include, but are not limited to, (1) chimeric proteins which comprise a portion of an hOAT polypeptide sequence fused to a non-hOAT polypeptide sequence, for example, a polypeptide sequence of glutathione-S-transferase, (2) hOAT polypeptides lacking a specific domain, for example, the protein kinase C domain, (3) epitope-tagged hOAT polypeptides or fragments for immuno detection or purification and (4) hOAT proteins having a point mutation.

Human OAT polypeptide analogs with deleted, inserted and/or substituted amino acid residues may be prepared using standard techniques well known to those of ordinary skill in the art. For example, the modified components of the analogs may be produced using site-directed mutagenesis techniques (as exemplified by Adelman et al., (1983) *DNA* 2:183) wherein nucleotides in the DNA coding the sequence are modified such that a modified coding sequence is produced, and thereafter expressing this recombinant DNA in a prokaryotic or eukaryotic host cell, using techniques such as those described above. Alternatively, proteins with amino acid deletions, insertions and/or substitutions may be conveniently prepared by direct chemical synthesis, using methods well known in the art. The analogs of the hOAT polypeptides may exhibit the same qualitative biological activity as the hOAT polypeptides themselves.

In another aspect, the invention features an antibody (e.g., a monoclonal or polyclonal antibody) having specific-binding affinity to an hOAT polypeptide or hOAT polypeptide analog or fragment.

Antibodies having specific-binding affinity to an hOAT polypeptide may be used in methods for detecting the presence and/or amount of an hOAT polypeptide in a sample by contacting the sample with the antibody under conditions such that an immunocomplex forms and detecting the presence and/or amount of the antibody conjugated to the hOAT polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

For the production of polyclonal antibodies, various host animals may be immunized by injection with the antigen. Various adjuvants may be used to increase the immunological response, depending on the host species.

Monoclonal antibodies may be obtained by any technique which provides for the production of antibody molecules by continuous cell lines in culture. Monoclonal antibodies may be obtained by methods known to those skilled in the art. See, for example, Kohler, et al., (1975) *Nature* 256:495–497, and U.S. Pat. No. 4,376,110 issued Mar. 8, 1983, to David et al.

Still further, the invention features a hybridoma which produces an antibody having specific-binding affinity to an hOAT polypeptide.

In preferred embodiments, the hOAT antibody comprises a sequence of amino acids that is able to specifically bind an hOAT polypeptide.

The invention features a method for identifying human cells containing an hOAT polypeptide or a related sequence. The method involves identifying the novel polypeptide in human cells using techniques that are routine and standard in the art, such as those described herein for identifying hOAT (eg., cloning, Southern or Northern blot analysis, Western blot analysis, immunoassay, in situ hybridization, PCR amplification, etc.).

The invention also features methods of screening cells for natural-binding partners of hOAT polypeptides. Binding partners include modulators and downstream signaling molecules such as adaptor proteins and may be identified by techniques well known in the art such as co-immunoprecipitation or by using, for example, a two-hybrid screen. (Fields and Song, U.S. Pat. No. 5,283,173, issued Feb. 1, 1994, and incorporated by reference herein). The present invention also features the purified, isolated or enriched versions of the polypeptides identified by the methods described above.

The invention provides methods for screening compounds for their ability to inhibit, or modulate the biological activity of the human organic anion transporter molecules of the invention. In preferred embodiments, cells expressing an hOAT polypeptide, including recombinant expression constructs of the invention, are contacted with a compound, and transport activity is assayed. In especially preferred embodiments, competition assays, using known human organic anion transporter substrates, such as p-aminohippurate, are used to test the ability of a screened compound to interfere (compete) with the uptake of a known substrate of an hOAT polypeptide. Additional preferred embodiments comprise quantitative analyses of such effects.

The present invention is also useful for the detection of substrates, analogues of substrates, inhibitors and modulators, heretofore known or unknown, for the transporters of the invention, either naturally occurring or embodied as a drug. In preferred embodiments, such substrates, analogues, or modulators may be detected in blood, saliva, semen, cerebrospinal fluid, plasma, lymph, vitreous humor, or any other bodily fluid. In additional preferred embodiments, the invention provides methods for detecting and identifying substrates, analogues of substrates, or modulators that preferentially affect either the uptake function or the efflux function of the transporters of the invention.

One method for identifying a substance capable of modulating an hOAT polypeptide activity comprises the steps of (a) contacting an hOAT polypeptide with a test substance; and (b) determining whether the substance alters the transporting activity of said polypeptide.

Another method of identifying substances capable of modulating the function of an hOAT polypeptide comprises the following steps: (a) expressing an hOAT polypeptide in cells; (b) adding a compound to the cells; and (c) monitoring the transporting activity of the hOAT.

A method of identifying substrates or inhibitors of hOAT polypeptides comprises the following steps: (a) adding a test substrate to a cell line expressing an hOAT polypeptide; and (b) measuring the intracellular concentration of the test substrate.

A second method of identifying substrates or inhibitors of hOAT polypeptides comprises the following steps: (a) adding a test substrate to a cell line expressing an hOAT polypeptide; (b) adding a substrate known to be transported by said hOAT polypeptides; (c) measuring whether said test substrate competes with the uptake of the known substrate.

Another method of identifying substrates of an hOAT polypeptide comprises the following steps: (a) attaching a fluorescent compound onto a test compound; (b) adding said compound to a cell line expressing an hOAT polypeptide; and (c) monitoring whether said fluorescent compound is taken into said cell line through the use of fluorescent microscopy or any other method which can detect fluorescence.

In a preferred embodiment, high-throughput screening employing 96-well plates and a microtiter® fluorescence detection system is used to detect potential modulators, substrates, analogues of substrates and inhibitors of hOAT polypeptides which can compete with binding or transport of fluorescent compounds known to bind or be transported by hOAT polypeptides.

In yet another embodiment, uptake of a test substrate by an hOAT expressing cell line is measured using knowledge of an hOAT's antiporter activity. Uptake is measured by monitoring efflux of an accompanying antiporter molecule. Efflux of the antiporter molecule can be detected using techniques known to those skilled in the art, for example, radiolabeling of the effluxed molecule and measurement using a scintillation counter. Measurement of antiporter efflux,is also amenable to high-throughput screening.

A still further aspect of the invention is the identification of substrates, analogues of substrates, inhibitors, or modulators that affect the pharmacokinetics of drugs and compounds transported by hOAT polypeptides. Substances which decrease the transporting activity of hOAT polypeptides are useful for increasing the half-life in the body of drugs and compounds excreted via human organic anion transporters.

Yet, another aspect of the invention involves substrates, and modulators, which increase the transporting activity of an hOAT. Such substances are advantageous for increasing the delivery of a drug or compound, which is transported by an hOAT, to a target organ such as kidney or liver. For example, a modulator which increases the transporting activity of hOAT1 would increase the delivery of PAH or other drugs or compounds transported by hOAT1 to the kidney.

A last aspect of the invention features a cultured cell line which stably expresses an hOAT polypeptide. Such cell lines are useful for identifying substrates which are transported by hOAT polypeptides, inhibitors of hOAT polypeptides and for identifying modulators of hOAT polypeptides. Further, a panel of cells stably expressing hOAT polypeptides will be useful in studying the pharmacokinetics of various drugs and compounds. Preferably, the expression of an hOAT polypeptide in such cell lines is under the control of an inducible promoter. More preferably, said inducible promoter has a very low basal level of expression in such cell lines and high expression when induced.

A cell line stably expressing an hOAT polypeptide is useful for designing substrates which can be transported by an hOAT polypeptide at either an increased or a decreased rate. Decreasing the rate of transport can increase the effectiveness of some medicinals by making their clearance from the body occur more slowly.

Cell lines stably expressing hOAT polypeptides are also useful for the identification and development of drugs or compounds targeted to a particular organ. For example, drugs or compounds identified as substrates of hOAT1 would be good candidates for treating diseases of the kidneys whereas those identified as substrates of hOAT2 would be good candidates for treating diseases of the liver.

The OAT expressing cell lines are also useful for identifying potentially toxic compounds or drugs. For example, newly discovered or modified drugs belonging to a class of drugs known to be toxic to certain organs, e.g., kidney can be tested for transport against the panel of cells expressing human OAT1 or hOAT3 polypeptides. If the new drug or compound is transported by hOAT1 expressing cells, the new drug or compound may also be toxic to the kidney. However, if the new drug or compound, belonging to a class known to be toxic, is not transported by hOAT1 or hOAT3 expressing cells than the new drug or compound would be expected to be less toxic to the kidney than the parent class of drugs or compounds.

A preferred embodiment includes the identification of toxic compounds which are substrates of hOATs, and which can be used to treat diseases of organs or tissues that express hOATs. For example, toxic compounds found to be transported by hOAT1 or hOAT3 would have potential use as anti-cancer drugs to treat cancers of the kidney.

The methods of the present invention can utilize any of the molecules disclosed in the invention. These molecules include nucleic acid molecules encoding hOAT polypeptides, nucleic acid vectors, recombinant cells, polypeptides, or antibodies described herein.

The summary of the invention described above is non-limiting and other features and advantages of the invention will be apparent from the following detailed description, and from the claims.

Definitions

By "isolated" in reference to nucleic acid it is meant a polymer preferably consisting of 14 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of nucleotide material naturally associated with it and thus is meant to be distinguished from isolated chromosomes.

By the use of the term "enriched" in reference to nucleic acid it is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/mL). The term is also chosen to distinguish clones already in existence which may encode an hOAT polypeptide but which have not been isolated from other clones in a library of clones. Thus, the term covers clones encoding an hOAT polypeptide which are isolated from other non-hOAT clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to cDNA. The probe hybridizes (binds) to complementary sequences of cDNA.

The term "complementary" describes two nucleotides that can form multiple favorable interactions with one another.

For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybridization conditions, only highly complementary nucleic acid sequences hybridize. Preferably, such conditions prevent hybridization of nucleic acids having one or two mismatches out of 20 contiguous nucleotides.

By "conserved nucleic acid regions", it is meant regions present on two or more nucleic acids encoding an hOAT polypeptide, to which a particular nucleic acid sequence can hybridize under lower stringency conditions. Examples of lower stringency conditions suitable for screening for nucleic acids encoding hOAT polypeptides are provided in Abe, et al. (1992) *J. Biol. Chem.* 19:13361 (hereby incorporated by reference herein in its entirety, including any drawings). Preferably, conserved regions differ by no more than 5 out of 20 contiguous nucleotides.

By "unique nucleic acid region" is meant a sequence present in a full-length nucleic acid coding for an hOAT polypeptide that is not present in a sequence coding for any other known naturally occurring polypeptide. Such regions preferably comprise 12 or more contiguous nucleotides present in the full-length nucleic acid encoding an hOAT polypeptide. In particular, a unique nucleic acid region is preferably of human origin.

The term "nucleic acid vector" relates to a single or double stranded circular nucleic acid molecule that can be transfected or transformed into cells and replicate independently or within the host cell genome.

The terms "transformation" and "transfection" refer to methods of inserting an expression construct into a cellular organism.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the hOAT polypeptide nucleic acid molecule such that the latter is transcribed into mRNA. Host cell machinery then translates mRNA into a polypeptide.

By an "hOAT polypeptide" is meant the full-length amino acid sequence of SEQ ID NO:7, SEQ ID NO:8, SEQ ID NO:9, SEQ ID NO:10, SEQ ID NO:11, SEQ ID NO:12, or a functional derivative thereof.

The term "recombinant cell" refers to a cell that has been altered to contain a new combination of genes or nucleic acid molecules.

The term "recombinant organism" refers to an organism that has a new combination of genes or nucleic acid molecules.

The term "organism" relates to any living being comprised of at least one cell. An organism can be as simple as one eukaryotic cell or as complex as a mammal. Therefore, a recombinant organism can also be a recombinant cell, which may be a eukaryotic or a prokaryotic organism.

By "recombinant hOAT polypeptide" it is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria, while eukaryotes are represented by yeast, invertebrates, and vertebrates.

The term "extragenomic" refers to a nucleic acid vector which does not insert into the cell genome. Thus, these vectors replicate independently of the host genome and do not recombine with or integrate into the genome.

The term "intragenomic" defines a nucleic acid construct that is incorporated within the cell genome.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acid sequences present in the cells or solution of interest than in normal or diseased cells or in the cells from which the sequence was taken. This could be caused by a preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased.

The term "significant" here is used to indicate that the level of increase is useful to the person making such an increase, and generally means an increase relative to other amino acid sequences of about at least 2 fold, more preferably at least 5 to 10 fold or even more. The term also does not imply that there are no amino acid sequences from other sources. The other source amino acid sequences may, for example, comprise amino acid sequences encoded by a yeast or bacterial genome, or a cloning vector such as pUC19. The term is meant to cover only those situations in which a person has intervened to elevate the proportion of the desired amino acid sequences.

The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/mL).

By "an hOAT polypeptide fragment" it is meant an amino acid sequence that is less than the full-length hOAT amino acid sequences (and which excludes the listed EST sequences) encoded by the nucleic acid sequence set forth in SEQ ID NO:1 (excluding EST clone R25797), SEQ ID NO:2 (excluding EST clone A1016020), SEQ ID NO:3 (excluding EST clone A 1016020), SEQ ID NO:4 (excluding EST clone H41333), SEQ ID NO:5, or SEQ ID NO:6 (excluding EST clone AA705512) or the amino acid sequence (excluding the amino acids encoded by the EST clones previously listed set forth in SEQ ID NO:7, SEQ ID NO:8; SEQ ID NO:9, SEQ ID NO:10, SEQ ID NO:11, or SEQ ID NO:12. Thus, the term "fragment" is used to indicate a polypeptide derived from the amino acid sequence of the hOAT polypeptides, of the complexes having a length less than the full-length polypeptide from which it has been derived.

By "an hOAT domain" it is meant a portion of the hOAT polypeptide having homology to amino acid sequences from one or more known proteins wherein the sequence predicts some common function, interaction or activity.

By "hOAT polypeptide analog" it is meant an amino acid sequence substantially similar to the sequence encoded by the nucleic acid sequence set forth in SEQ ID NO:1, SEQ ID NO:2, SEQ ID NO:3, SEQ ID NO:4, SEQ ID NO:5, or SEQ ID NO:6, or the amino acid sequence set forth in SEQ ID NO:7, or SEQ ID NO:8; SEQ ID NO:9, SEQ ID NO:10, SEQ ID NO:11, or SEQ ID NO:12.

By "biological activity" it is meant an activity of the hOAT polypeptides in a cell. The biological activity of the hOAT polypeptides is related to some of the activities of the cell which include, but are not limited to, transport (uptake or excretion of a substrate from a cell), cell proliferation, mitogenesis, metastasis, tumor escape, cell adhesion, transformation, or apoptosis.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

An hOAT polypeptide analog may differ from the native sequence of an hOAT polypeptide in that one or more amino acids have been changed, added or deleted. Changes in amino acids may be conservative or non-conservative. By "conservative" it is meant the substitution of an amino acid for one with similar properties such as charge, hydrophobicity, structure, etc.

By "hOAT-specific epitope" it is meant a sequence of amino acids that is both antigenic and unique to hOAT.

By "specific-binding affinity" is meant that the antibody binds to target (hOAT) polypeptides with greater affinity than it binds to other polypeptides under specified conditions.

The term "polyclonal" refers to antibodies that are heterogenous populations of antibody molecules derived from the sera of animals immunized with an antigen or an antigenic functional derivative thereof.

"Monoclonal antibodies" are substantially homogenous populations of antibodies to a particular antigen.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

By "hybridoma" is meant an immortalized cell line which is capable of secreting an antibody, for example an hOAT antibody.

By "natural-binding partner" it is meant a protein, organic anion, or other molecule that interacts with an hOAT polypeptide.

As used herein, pharmacokinetics is the process by which a drug or compound is absorbed, distributed, metabolized and eliminated by the body.

The term "compound" includes small organic or inorganic molecules of molecular weight of preferably less than 1000 atomic units, more preferably less than 800 atomic units, and most preferably less than 500 atomic units. "Organic molecules" include all molecules that contain a carbon atom, whereas "inorganic molecules" are those that do not have a carbon atom.

The term "function" refers to the cellular role of a protein. The role of the proteins of the invention may include transport of substrates into and out of a cell, involvement in cascades controlling cell growth, migration, differentiation, gene expression, muscle contraction, glucose metabolism, cellular protein synthesis, and regulation of the cell cycle.

The term "modulates" refers to the ability of a compound to alter the function of an hOAT polypeptide. A modulator preferably activates or decreases the transporter activity of an hOAT protein. A modulator that increases the transporting activity is appositive modulator; and one that decreases the transporting activity is a negative modulator. The term "modulates" also refers to altering the function of a protein by increasing or decreasing the probability that a complex, i.e. an assembly of at least two molecules bound to one another, forms between an hOAT protein and a natural-binding partner.

The term "transporting activity," in the context of the invention, defines the ability of a transporter polypeptide to uptake a substrate into a cell or efflux a molecule out of a cell.

The term "substrate" as used herein refers to a molecule that is transported into or out of a cell by an OAT polypeptide. The substrate may be an organic compound or molecule, inorganic compound or molecule, a peptide, or a protein.

The term "activates" refers to increasing the transport or efflux of a molecule into or out of a cell.

The term "inhibitor" refers to a compound or substance that binds to a substrate-binding site and, thereby, decreases or prevents transport of an hOAT substrate.

The term "expressing" as used herein refers to the production of an hOAT polypeptide from a nucleic acid vector containing an hOAT gene within a cell.

The term "adding" as used herein refers to administering a solution comprising a compound to the medium bathing cells.

The term "functional derivative" with respect to a polypeptide is a polypeptide that possesses a biological activity (either functional or structural) or an immunological characteristic that is substantially similar to a biological activity or an immunological characteristic of a non-recombinant hOAT. A functional derivative of an hOAT polypeptide may or may not contain post-translational modifications such as covalently linked carbohydrate, depending on the necessity of such modifications for the performance of a specific function. The term "functional derivative" is intended to include the "fragments", "variants", "analogues", "homologues" or chemical derivatives of a molecule.

Similarly, a "functional derivative" of a gene encoding an hOAT polypeptide of the present invention includes "fragments", "variants", or "analogues" of the gene, which may be "substantially similar" in nucleotide sequence, and which encode a molecule possessing similar activity to an hOAT polypeptide or fragment thereof. Permutations resulting from degeneracy of the genetic code are also considered functional derivatives.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical.

A "chemical derivative" of a polypeptide contains additional chemical moieties not normally a part of the polypeptide.

The term "mammalian" refers to such organisms as mice, rats, rabbits, goats, more preferably monkeys and apes, and most preferably humans.

BRIEF DESCRIPTION OF THE FIGURES

FIG. 1 shows the cDNA (SEQ ID NO:1) and deduced amino acid (SEQ ID NO:7) sequences of human OAT1.

FIG. 2 shows the cDNA (SEQ ID NO:2) and deduced amino acid (SEQ ID NO:8) sequences of human OAT2A.

FIG. 3 shows the cDNA (SEQ ID NO:3) and deduced amino acid (SEQ ID NO:9) sequences of human OAT2B.

FIG. 4 shows the cDNA (SEQ ID NO:4) and deduced amino acid (SEQ ID NO:10) sequences of human OAT3.

FIG. 5 shows the cDNA (SEQ ID NO:5) and deduced amino acid (SEQ ID NO:11) sequences of human OAT4.

FIG. 6 shows the cDNA (SEQ ID NO:6) and deduced amino acid (SEQ ID NO:12) sequences of human OAT5.

DETAILED DESCRIPTION OF THE INVENTION

A. Introduction

Figure 7:
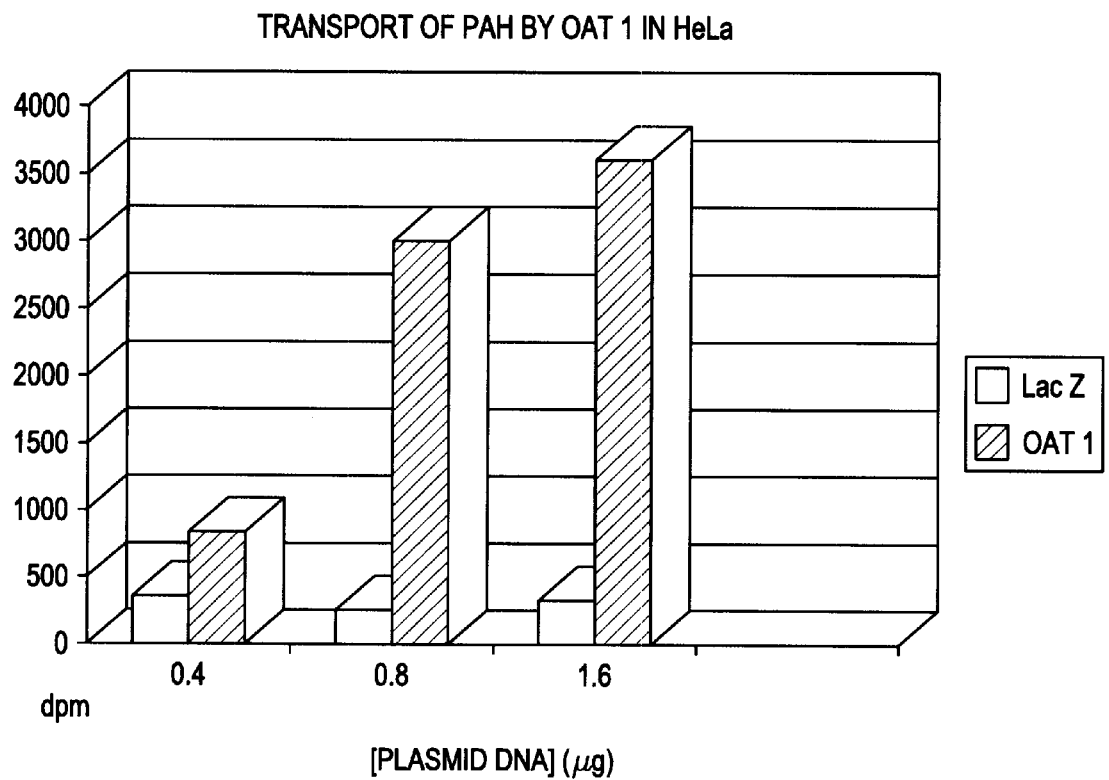
FIG. 7 shows the amount of $^3$H-PAH taken up by HeLa cells transfected with increasing amounts of hOAT1 (SEQ ID NO:1) or vector control (LacZ) cDNAs.

Organic anions are carbon-based molecules with one or more negative charges at physiological pH. They can be endogenous compounds such as bile acids or xenobiotics such as p-aminohippurate. Organic anion transporters are membrane proteins that facilitate the transport of organic anions across the cell membrane. The family described herein consists of proteins sharing at least 50% amino acid sequence similarity among each other. They show broad substrate specificity, meaning that each member can transport a variety of organic anions. Hence, they are often referred to as multi-specific organic anion transporters. The mechanism of transport, though not currently elucidated, probably is a secondary or tertiary active transport involving exchange of another organic anion. An example of a tertiary transport system is the rat kidney OAT1 transporter. The primary transport system is the $Na^+/K^+$-ATPase, which establishes the high out-to-in $Na^+$ gradient. This $Na^+$ gradient then drives the cotransport of $Na^+$ and dicarboxylates such as α-ketoglutarate through a secondary $Na^+$/dicarboxylate transporter. Finally, the tertiary transport system is established by OAT1, which exchanges external PAH for intracellular α-ketoglutarate.

The liver and kidney are two organs rich in organic anion transporters. Hepatocytes and epithelial cells of the kidney proximal tubules are polarized cells with a basolateral and apical membrane. For the hepatocyte, the basolateral membrane faces the blood-filled sinusoid. Thus, the basolateral membrane is also called the sinusoidal membrane. The apical membrane faces the canaliculus, into which bile is secreted. The hepatocyte thus can transport organic anions from the blood into the bile canaliculus across the basolateral and apical membranes. Similarly, cells of the kidney proximal tubule transport organic anions from the blood into urine across their basolateral and apical membranes. Examples of liver sinusoidal transporters are the oatp1 and oatp2, whereas OAT1 is a kidney basolateral transporter.

B. General Method

The practice of the present invention employs conventional techniques of molecular and cell biology, microbiology, and recombinant DNA. Most techniques are well-described in J. Sambrook et al., "Molecular Cloning; A Laboratory Manual" (1989) and J. Celis, ed. "Cell Biology: A Laboratory Handbook" (1998).

Identification of hOAT Nucleic Acid Molecules

Extensive searches of Genbank databases were performed using database tools available through the world wide website maintained by the National Center for Biotechnology Information (ncbi.nlm.nih.gov/). In particular, the Basic Local Alignment Search Tool (BLAST) was used to perform sequence similarity searches of the Genbank databases, such as the database containing human expressed sequence tags (ESTs). The EST database contains sequences of randomly selected clones from a variety of human cDNA libraries. Since each EST clone was sequenced with one primer, about 300–500 bp of sequence is available from each clone. The BLAST programs can translate these sequences in all possible reading frames and compare them to an input protein sequence. Human ESTs showing homology to rat OAT proteins were thereby identified.

Identified EST clones can be obtained from licensed distributors of the I.M.A.G.E. Consortium Lawrence Livermore National Laboratory (LLNL) cDNA clones. The clones are then sequenced to verify their homologies to published sequences. DNA sequencing is usually done by Sanger's method of using dideoxynucleotide triphosphates in a primer extension reaction. The DNA to be sequenced, called the template, is first denatured and then annealed to a specific primer, usually between 15–25 basepairs. In one method, $^{35}$S-adenosine triphosphate is incorporated into the growing DNA strand by a DNA polymerase. Materials for such a reaction are available from commercial kits such as Sequenase 2.0® from Amersham. Reaction products are separated on a long polyacrylamide gel, usually 6.0%, by electrophoresis using Tris-borate buffer. After electrophoresis, the gel is dried under vacuum and then exposed to autoradiographic film. The DNA sequence can be read from the autorad image and entered into computer for sequence analysis. Alternatively, fluorescent-tagged nucleotides can be incorporated by the polymerase chain reaction (PCR) into the template DNA using the thermal-stable polymerase from *Thermus aquaticus* (Taq polymerase). The PCR products can then be loaded onto an automated sequencer such as the ABI 377® (PE Applied Biosystems, Foster City, Calif.), which separates the products and determines the sequence.

Isolation of cDNA clones from a particular tissue requires the construction of a cDNA library representing messages of that tissue. Library construction entails the isolation of mRNA from the source tissue and usually a fractionation step to separate low (<0.5 kb) and high molecular weight species. The mRNAs are then primed with a DNA oligonucleotide, either a poly-thymidine or a mixture of random primers. Reverse transcriptase is then added to synthesize the complementary DNA strand. Short DNA fragments with sticky ends, called adapters, are ligated to the cDNAs so they can be subcloned into an appropriate vector. Popular vectors include bacteriophages such as λgt11 or λZAP (Stratagene, La Jolla, Calif.). For phage libraries, the cDNAs are ligated to lambda phage arms at the adapter site and then packaged into phage particles. Once packaged, the library can then be amplified by infecting an appropriate bacterial host. Ready-made libraries of various human tissues are available from several commercial sources.

To isolate a particular gene of interest from the cDNA library, an aliquot is plated out onto large plates and then transferred to nitrocellulose or nylon membrane. The phage DNA attached to the membrane is denatured in alkali solution, neutralized, and then crosslinked to the filter by baking or UV irradiation. The filter is then hybridized with a probe of interest. The probe can be an oligonucleotide or a longer, double-stranded fragment of DNA, such as the insert of an EST clone. The double-stranded probe is usually labeled with $^{32}$P to high specific activity (>$10^9$ dpm/μg), denatured by boiling for 2 minutes, and added to a hybridization buffer to concentration of $10^6$ dpm/ml. Hybridization buffers can vary in composition depending on the hybridization condition desired. One common formulation contains 0.9 M NaCl, 90 mM sodium citrate (pH 7.0), 10 mM EDTA (pH 8.0), 0.1% (w/v) Ficoll, 0.1% (w/v) polyvinylpyrrolidone, 0.1 (w/v) BSA, 0.5% SDS, and 100 μg/ml sheared, denatured salmon sperm DNA. Other formulations are available from commercial sources. The filters are hybridized with the probe at 65° C. overnight or at least 16 hours. They are then washed with sodium citrate solutions with decreasing ionic strength and increasing temperature. Finally, they are exposed to autoradiographic film with an intensifying screen at −80° C. overnight.

If a plaque contains DNA sequences complementary to the probe, the probe will hybridize to the complementary sequences on the filter. The plaque containing the complementary sequences is detected by exposing X-ray film to the filter. The plaque of interest can then be isolated and purified by conventional methods. Furthermore, once purified, the phage DNA can be manipulated so the relevant cDNA insert is excised from the phage into a phagmid by an in vivo excision procedure using appropriate host cells. The phagmids can then be amplified in bacteria and isolated by conventional methods such as alkaline lysis. Once the plasmid is purified, it can be analyzed by standard means such as restriction endonuclease or PCR mapping and DNA sequencing. DNA sequence information is analyzed for open reading frames and compared to published sequences. As discussed earlier, sets of computer programs for DNA and protein sequence analysis are commercially available.

Once a cDNA coding for a full-length transporter protein is isolated, it can be excised from its cloning vector and subcloned into an appropriate expression vector. Subcloning is a frequently used procedure in recombinant DNA technology. It involves the digestion of DNA by restriction endonucleases, fractionation of the DNA fragments by agarose gel electrophoresis, and purification of the desired fragment by a DNA-binding matrix. The purified fragment is then ligated to a precut vector of choice by adding an enzyme such as T4 DNA ligase. The new DNA construct can then be transfected into a mammalian cell line to test for functional expression. Many types of expression plasmids are commercially available and they all share common elements. An expression plasmid usually contains a bacterial origin of replication, a DNA promoter that is active in a mammalian cell line, a multiple cloning site, a transcriptional termination element, and a selective marker that confers resistance to an antibiotic. An expression plasmid harboring the cDNA of interest can be transfected into mammalian cells by several conventional means like calcium phosphate precipitation or lipofection. Many transfection kits are commercially available.

Recombinant Cells Containing a Nucleic Acid Molecule Encoding an hOAT

Cell lines which stably express hOAT polypeptides can be isolated. Such cells may be obtained by using expression vectors which carry nucleic acid sequences which encode hOAT polypeptides. The expression vectors may contain viral origins of replication and/or endogenous expression elements. Further, such expression vectors may carry nucleic acid sequences which encode for a selectable marker.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an hOAT polypeptide of the invention may be retained for its transcriptional termination regulatory sequences, such as termination and polyadenylation. Thus, by retaining the 3'-region naturally contiguous to the DNA sequence encoding an hOAT polypeptide of the invention, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding an hOAT polypeptide of the invention) are said to be operably linked if the nature of the linkage between the two DNA sequences does not (1) result in the introduction of a frame-shift mutation, (2) interfere with the ability of the promoter region sequence to direct the transcription of a gene sequence encoding an hOAT polypeptide of the invention, or (3) interfere with the ability of the gene sequence of an hOAT polypeptide of the invention to be transcribed by the promoter region sequence. Thus, a promoter region would be operably linked to a DNA sequence if the promoter were capable of effecting transcription of that DNA sequence. Thus, to express a gene encoding an hOAT polypeptide of the invention, transcriptional and translational signals recognized by an appropriate host are necessary.

The present invention encompasses the expression of a gene encoding an hOAT polypeptide of the invention (or a functional derivative thereof) in either prokaryotic or eukaryotic cells. Prokaryotic hosts are, generally, very efficient and convenient for the production of recombinant proteins and for the propagation of clones. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express an hOAT polypeptide of the invention (or a functional derivative thereof) in a prokaryotic cell, it is necessary to operably link the sequence encoding the hOAT polypeptide of the invention to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the cat promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of *E. coli*, the α-amylase (Ulmanen et al., (1985) *J. Bacteriol.* 162:176–182), and the promoters of the bacteriophages of Bacillus (Gryczan, In: The Molecular Biology of the Bacilli, Academic Press, Inc., NY, 1982), and Streptomyces promoters (Ward et al., (1986) *Mol. Gen. Genet.* 203:468–478). Prokaryotic promoters are reviewed by Glick (1987, *Ind. Microbiot.* 1:277–282), Cenatiempo (1986, *Biochimie* 68:505–516), and Gottesman (1984, *Ann. Rev. Genet.* 18:415–442).

Proper expression in a prokaryotic cell also requires the presence of a ribosome-binding site upstream of the gene sequence-encoding sequence. Such ribosome-binding sites are disclosed, for example, by Gold et al. (1981, *Ann. Rev. Microbiol.* 35:365–404). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the hOAT polypeptide of interest. Especially suitable hosts for expressing the polypeptides of the invention are eukaryotic cells. Preferred eukaryotic hosts include, for example, yeast, fungi, insect cells, amphibian oocytes, mammalian cells either in vivo, or in tissue culture. Mammalian cells which may be useful as hosts include 3T3-L1 preadipocytes, cells of fibroblast origin such as VERO or CHO-K1, or cells of lymphoid origin and their derivatives. Preferred mammalian host cells include HeLa, EcR293, SP2/0 and J558L, as well as neuroblastoma cell lines such as IMR 332, which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used (Rubin, (1988) *Science* 240:1453–1459). Alternatively, baculovirus vectors can be engineered to express large amounts of hOAT polypeptides of the invention in insect cells (Jasny, (1987) *Science* 238:1653; Miller et al., In: Genetic Engineering, Vol. 8, Plenum, Setlow et al., eds., pp. 277–297, 1986).

Any of a series of yeast expression systems can be utilized which incorporate promoter and termination elements from the actively expressed sequences coding for glycolytic enzymes. that are produced in large quantities when yeast are grown in mediums rich in glucose. Known glycolytic gene sequences can also provide very efficient transcriptional control signals. Yeast provides substantial advantages in that it can also carry out post-translational modifications. A number of recombinant DNA strategies exist utilizing strong promoter sequences and high copy number plasmids which can be utilized for production of the desired proteins in yeast. Yeast recognizes leader sequences on cloned mammalian genes and secretes peptides bearing leader sequences (i.e., pre-peptides). Several possible vector systems are available for the expression of hOAT polypeptides of the invention in a mammalian host.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of hOAT polypeptides of the invention in eukaryotic hosts requires the use of eukaryotic regulatory regions. Such regions will, in general, include a promoter region sufficient to direct the initiation of RNA synthesis. Preferred eukaryotic promoters include, for example, the promoter from the immediate-early gene of human cytomegalovirus (CMV) (Boshart M. et al., (1985) *Cell* 2:521–30, the promoter of the mouse metallothionein I gene sequence (Hamer et al., (1982) *J. Mol. Appl. Gen.* 1:273–288); the TK promoter of Herpes virus (McKnight, (1982) *Cell* 31:355–365); the SV40 early promoter (Benoist et al., (1981) *Nature* (London) 290:304–31); and the yeast gal4 gene sequence promoter (Johnston et al., (1982) *Proc. Natl. Acad. Sci.* (USA) 79:6971–6975; Silver et al., (1984) *Proc. Natl. Acad. Sci.* (USA) 81:5951–5955).

Translation of eukaryotic mRNA is initiated at the codon which encodes the first methionine. For this reason, it is preferable to ensure that the linkage between a eukaryotic promoter and a DNA sequence which encodes an hOAT polypeptide of the invention (or a functional derivative thereof) does not contain any intervening codons which are capable of encoding a methionine (i.e., AUG). The presence of such codons results either in the formation of a fusion protein (if the AUG codon is in the same reading frame as the hOAT polypeptide of the invention coding sequence) or a frame-shift mutation (if the AUG codon is not in the same reading frame as the hOAT polypeptide of the invention coding sequence).

A nucleic acid molecule encoding an hOAT polypeptide of the invention and an operably linked promoter may be introduced into a recipient prokaryotic or eukaryotic cell either as a nonreplicating DNA or RNA molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals. cDNA expression vectors incorporating such elements include those described by Okayama (1983, *Mol. Cell. Biol.* 3:280–289).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184; "Molecular Cloning: A Laboratory Manual", 1989, supra). Bacillus plasmids include pC194, pC221, pT127, and the like (Gryczan, In: The Molecular Biology of the Bacilli, Academic Press, NY, pp. 307–329, 1982). Suitable Streptomyces plasmids include p1J101 (Kendall et al., (1987) *J. Bacteriol.* 169:4177–4183), Pseudomonas plasmids are reviewed in John et al. (1986) *Rev. Infect. Dis.* 8:693–704), and Izaki (1978) *J. Bacteriol.* 33:729–742).

Preferred eukaryotic plasmids include, for example, pcDNA3.1 (Invitrogen), BPV, vaccinia, SV40, 2-micron circle, and the like, or their derivatives. Such plasmids are well known in the art (Botstein et al., (1982) Miami Wntr. Symp. 19:265–274; Broach, In: "The Molecular Biology of the Yeast Saccharomyces: Life Cycle and Inheritance", Cold Spring Harbor Laboratory, Cold Spring Harbor, N.Y., p. 445–470, 1981; Broach, (1982) *Cell* 28:203–204; Bollon et al., (1980) *J. Clin. Hematol. Oncol.* 10:39–48; Maniatis, In: Cell Biology: A Comprehensive Treatise, Vol. 3, Gene Sequence Expression, Academic Press, NY, pp. 563–608, 1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene(s) results in the production of an hOAT polypeptide of the invention, or fragments thereof This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture technique appropriate to the cell type.

Cell lines stably expressing human organic anion transporters under the control of an inducible promoter can also be isolated. For inducible expression of human organic anion transporters, the ecdysone system from Invitrogen (San Diego, Calif.) was used. Ecdysone is a hormone that regulates metamorphosis in insects, such as the fruitfly Drosophila. Like other steroid hormones, ecdysone exerts its effects by binding to a nuclear receptor, the VgR. The hormone-receptor complex then binds to a sequence of DNA called the ecdysone response element (EcRE), and activates transcription from promoters containing these elements. Since mammalian cells do not express ecdysone receptors, they normally do not respond to the insect hormone. However, if a piece of DNA under the control of an ecdysone inducible promoter is transfected into a mammalian cell line, treating the cell line with ecdysone will induce expression of the said DNA.

The cloned transporters can also be expressed in the amphibian oocytes, a widely used heterologous system for the expression of membrane proteins. Complementary RNA can be synthesized from purified cDNA in vitro if it is downstream of an appropriate promoter, such as the T3 or T7 phage promoter. The synthesized RNA are microinjected into each frog oocyte, which translates the message and expresses the protein in its membranes. Xenopus oocytes can be obtained by surgical removal of ovaries from the frog *Xenopus laevis*. The ovary lobes are treated with collagenase to remove the vitalin layer. Oocytes can be maintained for up to two weeks in Barth solution (88 mM NaCl, 1 mM KCl, 2.4 mM NaHCO$_3$, 15 mM HEPES (pH 7.6), 0.7 mM CaCl$_2$, 0.82 mM MgSO$_4$ and 50 µg/ml gentamicin) at 16° C. Typically, about 50 nl or 10–30 ng of RNA are injected into each oocyte. The injected oocytes are maintained at 16° C. for 2–3 days and then subjected to transport assays.

Assays for Functional Expression

Assaying for functional expression of transporters can be done using a labeled compound that is a known substrate of the transporter. For hOAT1, p-aminohippurate (PAH) is a high affinity substrate that is rapidly transported. Transfected cells or injected oocytes are washed briefly with media or Barth buffer and then incubated with the labeled PAH. After the desired incubation time, the excess label is washed away by adding cold buffer. The cells are then solubilized with SDS and the amount of label taken up can be determined by scintillation counting.

Other methods for measuring transport activity of organic anion transporters are well known in the art and are applicable to the present invention. For example, transport assays utilizing membrane vesicles was demonstrated by Yamazaki, et al., (1997) *Drug Metabolism and Disposition*, 1123–1129; and Pascolo, et al. (1998) *Biochem J.*331:99–103.

Cell Lines Stably Expressing hOAT Polypeptides Used to Identify Substrates, Inhibitors and Modulators of hOAT Polypeptides Cell lines stably expressing hOAT polypeptides can be used to screen for other substrates or inhibitors of hOAT polypeptides through use of a competition assay. If a test compound is well transported by an hOAT protein, it will compete with a substrate, known to be transported by a particular hOAT, for access to the transporter. Cells expressing hOAT proteins would then uptake less of the known substrate in the presence than in the absence of the competitor.

If a test compound competes with transport of a known substrate, further testing is necessary to confirm that the test compound is a substrate or inhibitor. Such confirmation can be done using techniques known to those skilled in the art, for example, the intracellular concentration of the test compound can be measured using HPLC. If a test compound, which competes with transport of a known substrate, is also found to accumulate inside a cell, this confirms that the test substrate is a substrate and not an inhibitor of the particular hOAT being tested.

Modulators can be identified by adding a test compound to cell lines stably expressing hOAT polypeptides and measuring whether the addition of the test compound increases or decreases the transport of hOAT substrates. If a modulator is identified, which decreases or inhibits the transport of a substrate, further testing, using techniques known to those skilled in the art, is necessary to confirm that such modulators are not actually competitive inhibitors. One such technique involves adding more substrate in a competition assay to determine if said substrate can compete with the inhibitory effects of the putative modulator. If adding more substrate has no affect on the modulating activity then the modulator is not a competitive inhibitor.

Nucleic Acid Probes, Methods, and Kits for Detection of the hOAT Polypeptides

A nucleic acid probe of the present invention may be used to probe an appropriate chromosomal or cDNA library by usual hybridization methods to obtain other nucleic acid molecules of the present invention. A chromosomal DNA or cDNA library may be prepared from appropriate cells according to recognized methods in the art (cf. "Molecular Cloning: A Laboratory Manual", second edition, Cold Spring Harbor Laboratory, Sambrook, Fritsch, & Maniatis, eds., 1989).

In the alternative, chemical synthesis can be carried out in order to obtain nucleic acid probes having nucleotide sequences which correspond to N-terminal and C-terminal portions of the amino acid sequence of the polypeptide of interest. The synthesized nucleic acid probes may be used as primers in a polymerase chain reaction (PCR) carried out in accordance with recognized PCR techniques, essentially according to PCR Protocols, "A Guide to Methods and Applications", Academic Press, Michael, et al., eds., 1990, utilizing the appropriate chromosomal or cDNA library to obtain the fragment of the present invention.

One skilled in the art can readily design such probes based on the sequence disclosed herein using methods of computer alignment and sequence analysis known in the art ("Molecular Cloning: A Laboratory Manual", 1989, supra). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

One method of detecting the presence of nucleic acids of the invention in a sample comprises (a) contacting the sample with the above-described nucleic acid probe under conditions such that hybridization occurs, and (b) detecting the presence of the probe bound to the nucleic acid molecule. One skilled in the art would select the nucleic acid probe according to techniques known in the art as described above. Samples to be tested include but should not be limited to RNA samples of human tissue.

A kit for detecting the presence of nucleic acids of the invention in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabeled probes, enzymatic labeled probes (horseradish peroxidase, alkaline phosphatase), and affinity labeled probes (biotin, avidin, or streptavidin). Preferably, the kit further comprises instructions for use.

Antibodies, Hybridomas, Methods of Use and Kits for Detection of the hOAT Polypeptides The present invention relates to an antibody having binding affinity to an hOAT polypeptide of the invention. The polypeptide may have the amino acid sequence encoded by the nucleic acid sequence set forth in SEQ ID NO:1, SEQ ID NO:2, SEQ ID NO:3, SEQ ID NO:4, SEQ ID NO:5, SEQ ID NO:6, or a functional derivative thereof, or the amino acid sequence set forth in SEQ ID NO:7 or SEQ ID NO:8, SEQ ID NO:9, SEQ ID NO:10, SEQ ID NO:11, SEQ ID NO:12, or a functional derivative thereof, or at least 9 contiguous amino acids thereof (preferably, at least 20, 30, 40, 50 or 60 contiguous amino acids thereof).

The present invention also relates to an antibody having specific binding affinity to an hOAT polypeptide of the invention. Such an antibody may be isolated by comparing its binding affinity to an hOAT polypeptide of the invention with its binding affinity to other polypeptides. Those which bind selectively to an hOAT polypeptide of the invention would be chosen for use in methods requiring a distinction between an hOAT polypeptide of the invention and other polypeptides, including other polypeptides with similar amino acid sequences. Such methods could include, but should not be limited to, the analysis of altered hOAT polypeptide expression in tissue containing other polypeptides.

The hOAT polypeptides of the present invention can be used to produce antibodies or hybridomas. One skilled in the art will recognize that if an antibody is desired, such a peptide could be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The present invention also relates to hybridomas that produce the above-described monoclonal antibodies, or binding fragment thereof. A hybridoma is an immortalized cell line that is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., (1980), *J. Immunol. Methods* 35:1–21). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal that is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell that produces an antibody with the desired characteristics. These include screening the hybridomas with an ELISA assay, western blot analysis, or radioimmunoassay (Lutz et al., (1988) *Exp. Cell Res.* 175:109–124). Hybridomas secreting the desired antibodies are cloned and the class and subclass are determined using procedures known in the art (Campbell, (1984) "Monoclonal Antibody Technology: Laboratory Techniques in Biochemistry and Molecular Biology", supra).

For polyclonal antibodies, antibody-containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see Stemberger et al., (1970) *J. Histochem. Cytochem.* 18:315; Bayer et al., (1979) *Meth. Enzym.* 62:308; Engval et al., (1972) *Immunol.* 109:129; Goding, J. (1976) *Immunol. Meth.* 13:215). The labeled antibodies of the present invention can be used for in vitro, in vivo, and in situ assays to identify cells or tissues that express a specific peptide.

The above-described antibodies may also be immobilized on a solid support. Examples of such solid supports include plastics such as polycarbonate, complex carbohydrates such as agarose and sepharose, acrylic resins such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., (1974) Meth. Enzym. 34, Academic Press, N.Y.). The immobilized antibodies of the present invention can be used for in vitro, in vivo, and in situ assays as well as in immunochromotography.

The present invention also encompasses a method of detecting an hOAT polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard ("An Introduction to Radioimmunoassay and Related Techniques" Elsevier Science Publishers, Amsterdam, The Netherlands, 1986), Bullock et al. ("Techniques in Immunocytochemistry," Academic Press, Orlando, Fla. Vol. 1, 1982; Vol. 2, 1983; Vol. 3, 1985), Tijssen ("Practice and Theory of Enzyme Immunoassays: Laboratory Techniques in Biochemistry and Molecular Biology," Elsevier Science Publishers, Amsterdam, The Netherlands, 1985).

The immunological assay test samples of the present invention include cells, protein or membrane extracts of cells, or biological fluids such as blood, serum, plasma, or urine. The test samples used in the above-described method will vary based on the assay format, nature of the detection method and the tissues, cells or extracts used as the sample to be assayed. Methods for preparing protein extracts or membrane extracts of cells are well known in the art and can readily be adapted in order to obtain a sample which is testable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. Preferably, the kit also contains instructions for use. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents that are capable of reacting with the labeled antibody. The compartmentalized kit may be as described above for nucleic acid probe kits. One skilled in the art will readily recognize that the antibodies described in the present invention can readily be incorporated into one of the established kit formats that are well known in the art.

EXAMPLES

Example 1

Identification of Human EST Clones Homologous to Rat Organic Anion Transporter Proteins The cloning of rat kidney organic anion transporter OAT1 (Sekine, et al., (1997) *J. Biol. Chem.* 30: 18526–18529) and liver transporter OAT2 (Sekine, et al., (1998) *FEBS Letters* 429: 179–182) has been previously reported. The published amino acid sequences of OAT1 and OAT2 from rat were used as input sequences to perform a BLAST search of human expressed sequence tags (EST) sequences deposited in Genbank. The BLAST search identified several sequences that show amino acid homology to rat OAT1 and OAT2.

EST clones accession Nos. R25797 and AI016020 show high homology to rat OAT1 and OAT2, respectively. The clones isolated using EST clones R25797 and AI016020 were named hOAT1 (SEQ ID NO:1) and hOAT2 (SEQ ID NO:2), respectively. The other ESTs show lower homology to rat OAT1 and OAT2. These other EST clones have been named hOAT3 (SEQ ID NO:4), hOAT4 (SEQ ID NO:5), and hOAT5 (SEQ ID NO:6). The latter three clones are not considered human homologues to the rat OAT1 and OAT2.

Example 2

Isolation of Full-length Human OAT1 cDNA

The human EST clone R25797, listed in Example 1, was purchased from a distributor of IMAGE Consortium (LLNL) cDNA Clones (Lennon, et al., *Genomics* 33: 151–52 (1996)). EST cDNA clone R25797 was sequenced to verify its homology to rat OAT1. The cDNA insert was excised by NotI and HindIII digestion and purified by agarose gel electrophoresis. These DNA fragments were then labeled with $^{32}$P-α-deoxyadenosine triphosphate (3000 Ci/mmol) using the Prime-a-Gene labeling system (Promega, Madison, Wis.) to a specific activity greater than $1\times10^9$ dpm/μg.

A human kidney cDNA library in pTripleEx vector (Clontech, Palo Alto, Calif.) was plated out on 10 cm-diameter plates at a density of $5\times10^4$ pfu/plate. The plates were incubated at 37° C. for 6–8 hours until each plaque was about 0.3–0.5 mm in diameter. Plaque lifts were performed by placing a nylon membrane on each plate for 2 minutes. The nylon membrane was then lifted carefully from the plate and immersed in 1.5 M NaCl and 0.5 M NaOH for 2 minutes to denature the attached DNA. The nylon was then placed in 1.5 M NaCl and 0.5 M Tris (pH 8.0) for neutralization. Finally, the membrane was quickly rinsed in 2×SSC (0.3 M NaCl and 30 mM sodium citrate). The attached DNA was crosslinked by UV irradiation. Filters were incubated in hybridization buffer with radioactive probes at a concentration of $1\times10^6$ dpm/ml in roller bottles at 65° C. overnight. The next day, the filters were washed with 2×SSC and 0.1% SDS for 15 minutes at 25° C. for two times. They were then washed with 0.2×SSC and 0.1% SDS for 1 hour at 65° C. After the final wash, filters were exposed to autoradiographic film with an intensifying screen at −80° C. overnight. Positive clones, which show up as dark spots on the autorad, were identified and a 3 mm-diameter agar plug was removed from the original plate.

The positive clone was purified by subsequent rounds of hybridization until a well-isolated plaque could be obtained. The cDNA of interest was excised from the phage into a phagmid by an in vivo excision procedure using BM25.8 cells as host (Clontech, Palo Alto, Calif.). Phagmids were amplified, purified, and sequenced using standard procedures. The DNA sequence was analyzed for open reading frames and compared to published sequences.

One positive plaque isolated from the above procedure was 2.5 kb in length. Analysis of its sequence revealed an open-reading frame with a deduced amino acid sequence showing high homology to the rat OAT1 protein (Table 1). This clone was designated human OAT1 (hOAT1), or the human homologue of rat OAT1. The entire cDNA (SEQ ID NO:1) and deduced amino acid (SEQ ID NO:7) sequences of human OAT1 are shown in FIG. 1.

The isolated cDNA encoding for hOAT1 is predicted to encode a polypeptide with a length of 550 amino acids. Computer analysis of the deduced amino acid encoded by hOAT1 cDNA reveals consensus protein kinase C (PKC) phosphorylation sites at amino acids 271, 278, and 284.

Computer analysis using the GAP-Alignment program from the Wisconsin Genetics Software Package indicates that hOAT1 polypeptide is 88% identical to rat OAT1 polypeptide and 39% identical to rat OAT2 polypeptide (Table 1). GAP analysis also indicates that hOAT1 is 86% identical to rat OAT1 nucleotide sequence (Table 1).

EST accession number R25797 is homologous to hOAT1 cDNA (SEQ ID NO:1) at nucleotides 398–2100 (FIG. 1).

TABLE 1

Homology Among Human and Rat Organic Anion Transporters

| | hOAT1 (SEQ ID NOS:1,7) | | hOAT2A (SEQ ID NOS:2,8) | | hOAT2B (SEQ ID NOS:3,9) | | hOAT3 (SEQ ID NOS:4,10) | | hOAT4 (SEQ ID NOS:5,11) | | hOAT5 (SEQ ID NOS:6,12) | |
|---|---|---|---|---|---|---|---|---|---|---|---|---|
| | N[1] | (A)[2] | N | (A) | N | (A) | N | (A) | N | (A) | N | (A) |
| rat OAT1 | 86% | (88%) | 53% | (37%) | 53% | (37%) | 60% | (50%) | 48% | (36%) | 51% | (40%) |
| rat OAT2 | 53% | (39%) | 82% | (79%) | 82% | (79%) | 51% | (37%) | 44% | (30%) | 46% | (31%) |
| hOAT1 | | | 54% | (39%) | 55% | (39%) | 61% | (51%) | 49% | (37%) | 50% | (40%) |
| hOAT2A | | | | | 99% | (98%) | 52% | (38%) | 44% | (32%) | 45% | (32%) |
| hOAT2B | | | | | | | 52% | (39%) | 44% | (33%) | 45% | (32%) |
| hOAT3 | | | | | | | | | 52% | (37%) | 52% | (39%) |
| hOAT4 | | | | | | | | | | | 72% | (55%) |
| hOAT5 | | | | | | | | | | | | |

[1]N indicates the percentage of identical nucleotides found between compared nucleic acid sequences as determined using the GAP-Alignment program in the GCG software package, using a gap weight of 5.0 and a length weight of 0.3.
[2](A) indicates the percentage of identical amino acids found between compared polypeptides as determined using the GAP-Alignment program in the GCG software package, using a gap weight of 3.0 and a length weight of 0.1.

Example 3
Isolation of Full-length Human OAT2A and OAT2B cDNA

Human OAT2 cDNA was cloned in the same manner as described for human OAT1 cDNA in Example 1 except that EST accession number-AI016020 was used as a probe. In addition, hOAT2A (SEQ ID NO:2) and hOAT2B (SEQ ID NO:3) were isolated from a cDNA library obtained from human liver rather than kidney, as was hOAT1.

The entire cDNA (SEQ ID NO:2) and deduced amino acid (SEQ ID NO:8) sequences of human OAT2A are shown in FIG. 2. Human OAT2A (hOAT2A) cDNA is predicted to encode a polypeptide that is 546 amino acids in length. Computer analysis of the deduced amino acid sequence using the GAP-Alignment program indicates that human OAT2A polypeptide is 79% identical to rat OAT2 polypeptide (Table 1). GAP analysis also indicates that the nucleotide sequence for hOAT2A is 82% identical to the nucleotide sequence of rat OAT2.

EST accession number AI016020 is homologous to hOAT2A cDNA (SEQ ID NO:2) at nucleotide sequences 20–1400 (FIG. 2).

The entire cDNA (SEQ ID NO:3) and deduced amino acid (SEQ ID NO:9) sequences of human OAT2B (hOAT2B) are shown in FIG. 3. Human OAT2B cDNA is predicted to encode a polypeptide that is 538 amino acids in length. Human OAT2B (SEQ ID NO:3) is identical to hOAT2A (SEQ ID NO:2) except at its C-terminus end. Without wishing to be bound by any particular theory, hOAT2B could be an mRNA splice variant of hOAT2A.

Example 4
Isolation of Full-length Human OAT3 cDNA

Human OAT3 (hOAT3) cDNA was isolated as described for hOAT1 cDNA in Example 1 except that EST accession number-H41333 was used as a probe. The entire cDNA (SEQ ID NO:4) and deduced amino acid (SEQ ID NO:10) sequences of human OAT3 are shown in FIG. 4. Computer analysis of the hOAT3 cDNA sequence predicts that hOAT3 cDNA encodes a polypeptide that is 542 amino acids in length. Computer analysis of the deduced amino acid sequence reveals consensus PKC phosphorylation sites at amino acids 259, 266, 269, 511, and 527.

EST accession number H41333 is homologous to hOAT3 cDNA (SEQ ID NO:4) at nucleotides 1169–2121 (FIG. 4).

Example 5
Isolation of Full-length Human OAT4 cDNA

Human OAT4 (hOAT4) cDNA was cloned in the same manner as described for human OAT1 cDNA in Example 1 except that EST accession number-AA705512 was used as a probe. In addition, hOAT4 cDNA was isolated from a cDNA library obtained from human liver rather than kidney, as was hOAT1. The entire cDNA (SEQ ID NO:5) and deduced amino acid (SEQ ID NO:11) sequences of human OAT4 are shown in FIG. 5. Computer analysis of human OAT4 cDNA predicts that hOAT4 cDNA encodes a polypeptide that is 554 amino acids in length. Computer analysis of the deduced amino acid sequence reveals a consensus PKC phosphorylation site at amino acid 324.

EST accession number AA705512 is homologous to hOAT4 cDNA (SEQ ID NO:5) at nucleotides 1–1232 (FIG. 5).

Example 6
Isolation of Full-length hOAT5 cDNA

Human OAT5 (hOAT5) cDNA was cloned in the same manner as described for human OAT1 cDNA in Example 1 except that EST accession number-AA705512 was used as a probe. In addition, hOAT5 cDNA was isolated from a cDNA library obtained from human liver rather than kidney, as was hOAT1. The entire cDNA (SEQ ID NO:6) and deduced amino acid (SEQ ID NO:12) sequences of human OAT5 are shown in FIG. 6. Human OAT5 cDNA is predicted to encode a polypeptide that is 541 amino acids in length. Computer analysis of the deduced amino acid sequence reveals consensus PKC phosphorylation sites at amino acids 282, 289, 345, and 526.

EST accession number AA705512 is homologous to hOAT5 cDNA (SEQ ID NO:12) at nucleotides 1–1193 (FIG. 6).

Example 7
Functional Expression of Human OAT1 in HeLa Cells

Human OAT1 cDNA (SEQ ID NO:1) was subcloned into the mammalian expression vector pcDNA3.1 (Invitrogen, San Diego, Calif.), which contains a cytomegalovirus promoter. The plasmid construct (pcDNA-hOAT1) was then amplified and purified. The construct was transfected into HeLa cells (ATCC), cultured in 25 mm$^2$ flasks, using the Effectene transfection reagent (Qiagen, Stanford Santa Clarita, Calif.). Control cell lines were transfected with a pcDNA-lacZ construct. One day post-transfection, the cells were split into six (6)-well plates and cultured for another twenty-four (24) hours. Transfected cells were tested for transport of $^3$H-p-aminohippurate, a classical substrate of the kidney organic anion transporter. Since OAT1 is an antiporter, the transfected cells were first preloaded with 1 mM glutarate for one (1) hour. The glutarate-containing media was removed and replaced with media containing 50 µM PAH at 1 µCi/ml. After ten (10) minutes at 37° C., the media was aspirated and the cells were washed three times with ice cold phosphate-buffered saline (PBS). The cells were then solubilized with 0.5% SDS. The amount of labeled PAH transported into the cells was determined by a scintillation counter. As shown in FIG. 7, HeLa cells transfected with hOAT1 were able to uptake PAH whereas HeLa cells transfected with a vector control were only able to uptake a very small amount of PAH (almost 10-fold less than cells transfected with a vector containing DNA encoding hOAT1).

Example 8
Functional Expression of hOAT1 in Xenopus Oocytes

Figure 8:
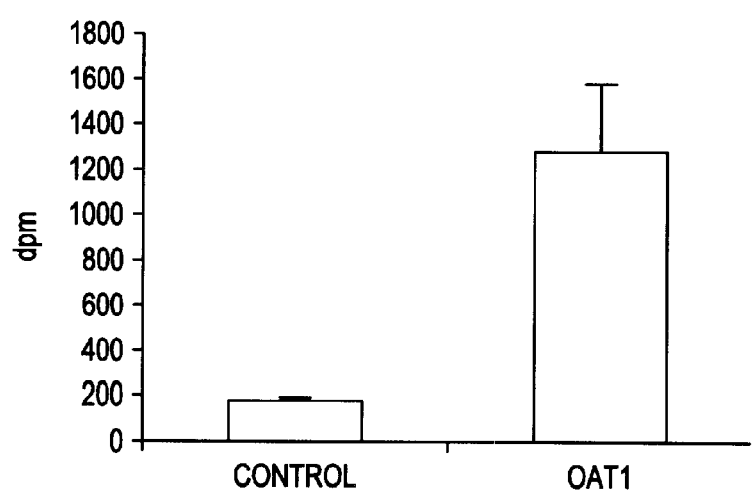
FIG. 8 shows that oocytes injected with hOAT1 RNA uptake $^3$H-PAH to a much greater extent than water injected oocytes.

Complementary hOAT1 RNA was synthesized in vitro from the pcDNA-hOAT1 plasmid using T7 RNA polymerase (Ambion, Austin, Tex.). The transcription reaction was performed at 37° C. for 2 hours. The RNA was purified by phenol and chloroform extraction and precipitated with ammonium acetate and ethanol. Purified RNA was analyzed for size and purity by agarose gel electrophoresis. RNA was resuspended in water at a concentration of 0.3 µg/µl. Oocytes were prepared from ovaries removed from female *Xenopus laevis* according to White et al., (1985) *PNAS* 82:4852–56. About 15 ng of hOAT1 cRNA in 50 nl was injected into each oocyte. As a control, 50 nl of water was injected into each oocyte. The injected oocytes were assayed for transport of PAH two (2) days post-injection. Oocytes were preloaded with 1 mM glutarate for 2 hours in Barth buffer. Transport assays were conducted in modified Barth buffer (100 mM NaCl, 2 mM KCl, 1 mM $CaCl_2$, 1 mM $MgCl_2$, 10 mM HEPES, pH 7.5) with 50 µM PAH at 4 µCi/ml. After a one (1) hour incubation at 25° C., oocytes were washed with 3 ml ice cold transport assay buffer three (3) times. Each oocyte was solubilized in 0.5 ml 0.5% SDS and subjected to scintillation counting. As shown in FIG. 8, oocytes injected with the hOAT1 RNA uptake $^3$H-PAH to a much greater extent than water injected oocytes.

Example 9
Identification of Fluorescein as a Substrate for hOAT1

Human embryonic kidney (HEK293) cells were transfected with pcDNA-hOAT1, as in Example 7. One day after transfection the cells were assayed for transport of fluorescein or SITS. Ten (10) µM of either substrate was added to the external media for ten (10) minutes at 37° C. The cells were washed with ice-cold PBS to remove excess label and analyzed under a fluorescent microscope. Cells that take up either fluorescein or SITS are predicted to turn fluorescent green. Fluorescent microscopy revealed that hOAT1-expressing cells took up fluorescein but not SITS.

Example 10
Competition Assay to Identify Substrates of hOAT1 Using Fluorescein

HEK293 cells were transiently transfected with pcDNA3-hOAT1 as in Example 7 and assayed for transport of fluorescein, but in the presence or absence of 0.5 mM PAH. Since fluorescein and PAH are both substrates of hOAT1, they will compete for access to the transporter. As evidenced by fluorescent microscopy, hOAT1-expressing cells showed uptake of fluorescein in the absence but not in the presence of external PAH.

Example 11
Establishment of Cell Lines Stably Expressing hOATs

Vector pIND(sp1) (Invitrogen) contains the ecdysone-inducible promoter (EcRE). Using standard methods known to those in the art, cDNAs encoding hOAT1 (SEQ ID NO:1), hOAT2A (SEQ ID NO:2), into vector pIND/sp1 downstream of its EcRE promoter. After cloning, the vectors were separately transfected into cell line EcR293 (Invitrogen). The EcR293 cell line is a derivative of cell line HEK 293 and contains a stably integrated pVgRXR vector. The pVgRXR vector constitutively expresses the ecdysone receptor and the retinoid X receptor (RXR). The ecdysone receptor and RXR form a heterodimer which, upon activation by the hormone ecdysone, binds to a promoter containing the EcRE. The pVgRXR vector was maintained within the EcR293 cell line by selection with 400 µg/ml zeocin. The pIND(sp1)-hOAT plasmids contain a neomycin resistance marker, and cells stably integrating the plasmids were selected for by culturing the cells in media supplemented with 400 µg/ml G418. After two weeks of selection, individual colonies appeared and were isolated and expanded. To test for expression of the transporter, the cells were induced with 1.25 µg/ml ponasterone, an ecdysone analogue, for twenty-four (24) hours. The cells were then subjected to standard transport assays.

Figure 9:
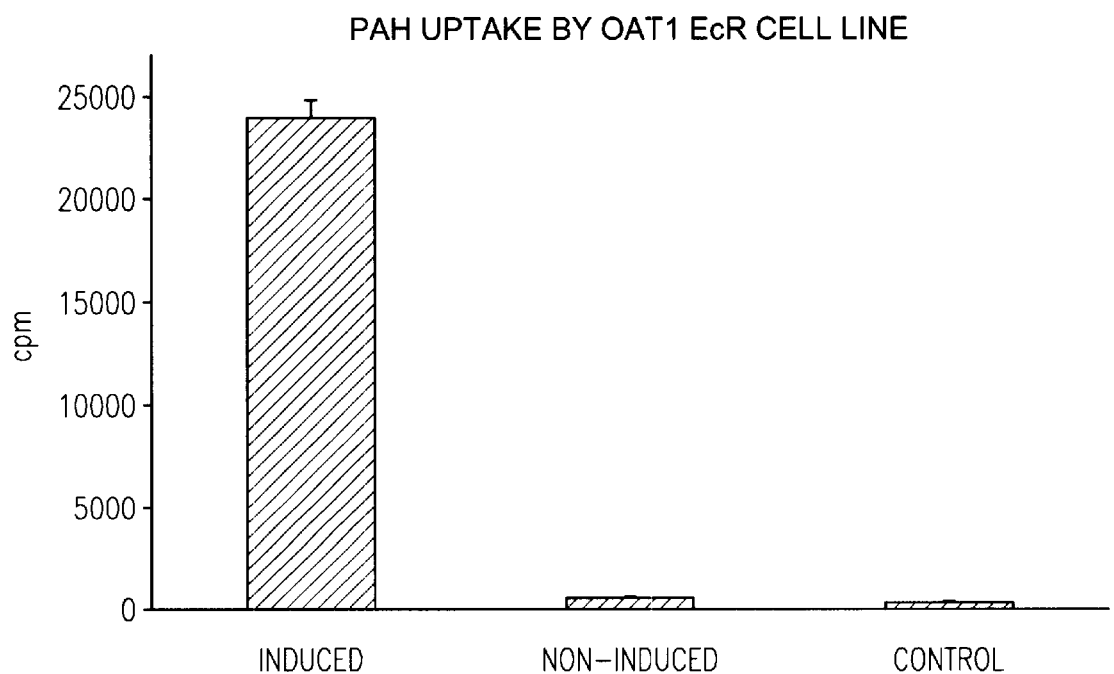
FIG. 9 shows that ECR293 cells stably containing hOAT1, in plasmid pIND(sp1), uptake approximately 50-fold more $^3$H-PAH when induced by ponasterone than non-induced cells.
Figure 10:
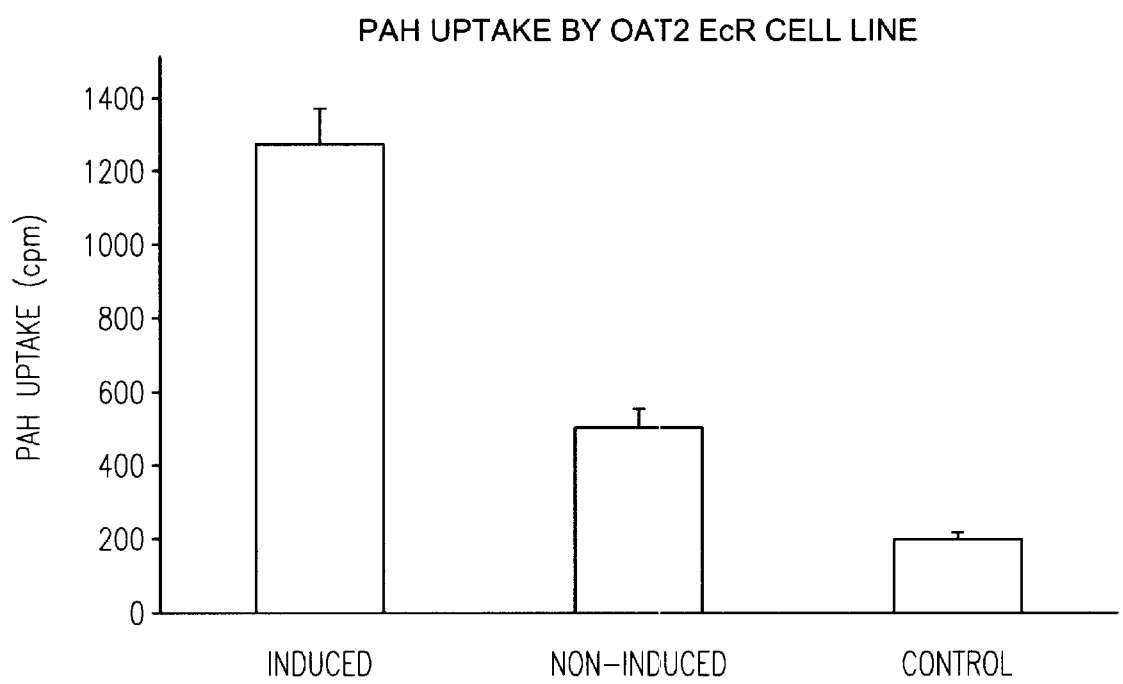
FIG. 10 shows that ECR293 cells stably containing hOAT2A, in plasmid pIND(sp1), uptake approximately 2.6-fold more $^3$H-PAH when induced by ponasterone than non-induced cells.

EcR293 cells with stably integrated pIND(sp1)-hOAT1 expressed hOAT1 at a basal level that was not harmful to the cells. These cells grow at a rapid rate comparable to the parental EcR293 cells. Hence, the hOAT1 cDNA can be maintained within these cells indefinitely. Expression of hOAT1 at high levels can be easily achieved by inducing with ponasterone for twenty-four (24) hours. As shown in FIG. 9, ECR293 cells containing hOAT1 in plasmid pIND (sp-1) uptake approximately 50-fold more PAH when induced by ponasterone than non-induced cells containing pIND(sp-1)-hOAT1. ECR293 cells stably containing hOAT2A, in plasmid pIND(sp-1), uptake approximately 2.6-fold more $^3$H-PAH when induced by ponasterone than non-induced cells (FIG. 10). Cell lines stably expressing hOAT2B, hOAT3, hOAT4, and hOAT5 can be established using the same method as for hOAT1 and hOAT2A.

Figure 11:
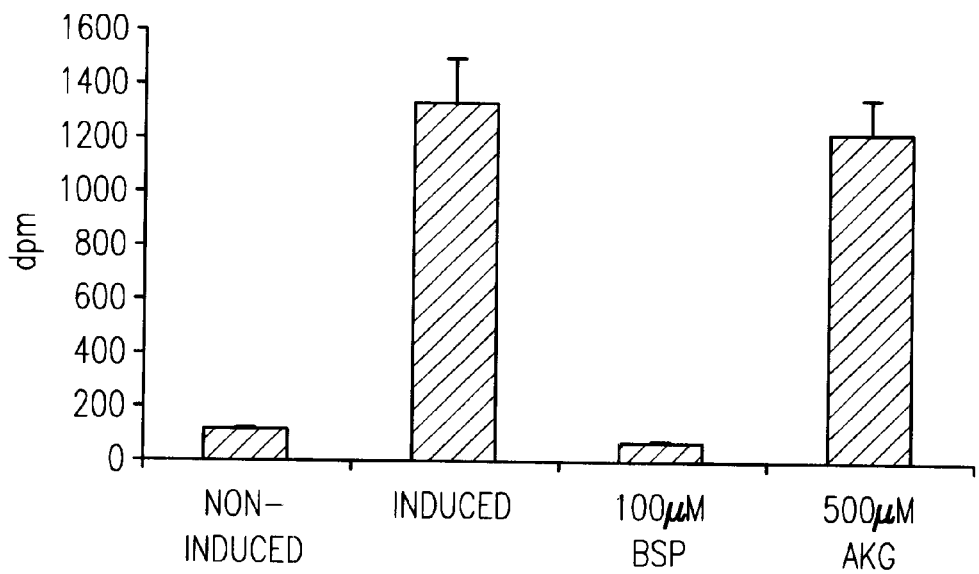
FIG. 11 shows that sulfobromophthalein but not α-ketoglutarate competed with $^3$H-PAH uptake in ECR293/OAT2A cells induced with ponasterone.

Example 12
Competition Assay to Identify New Substrates of hOAT2, Using a Radiolabeled Substrate EcR293/OAT2A cells were assayed for transport of $^3$H-PAH as in Example 7. The uptake of $^3$H-PAH was blocked by 100 µM sulfobromophthalein (BSP) but not 500 µM α-ketoglutarate (AKG) (FIG. 11). The competition assay thus identified BSP and not AKG as a preferred substrate of hOAT2A.

Example 13
Predicting Pharmacokinetics in Man Using a Panel of hOAT Expressing Cells A panel of different cell lines, each expressing a particular human OAT protein, can be used to predict pharmacokinetics for anionic drugs. For instance, PAH is a compound transported rapidly by hOAT1 and to a much lesser extent by the other human OATs disclosed in the invention. The panel of hOAT expressing cells would predict that PAH is eliminated rapidly by the human kidney, as previously described. Similarly, the competition assays in Examples 10 and 12 showed that fluorescein is a very good substrate of human OAT1 and that BSP is a good substrate of human OAT2A. Therefore, the assay would predict that fluorescein is eliminated from the human body mainly via kidney excretion and that BSP is mainly eliminated from the human body via liver excretion.

Further confirmation that a compound is a substrate of an hOAT would be done using in vivo tissue distribution assays. Compounds found to be transported by hOATs, using the cell line described above, would be injected into animals and followed to confirm their transport by the appropriate hOAT. For instance, a compound found to be transported by a cell line stably expressing hOAT1, would be expected to be excreted in the urine of an animal injected with the said compound. Similarly, a compound found to be transported by a cell line expressing hOAT2, would be expected to be transported into the liver of animals injected with said compound.

Since hOAT4 (SEQ ID NO11) and 5 (SEQ ID NO:12) have homology to OCTs, their range of substrates may include organic cations. Therefore, these transporters may be used to predict the pharmacokinetics of certain cationic drugs as well, using the methods described herein.

Example 14
Identification of hOAT Substrates Using Antiporter Activity

EcR293/hOAT1 cells are incubated with $^3$H-α-ketoglutarate for an hour to preload with labeled α-ketoglutarate. A test substrate is added to the cells. After a 10 minute incubation, an aliquot of the supernatant is removed and measured for effluxed α-ketoglutarate by scintillation counting. Substrates of hOAT1 will show trans-stimulation of α-ketoglutarate exchange. Inhibitors or non-substrates of hOAT1 will not stimulate α-ketoglutarate efflux.

Example 15
Cytoxicity Assays Using Cell Lines Stably Expressing hOAT Polypeptides EcR293 cells stably transformed with hOAT polypeptides can be used to screen for compounds potentially toxic to certain organs or tissues through use of a cytoxicity assay. Test compounds can be added to cell lines stably expressing hOAT polypeptides. Compounds transported by hOAT polypeptides and which are toxic will cause cell death. Cell death can be measured or determined using techniques well known in the art, such as visual inspection, microscopic inspection, and dye exclusion. Using dye exclusion, healthy cells are able to exclude a particular dye whereas injured or dead cells are unable to exclude the dye.

The foregoing examples are not limiting and are merely representative of various aspects and features of the present invention. All references referred to above are incorporated herein by reference.

Example 16
Functional Expression of hOAT3 in Xenopus Oocytes

Figure 12:
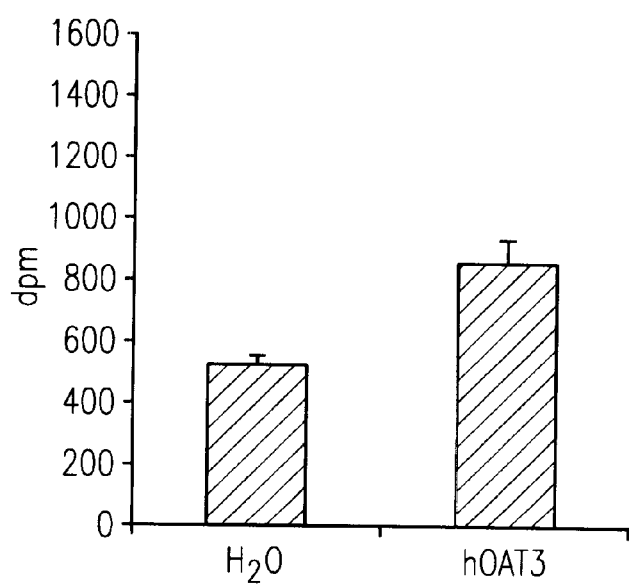
FIG. 12 shows that oocytes injected with hOAT3 RNA uptake $^3$H-PAH to a much greater extent than water injected oocytes.

Complementary hOAT3 (SEQ ID NO:4) RNA was synthesized in vitro from the pcDNA-hOAT3 plasmid using T7 RNA polymerase (Ambion, Austin, Tex.). The transcription reaction was performed at 37° C. for 2 hours., The RNA was purified by phenol and chloroform extraction and precipitated with ammonium acetate and ethanol. Purified RNA was analyzed for size and purity by agarose gel electrophoresis. RNA was resuspended in water at a concentration of 0.5 μg/μl. Oocytes were prepared from ovaries removed from female Xenopus laevis according to White et al., (1985) PNAS 82:4852–56. About 25 ng of hOAT3 cRNA in 50 nl was injected into each oocyte. As a control, 50 nl of water was injected into each oocyte. The injected oocytes were assayed for transport of PAH two (2) days post-injection. Transport assays were conducted in modified Barth buffer (100 mM NaCl, 2 mM KCl, 1 mM CaCl$_2$, 1 mM MgCl$_2$, 10 mM HEPES, pH 7.5) with 50 μM PAH at 10 μCi/ml. After a one (1) hour incubation at 25° C., oocytes were washed with 3 ml ice cold transport assay buffer three (3) times. Each oocyte was solubilized in 0.5 ml 0.5% SDS and subjected to scintillation counting. As shown in FIG. 12, oocytes injected with the hOAT3 RNA uptake $^3$H-PAH to a much greater extent than water injected oocytes.

Example 17
Determination of Tissue Distribution of hOATs

The individual hOAT cDNAs were labeled with $^{32}$P-ATP to a specific activity of >1×10$^9$ dpm/μg using the Strip-EZ kit™ (Ambion). The Strip-EZ kit™ allows easy removal of probes from a blot and the blot can thus be reprobed several times without substantial loss of signal. The Human Multiple Tissue Northern blot was obtained from Clontech, which contained mRNA extracted from 12 different human tissues. The blot was successively hybridized with each hOAT probe in 5 ml of ExpressedHyb buffer (Clontech) at a final concentration of 3–5×10$^6$ dpm/ml. Hybridization was carried out at 65° C. for 4 hrs. The blot was washed two times with 2×SSC and 0.1% SDS at 65° C. for 15 min each, and then once with 0.1×SSC and 0.1% SDS at 65° C. for 1 hr. The blot was then exposed to BioMax MR autographic film (Kodak) with intensifying screen at –80° C. for 24 hrs.

Figure 13A:
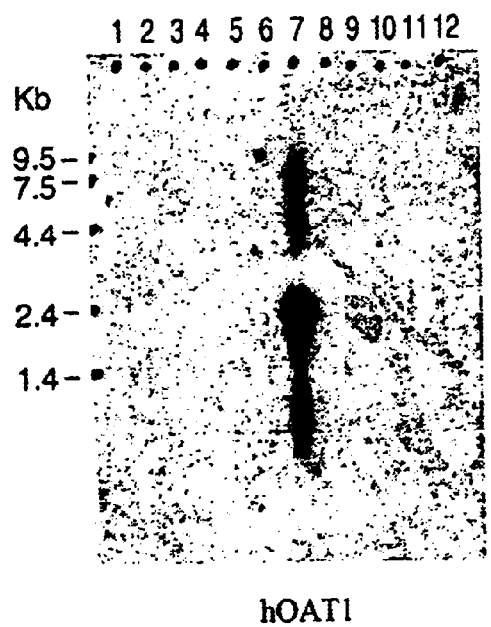
FIGS. 13(A–E) shows Northern Blot analyses of hOAT1-5 mRNA in various human tissues.
Figure 13B:
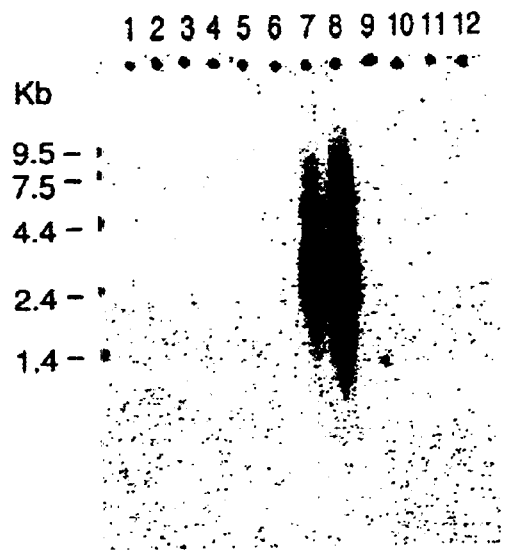
Figure 13C:
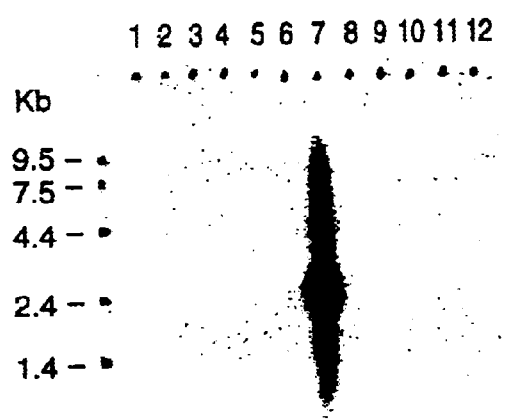
Figure 13D:
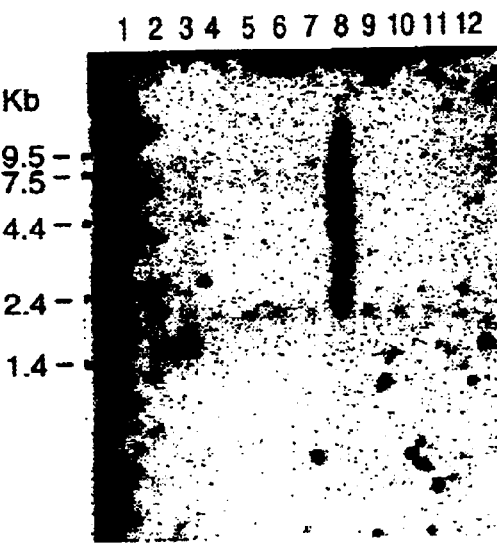
Figure 13E:
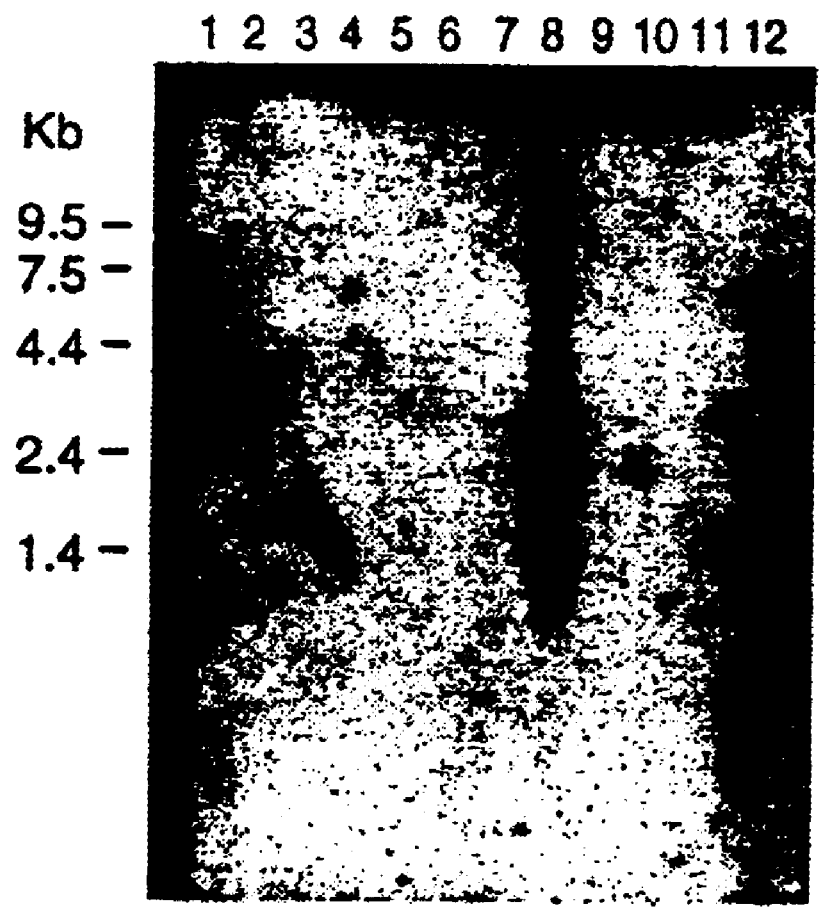

The northern analysis shows that hOAT1 was expressed only in human kidney (FIG. 13A). The hOAT1 probe hybridized to a major band at about 2.4 kb. The hOAT2 probe hybridized to two major bands at about 2.4 and about 3 kb from liver and kidney, with higher levels in the liver than in the kidney (FIG. 13B). hOAT3 was expressed only in the kidney, with a major transcript of about 2.4 kb and minor transcript at about 4.3 kb (FIG. 13C). hOAT4 and hOAT5 were expressed exclusively in the liver (FIGS. 13D and 13E). hOAT4 probe hybridized to a major band at about 4.3 kb and hOAT5 probe hybridized to a major band at about 2.5 kb. Hence, northern analyses indicated that hOAT1 and hOAT3 are mainly kidney transporters and hOAT4 and hOAT5 are liver transporters, whereas hOAT2 is a liver and kidney transporter.

All patents and publications mentioned in the specification are indicative of the levels of skill of those skilled in the art to which the invention pertains. All references cited in this disclosure are incorporated by reference to the same extent as if each reference had been incorporated by reference in its entirety individually. None of the references are admitted to be prior art.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the following claims.

SEQUENCE LISTING

<160> NUMBER OF SEQ ID NOS: 12

<210> SEQ ID NO 1
<211> LENGTH: 2121
<212> TYPE: DNA
<213> ORGANISM: Homo sapiens

<400> SEQUENCE: 1

| | | | | | |
|---|---|---|---|---|---|
| ctgagctgac | ctgaccccca | aagtgaagga | gaagctgcaa | gggaaaaggg | agggacagat | 60 |
| cagggagacc | ggggaagaag | gaggagcagc | caaggaggct | gctgtccccc | cacagagcag | 120 |
| ctcggactca | gctcccggag | caacccagct | gcggaggcaa | cggcagtgct | gctcctccag | 180 |
| cgaaggacag | caggcaggca | gacagacaga | ggtcctggga | ctggaaggcc | tcagccccca | 240 |
| gccactgggc | tgggcctggc | ccaatggcct | ttaatgacct | cctgcagcag | gtggggggtg | 300 |
| tcggccgctt | ccagcagatc | caggtcaccc | tggtggtcct | ccccctgctc | ctgatggctt | 360 |
| ctcacaacac | cctgcagaac | ttcactgctg | ccatccctac | ccaccactgc | cgcccgcctg | 420 |
| ccgatgccaa | cctcagcaag | aacgggggc | tggaggtctg | gctgccccgg | gacaggcagg | 480 |
| ggcagcctga | gtcctgcctc | cgcttcacct | ccccgcagtg | gggactgccc | tttctcaatg | 540 |
| gcacagaagc | caatggcaca | ggggccacag | agccctgcac | cgatggctgg | atctatgaca | 600 |
| acagcacctt | cccatctacc | atcgtgactg | agtgggacct | tgtgtgctct | cacagggccc | 660 |
| tacgccagct | ggcccagtcc | ttgtacatgg | tggggtgct | gctcggagcc | atggtgttcg | 720 |
| gctaccttgc | agacaggcta | ggccgccgga | aggtactcat | cttgaactac | ctgcagacag | 780 |
| ctgtgtcagg | gacctgcgca | gccttcgcac | ccaacttccc | catctactgc | gccttccggc | 840 |
| tcctctcggg | catggctctg | gctggcatct | ccctcaactg | catgacactg | aatgtggagt | 900 |
| ggatgcccat | tcacacacgg | gcctgcgtgg | gcaccttgat | tggctatgtc | tacagcctgg | 960 |
| gccagttcct | cctggctggt | gtggcctacg | ctgtgcccca | ctggcgccac | ctgcagctac | 1020 |
| tggtctctgc | gccttttttt | gccttcttca | tctactcctg | gttcttcatt | gagtcggccc | 1080 |
| gctggcactc | ctcctccggg | aggctggacc | tcaccctgag | ggccctgcag | agagtcgccc | 1140 |
| ggatcaatgg | gaagcgggaa | gaaggagcca | aattgagtat | ggaggtactc | cgggccagtc | 1200 |
| tgcagaagga | gctgaccatg | ggcaaaggcc | aagcatcggc | catggagctg | ctgcgctgcc | 1260 |
| ccaccctccg | ccaactcttc | ctctgcctct | ccatgctgtg | gtttgccact | agctttgcat | 1320 |
| actatgggct | ggtcatggac | ctgcagggct | ttggagtcag | catctaccta | atccaggtga | 1380 |
| tctttggtgc | tgtggacctg | cctgccaagc | ttgtgggctt | ccttgtcatc | aactccctgg | 1440 |
| gtcgccggcc | tgcccagatg | gctgcactgc | tgctggcagg | catctgcatc | ctgctcaatg | 1500 |
| gggtgatacc | ccaggaccag | tccattgtcc | gaacctctct | tgctgtgctg | gggaagggtt | 1560 |

| | |
|---|---|
| gtctggctgc ctccttcaac tgcatcttcc tgtatactgg ggaactgtat cccacaatga | 1620 |
| tccggcagac aggcatggga atgggcagca ccatggcccg agtgggcagc atcgtgagcc | 1680 |
| cactggtgag catgactgcc gagctctacc cctccatgcc tctcttcatc tacggtgctg | 1740 |
| ttcctgtggc cgccagcgct gtcactgtcc cagagaccct gggccagcca ctgccagaca | 1800 |
| cggtgcagga cctggagagc aggaaaggga acagacgcg acagcaacaa gagcaccaga | 1860 |
| agtatatggt cccactgcag gcctcagcac aagagaagaa tggactctga ggactgagaa | 1920 |
| ggggccttac agaaccctaa agggaggaa gtcctacag gtctccggcc acccacacaa | 1980 |
| ggaggaggaa gaggaaatgg tgacccaagt gtggggttg tggttcagga aagcatcttc | 2040 |
| ccaggggtcc acctcccttt ataaacccca ccagaaccac atcattaaaa ggtttgactg | 2100 |
| cgcaccaaaa aaaaaaaaa a | 2121 |

<210> SEQ ID NO 2
<211> LENGTH: 1950
<212> TYPE: DNA
<213> ORGANISM: Homo sapiens

<400> SEQUENCE: 2

| | |
|---|---|
| ctgcacctga agcatttggt gggtgagcag catgggcttt gaggagctgc tggagcaggt | 60 |
| gggcggcttt gggcccttcc aactgcggaa tgtggcactg ctggccctgc ccgagtgct | 120 |
| gctaccactg cacttcctcc tgcccatctt cctggctgcc gtgcctgccc accgatgtgc | 180 |
| cctgccgggt gcccctgcca acttcagcca tcaggatgtg tggctggagg cccatcttcc | 240 |
| ccgggagcct gatggcacgc tcagctcctg cctccgcttt gcctatcccc aggctctccc | 300 |
| caacaccacg ttgggggaag aaaggcagag ccgtggggag ctggaggatg aacctgccac | 360 |
| agtgccctgc tctcagggct gggagtacga ccactcagaa ttctcctcta ccattgcaac | 420 |
| tgagtgggat ctggtgtgtg agcagaaagg tctgaacaga gctgcgtcca ctttcttctt | 480 |
| cgccggtgtg ctggtggggg ctgtggcctt tggatatctg tccgacaggt ttgggcggcg | 540 |
| gcgtctgctg ctggtagcct acgtgagtac cctggtgctg ggcctggcat ctgcagcctc | 600 |
| cgtcagctat gtaatgtttg ccatcacccg cacccttact ggctcagccc tggctggttt | 660 |
| taccatcatc gtgatgccac tggagctgga gtggctggat gtggagcacc gccgtggc | 720 |
| tggagtcctg agcagcacct tctggacagg gggcgtgatg ctgctggcac tggttgggta | 780 |
| cctgatacgg gactggcgat ggcttctgct agctgtcacc ctgccttgtg ccccaagcat | 840 |
| cctcagcctc tggtgggtgc ctgagtctgc acgctggctt ctgacccaag gccatgtgaa | 900 |
| agaggcccac aggtacttgc tccactgtgc caggctcaat gggcggccag tgtgtgagga | 960 |
| cagcttcagc caggaggctg tgagcaaagt ggccgccggg aacgggtgg tccgaagacc | 1020 |
| ttcataccta gacctgttcc gcacaccacg gctccgacac atctcactgt gctgcgtggt | 1080 |
| ggtgtggttc ggagtgaact ctcctatta cggcctgagt ctggatgtgt cggggctggg | 1140 |
| gctgaacgtg taccagacac agctgttgtt cggggctgtg gaactgccct caagctgct | 1200 |
| ggtctacttg tcggtgcgct acgcaggacg ccgcctcacg caagccggga cactgctggg | 1260 |
| cacggccctg cgcttcggca ctagactgct agtgtcctcc gatatgaagt cctggagcac | 1320 |
| tgtcctggca gtgatgggga aagcttttc tgaagctgcc ttcaccactg cctacctgtt | 1380 |
| cacttcagag ttgtacccta cggtgctcag acagacaggg atgggctga ctgcactggt | 1440 |
| gggccggctc gggggctctt tggccccact ggcggccttg ctggatggag tgtggctgtc | 1500 |
| actgcccaag cttacttatg gggggatcgc cctgctggct gccggcaccg ccctcctgct | 1560 |

-continued

```
gccagagacg aggcaggcac agctgccaga gaccatccag gacgtggaga gaaagagaga    1620
tggtgctaaa gaaaggacta gcatatgaga cttctggtac caatgggagct ggtgggcatg   1680 ctgtccactg tgtggtgcta ggactgccaa tgccaggccc aagggacaaa agaacagag    1740 cttttttgttc tcatggctgg ccctgctacc tccgaggcac cctgcagggc aatgcatgtc  1800
atcccaaccc ccacactccc catcctccaa cccactggtc tcatgccaa agaagagttg   1860 aaggcatggg agccaacatt ttattgaaga agccacagag gctgaaattc aataaacaca   1920
agttttatga gtaaaaaaaa aaaaaaaaa                                      1950

<210> SEQ ID NO 3
<211> LENGTH: 2501
<212> TYPE: DNA
<213> ORGANISM: Homo sapiens

<400> SEQUENCE: 3
ctgcacctga agcatttggt gggtgagcag catgggcttt gaggagctgc tggagcaggt    60
gggcggcttt gggcccttcc aactgcggaa tgtggcactg ctggccctgc ccgagtgct   120 gctaccactg cacttcctcc tgcccatctt cctggctgcc gtgcctgccc accgatgtgc  180
cctgccgggt gcccctgcca acttcagcca tcaggatgtg tggctggagg cccatcttcc  240
ccgggagcct gatggcacgc tcagctcctg cctccgcttt gcctatcccc aggctctccc  300
caacaccacg ttgggggaag aaaggcagag ccgtggggag ctggaggatg aacctgccac  360
agtgccctgc tctcagggct gggagtacga ccactcagaa ttctcctcta ccattgcaac  420
tgagtgggat ctggtgtgtg agcagaaagg tctgaacaga gctgcgtcca ctttcttctt  480
cgccggtgtg ctggtggggg ctgtggcctt tggatatctg tccgacaggt ttgggcggcg  540
gcgtctgctg ctggtagcct acgtgagtac cctggtgctg ggcctggcat ctgcagcctc  600
cgtcagctat gtaatgtttg ccatcacccg cacccttact ggctcagccc tggctggttt  660
taccatcatc gtgatgccac tggagctgga gtggctggat gtggagcacc gcaccgtggc  720
tggagtcctg agcagcacct tctggacagg gggcgtgatg ctgctggcac tggttgggta  780
cctgatacgg gactggcgat ggcttctgct agctgtcacc ctgccttgtg ccccaagcat  840
cctcagcctc tggtgggtgc ctgagtctgc acgctggctt ctgacccaag gccatgtgaa  900
agaggcccac aggtacttgc tccactgtgc caggctcaat gggcggccag tgtgtgagga  960
cagcttcagc caggaggctg tgagcaaagt ggccgccggg gaacgggtgg tccgaagacc 1020
ttcataccta gacctgttcc gcacaccacg gctccgacac atctcactgt gctgcgtggt 1080
ggtgtggttc ggagtgaact ctcctattta cggcctgagt ctggatgtgt cggggctggg 1140
gctgaacgtg taccagacac agctgttgtt cggggctgtg aactgccct ccaagctgct 1200 ggtctacttg tcggtgcgct acgcaggacg ccgcctcacg caagccggga cactgctggg 1260
cacggccctg cgcttcggca ctagactgct agtgtcctcc gatatgaagt cctggagcac 1320
tgtcctggca gtgatgggga agctttttc tgaagctgcc ttcaccactg cctacctgtt 1380
cacttcagag ttgtaccctc cggtgctcag acagacaggg atgggctga ctgcactggt  1440 gggccggctg gggggctctt tggccccact ggcggcttg ctggatggag tgtggctgtc 1500
actgcccaag cttacttatg gggggatcgc cctgctggct gccggcaccg ccctcctgct 1560
gccagagacg aggcaggcac agctgccaga gaccatccag gacgtggaga gaaagagtgc 1620
cccaaccagt cttcaggagg aagagatgcc catgaagcag gtccagaact aagtgggagt 1680
```

-continued

| | |
|---|---|
| ggaggcaggc cctccacaga agctctgcag caggggctgg gagagcagaa gggcaggccc | 1740 |
| tgcaactcag gctgggagta tcgaaccctc tgcctagggc cggagttgct gccagtaccc | 1800 |
| gctccctctg ctcatccatc cttgattatt tggcttctag aacagttga cttcccagaa | 1860 |
| tgcagtgggc tgctgggcac ccctctcacg gttggggagg attctgtaaa taaaggtgcc | 1920 |
| ccttgggttg gggcaatggt gacgagctgt gggaagagcc ctggatagga agccactgag | 1980 |
| tctgccctgg gctctgataa aaccttcacc attaacttgc tgtgtgacct tgggcatgtg | 2040 |
| gctttccctc tctggcctca gtctgttcat ctcccaaatg gataatgaag cctcttggga | 2100 |
| ggccctacca taggatctgt tgccatgctc aaatgagtta ctgaataagg tgcttctgct | 2160 |
| tcttctagag atggtgctaa agaaaggact agcatatgag acttctggta ccaatggggc | 2220 |
| tggtgggcat gctgtccact gtgtggtgct aggactgcca atgccaggcc caagggacaa | 2280 |
| aaagaacaga gcttttttgtt ctcatggctg gccctgctac ctccgaggca ccctgcaggg | 2340 |
| caatgcatgt catcccaacc cccacactcc ccatcctcca acccactggt ctcatgccca | 2400 |
| aagaagagtt gaaggcatgg gagccaacat tttattgaag aagccacaga ggctgaaatt | 2460 |
| caataaacac aagtttttatg agtaaaaaaa aaaaaaaaa a | 2501 |

<210> SEQ ID NO 4
<211> LENGTH: 2121
<212> TYPE: DNA
<213> ORGANISM: Homo sapiens

<400> SEQUENCE: 4

| | |
|---|---|
| gcagggacct caactacact gatcaccagc cccatcggat ccagacccgg ccaccagtgc | 60 |
| catgaccttc tcggagatcc tggaccgtgt gggaagcatg ggccatttcc agttcctgca | 120 |
| tgtagccata ctgggcctcc cgatcctcaa catggccaac cacaacctgc tgcagatctt | 180 |
| cacagccgcc acccctgtcc accactgtcg cccgccccac aatgcctcca cagggccttg | 240 |
| ggtgctcccc atgggcccaa atgggaagcc tgagaggtgc ctccgttttg tacatccgcc | 300 |
| caatgccagc ctgcccaatg acacccagag gccatggag ccatgcctgg atggctgggt | 360 |
| ctacaacagc accaaggact ccattgtgac agagtgggac ttggtgtgca actccaacaa | 420 |
| actgaaggag atggcccagt ctatcttcat ggcaggtata ctgattggag ggctcgtgct | 480 |
| tggagacctg tctgacaggt ttggccgcag gcccatcctg acctgcagct acctgctgct | 540 |
| ggcagccagc ggctccggtg cagccttcag ccccaccttc cccatctaca tggtcttccg | 600 |
| cttcctgtgt ggctttggca tctcaggcat taccctgagc accgtcatct tgaatgtgga | 660 |
| atgggtgcct acccggatgc gggccatcat gtcgacagca ctcgggtact gctacacctt | 720 |
| tggccagttc attctgcccg gcctggccta cgccatcccc cagtggcgtt ggctgcagtt | 780 |
| aactgtgtcc attcccttct tcgtcttctt cctatcatcc tggtggacac cagagtccat | 840 |
| acgctggttg gtcttgtctg gaaagtcctc gaaggccctg aagatactcc ggcgggtggc | 900 |
| tgtcttcaat ggcaagaagg aagagggaga aggctcagc ttggaggagc tcaaactcaa | 960 |
| cctgcagaag gagatctcct tggccaaggc caagtacacc gcaagtgacc tgttccggat | 1020 |
| acccatgctg cgccgcatga ccttctgtct ttccctggcc tggtttgcta ccggttttgc | 1080 |
| ctactatagt ttggctatgg gtgtggaaga atttggagtc aacctctaca tcctccagat | 1140 |
| catctttggt ggggtcgatg tcccagccaa gttcatcacc atcctctcct taagctacct | 1200 |
| gggccggcat accactcagg ccgctgccct gctcctggca ggaggggcca tcttggctct | 1260 |
| caccttttgtg cccttggact tgcagaccgt gaggacagta ttggctgtgt ttgggaaggg | 1320 |

-continued

```
atgcctatcc agctccttca gctgcctctt cctctacaca agtgaattat accccacagt    1380
catcaggcaa acaggtatgg gcgtaagtaa cctgtggacc cgcgtgggaa gcatggtgtc    1440
cccgctggtg aaaatcacgg gtgaggtaca gcccttcatc cccaatatca tctacgggat    1500
caccgccctc ctcgggggca gtgctgccct cttcctgcct gagaccctga atcagccctt    1560
gccagagact atcgaagacc tggaaaactg gtccctgcgg gcaaagaagc caaagcagga    1620
gccagaggtg gaaaaggcct cccagaggat ccctctacag cctcacggac caggcctggg    1680
ctccagctga ggacaacgga accccctttc cctgccctcc agagactgat cctagccagg    1740
caccttagga gtatagggag gccccatata ggtccatcct cctaggatga agccttctga    1800
gagcttggtg aaggtgtctc catcaccacc accagagcct cctgcccagc cctggccagt    1860
tcaaaggttc aagccatccc tgcccttgtt ctccctgcaa cccaagccct gccattcttc    1920
tgtctagccc ttccccactg gccaacttcc cccactgtcc cggtcctctt ccctgaggt    1980 cccctgatat ccctggctc agtcctaaca agactgagtc ttaacaagat gagaagtcct    2040
ccccttcttg cctcccacac ttttctttga tgggaggttt caataaacag cgataagaac    2100
tctaaaaaaa aaaaaaaaa a    2121
```

<210> SEQ ID NO 5
<211> LENGTH: 1977
<212> TYPE: DNA
<213> ORGANISM: Homo sapiens

<400> SEQUENCE: 5

```
caaattattt cttacgtgac tttagagaaa acggctacct atctgacccc aaaacgactt      60
gaggaaactg tttccacggt cctgctgcag gggggaagca cagtcgtcaa gaagagagtg     120
gggtcaggat caaaacacat ttagtgtgac ttagggaaag aaaacatttt ccctctttga     180
acctctctgg atacagtcat tttgcctcta cttgaggatc aactgttcaa cctcaatggc     240
ctttcaggac ctcctgggtc acgctggtga cctgtggaga ttccagatcc ttcagactgt     300
ttttctctca atctttgctg ttgctacata ccttcatttt atgctggaga acttcactgc     360
attcatacct ggccatcgct gctgggtcca catcctggac aatgacactg tctctgacaa     420
tgacactggg gccctcagcc aagatgcact cttgagaatc tccatcccac tggactcaaa     480
catgaggcca gagaagtgtc gtcgctttgt tcatcctcag tggcagctcc ttcacctgaa     540
tgggaccttc cccaacacaa gtgacgcaga catggagccc tgtgtggatg ctgggtgta     600 tgacagaatc tccttctcat ccaccatcgg tgacctgaag tgggatctgg tatgtgactc     660
tcaatcactg acttcagtgg ctaaatttgt attcatggct ggaatgatgt tgggaggcat     720
cttaggcgtt catttatcag acaggtttgg gagaagtttc gtgctcagat ggtgttacct     780
ccaggttgcc attgttggca cttgtgcagc gttggctccc actttcctca tttactgctc     840
agtacgcttc ttgtctggga ttgctgcaat gagcttcata acaaatacta ttatgttaat     900
agccgagtgg gcaacacaca gattccaggc catgggaatt acattgggaa tgtgcccttc     960
tggtattgca tttatgaccc tggcaggcct ggcttttgcc attcgagact ggcatatcct    1020
ccagctggtg gtgtctgtac catactttgt gatctttctg acctcaagtt ggctgctaga    1080
gtctgctcgg tggctcatta tcaacaataa accagaggaa ggcttaaagg aacttagaaa    1140
agctgcacac aggagtggaa tgaagaatgc cagagacacc ctaaccctgg agattttgaa    1200
atccaccatg aaaaaagaac tggaggcagc acaaaaaaaa aaaccttctc tgtgtgaaat    1260
```

-continued

| | |
|---|---|
| gctccacatg cccaacatat gtaaaaggat ctccctcctg tccttacga gatttgcaaa | 1320 |
| ctttatggcc tattttggcc ttaatctcca tgtccagcat ctggggaaca atgttttcct | 1380 |
| gttgcagact ctctttggtg cagtcatcct cctggccaac tgtgttgcac cttgggcact | 1440 |
| gaaatacatg aaccgtcgag caagccagat gcttctcatg ttcctactgg caatctgcct | 1500 |
| tctggccatc atatttgtgc cacaagaaat gcagacgctg cgtgaggttt tggcaacact | 1560 |
| gggcttagga gcgtctgctc ttgccaatac ccttgctttt gcccatggaa atgaagtaat | 1620 |
| tcccaccata atcagggcaa gagctatggg gatcaatgca acctttgcta atatagcagg | 1680 |
| agccctggct cccctcatga tgatcctaag tgtgtattct ccaccctgc cctggatcat | 1740 |
| ctatggagtc ttccccttca tctctggctt gctttcctc ctccttcctg aaaccaggaa | 1800 |
| caagcctctg tttgacacca tccaggatga gaaaaatgag agaaaagacc ccagagaacc | 1860 |
| aaagcaagag gatccgagag tggaagtgac gcagttttaa ggaattccag gagctgactg | 1920 |
| ccgatcaatg agccagatga agggaacaat caggactatt cctagacact agcaaaa | 1977 |

<210> SEQ ID NO 6
<211> LENGTH: 2684
<212> TYPE: DNA
<213> ORGANISM: Homo sapiens

<400> SEQUENCE: 6

| | |
|---|---|
| ctcctgatag caaagaact gaggaagctc tttccactac ggctgtattg cactggtgag | 60 |
| tccgggccca tggatgagaa attgatgcga ggatcaatac aagcttaatt tgaattaata | 120 |
| aaaggaaata ttttctccct ttgaacttat ctccgtaaag ccattgtgcc tcctcttggg | 180 |
| ggtcacgtgt tcacaatcaa tggccttga ggagctcttg agtcaagttg gaggccttgg | 240 |
| gagatttcag atgcttcatc tggtttttat tcttccctct ctcatgttat taatccctca | 300 |
| tatactgcta gagaactttg ctgcagccat tcctggtcat cgttgctggg tccacatgct | 360 |
| ggacaataat actggatctg gtaatgaaac tggaatcctc agtgaagatg ccctcttgag | 420 |
| aatctctatc ccactagact caaatctgag gccagagaag tgtcgtcgct ttgtccatcc | 480 |
| ccagtggcag cttcttcacc tgaatgggac tatccacagc acaagtgagg cagacacaga | 540 |
| accctgtgtg gatggctggg tatatgatca aagctacttc ccttcgacca ttgtgactaa | 600 |
| gtgggacctg gtatgtgatt atcagtcact gaaatcagtg gttcaattcc tacttctgac | 660 |
| tggaatgctg gtgggaggca tcataggtgg ccatgtctca gacaggtttg ggcgaagatt | 720 |
| tattctcaga tggtgtttgc tccagcttgc cattactgac acctgcgctg ccttcgctcc | 780 |
| caccttccct gtttactgtg tactacgctt cttggcaggt ttttcttcca tgatcattat | 840 |
| atcaaataat tctttgccca ttactgagtg gataaggccc aactctaaag ccctggtagt | 900 |
| aatattgtca tctggtgccc ttagtattgg acagataatc ctgggaggct ggcttatgt | 960 |
| cttccgagac tggcaaaccc tgcacgtggt ggcgtcagta cctttccttg gcctccttct | 1020 |
| ccttcaaagg tggctggtgg aatctgctcg gtggttgata atcaccaata aactagatga | 1080 |
| gggcttaaag gcacttagaa aagttgcacg cacaaatgga ataaagaatg ctgaagaaac | 1140 |
| cctgaacata gaggttgtaa gatccaccat gcaggaggag ctggatgcag cacagaccaa | 1200 |
| aactactgtg tgtgacttgt ccgcaaccc cagtatgcgt aaaaggatct gtatcctggt | 1260 |
| atttttgaga tttgcaaaca caataccttt ttatggtacc atggtcaatc ttcagcatgt | 1320 |
| ggggagcaac attttcctgt tgcaggtact ttatggagct gtcgctctca tagttcgatg | 1380 |
| tcttgctctt ttgacactaa atcatatggg ccgtcgaata agccagatat tgttcatgtt | 1440 |

-continued

```
cctggtgggc ctttccattt tggccaacac gtttgtgccc aaagaaatgc agaccctgcg    1500
tgtggctttg gcatgtctgg gaatcggctg ttctgctgct actttttcca gtgttgctgt    1560
tcacttcatt gaactcatcc ccactgttct cagggcaaga gcttcaggaa tagatttaac    1620
ggctagtagg attggagcag cactggctcc cctcttgatg accttaacgg tattttttac    1680
cactttgcca tggatcattt atggaatctt ccccatcatt ggtggcctta ttgtcttcct    1740
cctaccagaa accaagaatc tgcctttgcc tgacaccatc aaggatgtgg aaaatcaaaa    1800
aaaaaatctc aaggaaaagg cataaaaatg attgctacac aaaagtgacc aaattttaag    1860
aagccttcat gagctgattg gtggggaaat tcagaaaaaa aaatacagga aagaacaca     1920 ccagaagggt ttttttccct acaaccagca agaacatata ttagatacat gaatctcaat    1980
tataattatg gcattaattt gcattttatt tcaaaattaa cttgtgggga catgtaatct    2040
cttgagcaat ctgatatttt tgggaagtcc tttaaaaagt tacaaattta tcaataaatt    2100
actagtagat aagatgattc agaaacaaag gaaaatcaca gaattaggat gtggctggct    2160
tggtgtatga agcaccatgt gatgaattca taagttgca  aaagtcaaaa caatactgta    2220
catgcaacca gaaatcaaat taaatccaga aatagagacc tatataaatg catttaatac    2280
atgatacttt tgcatatta agccattgga aaacggaagg attagatact taaataacat     2340
tgctatctct ttgtaaatac agtcactaaa tgatgttagt tacttttcca tggtggaatt    2400
ttaattactt tttcttttgta atttttctct ctgtatattt taaacaaata gctggtatag    2460
tttacaatat tataaagata ttgttcaaat tgaagggcaa aggccaggtt cagcaatttt    2520
caaactgtat gtacatttaa taaataact ataaattaaa aaattatatt tcaaatgatg     2580
tgactaataa atgaaagtac atatagtagt aaagtaattt caggcaaacc tatataacca    2640
aaatataaac tttcatttta aacagcaaaa aaaaaaaaaa aaaa                     2684
```

<210> SEQ ID NO 7
<211> LENGTH: 550
<212> TYPE: PRT
<213> ORGANISM: Homo sapiens

<400> SEQUENCE: 7

Met Ala Phe Asn Asp Leu Leu Gln Gln Val Gly Val Gly Arg Phe
1               5                   10                  15

Gln Gln Ile Gln Val Thr Leu Val Val Leu Pro Leu Leu Met Ala
            20                  25                  30

Ser His Asn Thr Leu Gln Asn Phe Thr Ala Ala Ile Pro Thr His His
        35                  40                  45

Cys Arg Pro Pro Ala Asp Ala Asn Leu Ser Lys Asn Gly Gly Leu Glu
    50                  55                  60

Val Trp Leu Pro Arg Asp Arg Gln Gly Gln Pro Glu Ser Cys Leu Arg
65                  70                  75                  80

Phe Thr Ser Pro Gln Trp Gly Leu Pro Phe Leu Asn Gly Thr Glu Ala
                85                  90                  95

Asn Gly Thr Gly Ala Thr Glu Pro Cys Thr Asp Gly Trp Ile Tyr Asp
            100                 105                 110

Asn Ser Thr Phe Pro Ser Thr Ile Val Thr Glu Trp Asp Leu Val Cys
        115                 120                 125

Ser His Arg Ala Leu Arg Gln Leu Ala Gln Ser Leu Tyr Met Val Gly
    130                 135                 140

Val Leu Leu Gly Ala Met Val Phe Gly Tyr Leu Ala Asp Arg Leu Gly

-continued

```
                145                 150                 155                 160
Arg Arg Lys Val Leu Ile Leu Asn Tyr Leu Gln Thr Ala Val Ser Gly
                    165                 170                 175

Thr Cys Ala Ala Phe Ala Pro Asn Phe Pro Ile Tyr Cys Ala Phe Arg
                180                 185                 190

Leu Leu Ser Gly Met Ala Leu Ala Gly Ile Ser Leu Asn Cys Met Thr
            195                 200                 205

Leu Asn Val Glu Trp Met Pro Ile His Thr Arg Ala Cys Val Gly Thr
        210                 215                 220

Leu Ile Gly Tyr Val Tyr Ser Leu Gly Gln Phe Leu Leu Ala Gly Val
225                 230                 235                 240

Ala Tyr Ala Val Pro His Trp Arg His Leu Gln Leu Leu Val Ser Ala
                    245                 250                 255

Pro Phe Phe Ala Phe Phe Ile Tyr Ser Trp Phe Phe Ile Glu Ser Ala
                260                 265                 270

Arg Trp His Ser Ser Ser Gly Arg Leu Asp Leu Thr Leu Arg Ala Leu
            275                 280                 285

Gln Arg Val Ala Arg Ile Asn Gly Lys Arg Glu Glu Gly Ala Lys Leu
        290                 295                 300

Ser Met Glu Val Leu Arg Ala Ser Leu Gln Lys Glu Leu Thr Met Gly
305                 310                 315                 320

Lys Gly Gln Ala Ser Ala Met Glu Leu Leu Arg Cys Pro Thr Leu Arg
                    325                 330                 335

His Leu Phe Leu Cys Leu Ser Met Leu Trp Phe Ala Thr Ser Phe Ala
                340                 345                 350

Tyr Tyr Gly Leu Val Met Asp Leu Gln Gly Phe Gly Val Ser Ile Tyr
            355                 360                 365

Leu Ile Gln Val Ile Phe Gly Ala Val Asp Leu Pro Ala Lys Leu Val
        370                 375                 380

Gly Phe Leu Val Ile Asn Ser Leu Gly Arg Arg Pro Ala Gln Met Ala
385                 390                 395                 400

Ala Leu Leu Leu Ala Gly Ile Cys Ile Leu Leu Asn Gly Val Ile Pro
                    405                 410                 415

Gln Asp Gln Ser Ile Val Arg Thr Ser Leu Ala Val Leu Gly Lys Gly
                420                 425                 430

Cys Leu Ala Ala Ser Phe Asn Cys Ile Phe Leu Tyr Thr Gly Glu Leu
            435                 440                 445

Tyr Pro Thr Met Ile Arg Gln Thr Gly Met Gly Met Gly Ser Thr Met
        450                 455                 460

Ala Arg Val Gly Ser Ile Val Ser Pro Leu Val Ser Met Thr Ala Glu
465                 470                 475                 480

Leu Tyr Pro Ser Met Pro Leu Phe Ile Tyr Gly Ala Val Pro Val Ala
                    485                 490                 495

Ala Ser Ala Val Thr Val Leu Leu Pro Glu Thr Leu Gly Gln Pro Leu
                500                 505                 510

Pro Asp Thr Val Gln Asp Leu Glu Ser Arg Lys Gly Lys Gln Thr Arg
            515                 520                 525

Gln Gln Gln Glu His Gln Lys Tyr Met Val Pro Leu Gln Ala Ser Ala
        530                 535                 540

Gln Glu Lys Asn Gly Leu
545                 550
```

<210> SEQ ID NO 8

<211> LENGTH: 546
<212> TYPE: PRT
<213> ORGANISM: Homo sapiens

<400> SEQUENCE: 8

```
Met Gly Phe Glu Glu Leu Leu Glu Gln Val Gly Phe Gly Pro Phe
 1               5                  10                  15

Gln Leu Arg Asn Val Ala Leu Leu Ala Leu Pro Arg Val Leu Leu Pro
             20                  25                  30

Leu His Phe Leu Leu Pro Ile Phe Leu Ala Ala Val Pro Ala His Arg
             35                  40                  45

Cys Ala Leu Pro Gly Ala Pro Ala Asn Phe Ser His Gln Asp Val Trp
         50                  55                  60

Leu Glu Ala His Leu Pro Arg Glu Pro Asp Gly Thr Leu Ser Ser Cys
 65                  70                  75                  80

Leu Arg Phe Ala Tyr Pro Gln Ala Leu Pro Asn Thr Thr Leu Gly Glu
                 85                  90                  95

Glu Arg Gln Ser Arg Gly Glu Leu Glu Asp Glu Pro Ala Thr Val Pro
            100                 105                 110

Cys Ser Gln Gly Trp Glu Tyr Asp His Ser Glu Phe Ser Ser Thr Ile
        115                 120                 125

Ala Thr Glu Trp Asp Leu Val Cys Glu Gln Lys Gly Leu Asn Arg Ala
    130                 135                 140

Ala Ser Thr Phe Phe Phe Ala Gly Val Leu Val Gly Ala Val Ala Phe
145                 150                 155                 160

Gly Tyr Leu Ser Asp Arg Phe Gly Arg Arg Leu Leu Leu Val Ala
                165                 170                 175

Tyr Val Ser Thr Leu Val Leu Gly Leu Ala Ser Ala Ala Ser Val Ser
                180                 185                 190

Tyr Val Met Phe Ala Ile Thr Arg Thr Leu Thr Gly Ser Ala Leu Ala
            195                 200                 205

Gly Phe Thr Ile Ile Val Met Pro Leu Glu Leu Glu Trp Leu Asp Val
    210                 215                 220

Glu His Arg Thr Val Ala Gly Val Leu Ser Ser Thr Phe Trp Thr Gly
225                 230                 235                 240

Gly Val Met Leu Leu Ala Leu Val Gly Tyr Leu Ile Arg Asp Trp Arg
                245                 250                 255

Trp Leu Leu Leu Ala Val Thr Leu Pro Cys Ala Pro Ser Ile Leu Ser
                260                 265                 270

Leu Trp Trp Val Pro Glu Ser Ala Arg Trp Leu Leu Thr Gln Gly His
            275                 280                 285

Val Lys Glu Ala His Arg Tyr Leu Leu His Cys Ala Arg Leu Asn Gly
    290                 295                 300

Arg Pro Val Cys Glu Asp Ser Phe Ser Gln Glu Ala Val Ser Lys Val
305                 310                 315                 320

Ala Ala Gly Glu Arg Val Val Arg Arg Pro Ser Tyr Leu Asp Leu Phe
                325                 330                 335

Arg Thr Pro Arg Leu Arg His Ile Ser Leu Cys Cys Val Val Val Trp
            340                 345                 350

Phe Gly Val Asn Phe Ser Tyr Tyr Gly Leu Ser Leu Asp Val Ser Gly
        355                 360                 365

Leu Gly Leu Asn Val Tyr Gln Thr Gln Leu Leu Phe Gly Ala Val Glu
    370                 375                 380

Leu Pro Ser Lys Leu Leu Val Tyr Leu Ser Val Arg Tyr Ala Gly Arg
```

-continued

```
385                 390                 395                 400

Arg Leu Thr Gln Ala Gly Thr Leu Gly Thr Ala Leu Ala Phe Gly
                405                 410                 415

Thr Arg Leu Leu Val Ser Ser Asp Met Lys Ser Trp Ser Thr Val Leu
            420                 425                 430

Ala Val Met Gly Lys Ala Phe Ser Glu Ala Ala Phe Thr Thr Ala Tyr
            435                 440                 445

Leu Phe Thr Ser Glu Leu Tyr Pro Thr Val Leu Arg Gln Thr Gly Met
            450                 455                 460

Gly Leu Thr Ala Leu Val Gly Arg Leu Gly Ser Leu Ala Pro Leu
465                 470                 475                 480

Ala Ala Leu Leu Asp Gly Val Trp Leu Ser Leu Pro Lys Leu Thr Tyr
                485                 490                 495

Gly Gly Ile Ala Leu Leu Ala Ala Gly Thr Ala Leu Leu Pro Glu
            500                 505                 510

Thr Arg Gln Ala Gln Leu Pro Glu Thr Ile Gln Asp Val Glu Arg Lys
            515                 520                 525

Ser Ala Pro Thr Ser Leu Gln Glu Glu Met Pro Met Lys Gln Val
            530                 535                 540

Gln Asn
545

<210> SEQ ID NO 9
<211> LENGTH: 538
<212> TYPE: PRT
<213> ORGANISM: Homo sapiens

<400> SEQUENCE: 9

Met Gly Phe Glu Glu Leu Leu Glu Gln Val Gly Gly Phe Gly Pro Phe
 1               5                  10                  15

Gln Leu Arg Asn Val Ala Leu Leu Ala Leu Pro Arg Val Leu Leu Pro
            20                  25                  30

Leu His Phe Leu Leu Pro Ile Phe Leu Ala Ala Val Pro Ala His Arg
        35                  40                  45

Cys Ala Leu Pro Gly Ala Pro Ala Asn Phe Ser His Gln Asp Val Trp
 50                  55                  60

Leu Glu Ala His Leu Pro Arg Glu Pro Asp Gly Thr Leu Ser Ser Cys
65                  70                  75                  80

Leu Arg Phe Ala Tyr Pro Gln Ala Leu Pro Asn Thr Thr Leu Gly Glu
                85                  90                  95

Glu Arg Gln Ser Arg Gly Glu Leu Glu Asp Glu Pro Ala Thr Val Pro
            100                 105                 110

Cys Ser Gln Gly Trp Glu Tyr Asp His Ser Glu Phe Ser Ser Thr Ile
        115                 120                 125

Ala Thr Glu Trp Asp Leu Val Cys Glu Gln Lys Gly Leu Asn Arg Ala
130                 135                 140

Ala Ser Thr Phe Phe Ala Gly Val Leu Val Gly Ala Val Ala Phe
145                 150                 155                 160

Gly Tyr Leu Ser Asp Arg Phe Gly Arg Arg Leu Leu Leu Val Ala
                165                 170                 175

Tyr Val Ser Thr Leu Val Leu Gly Leu Ala Ser Ala Ala Ser Val Ser
            180                 185                 190

Tyr Val Met Phe Ala Ile Thr Arg Thr Leu Thr Gly Ser Ala Leu Ala
            195                 200                 205
```

-continued

```
Gly Phe Thr Ile Ile Val Met Pro Leu Glu Leu Glu Trp Leu Asp Val
            210                 215                 220

Glu His Arg Thr Val Ala Gly Val Leu Ser Ser Thr Phe Trp Thr Gly
225                 230                 235                 240

Gly Val Met Leu Leu Ala Leu Val Gly Tyr Leu Ile Arg Asp Trp Arg
                245                 250                 255

Trp Leu Leu Ala Val Thr Leu Pro Cys Ala Pro Ser Ile Leu Ser
            260                 265                 270

Leu Trp Trp Val Pro Glu Ser Ala Arg Trp Leu Leu Thr Gln Gly His
        275                 280                 285

Val Lys Glu Ala His Arg Tyr Leu Leu His Cys Ala Arg Leu Asn Gly
    290                 295                 300

Arg Pro Val Cys Glu Asp Ser Phe Ser Gln Glu Ala Val Ser Lys Val
305                 310                 315                 320

Ala Ala Gly Glu Arg Val Val Arg Arg Pro Ser Tyr Leu Asp Leu Phe
                325                 330                 335

Arg Thr Pro Arg Leu Arg His Ile Ser Leu Cys Cys Val Val Val Trp
            340                 345                 350

Phe Gly Val Asn Phe Ser Tyr Tyr Gly Leu Ser Leu Asp Val Ser Gly
        355                 360                 365

Leu Gly Leu Asn Val Tyr Gln Thr Gln Leu Leu Phe Gly Ala Val Glu
    370                 375                 380

Leu Pro Ser Lys Leu Leu Val Tyr Leu Ser Val Arg Tyr Ala Gly Arg
385                 390                 395                 400

Arg Leu Thr Gln Ala Gly Thr Leu Leu Gly Thr Ala Leu Ala Phe Gly
                405                 410                 415

Thr Arg Leu Leu Val Ser Ser Asp Met Lys Ser Trp Ser Thr Val Leu
            420                 425                 430

Ala Val Met Gly Lys Ala Phe Ser Glu Ala Ala Phe Thr Thr Ala Tyr
        435                 440                 445

Leu Phe Thr Ser Glu Leu Tyr Pro Thr Val Leu Arg Gln Thr Gly Met
    450                 455                 460

Gly Leu Thr Ala Leu Val Gly Arg Leu Gly Gly Ser Leu Ala Pro Leu
465                 470                 475                 480

Ala Ala Leu Leu Asp Gly Val Trp Leu Ser Leu Pro Lys Leu Thr Tyr
                485                 490                 495

Gly Gly Ile Ala Leu Leu Ala Ala Gly Thr Ala Leu Leu Leu Pro Glu
            500                 505                 510

Thr Arg Gln Ala Gln Leu Pro Glu Thr Ile Gln Asp Val Glu Arg Lys
        515                 520                 525

Arg Asp Gly Ala Lys Glu Arg Thr Ser Ile
    530                 535
```

<210> SEQ ID NO 10
<211> LENGTH: 542
<212> TYPE: PRT
<213> ORGANISM: Homo sapiens

<400> SEQUENCE: 10

```
Met Thr Phe Ser Glu Ile Leu Asp Arg Val Gly Ser Met Gly His Phe
1               5                   10                  15

Gln Phe Leu His Val Ala Ile Leu Gly Leu Pro Ile Leu Asn Met Ala
                20                  25                  30

Asn His Asn Leu Leu Gln Ile Phe Thr Ala Ala Thr Pro Val His His
            35                  40                  45
```

```
Cys Arg Pro Pro His Asn Ala Ser Thr Gly Pro Trp Val Leu Pro Met
 50                  55                  60
Gly Pro Asn Gly Lys Pro Glu Arg Cys Leu Arg Phe Val His Pro Pro
 65                  70                  75                  80
Asn Ala Ser Leu Pro Asn Asp Thr Gln Arg Ala Met Glu Pro Cys Leu
                 85                  90                  95
Asp Gly Trp Val Tyr Asn Ser Thr Lys Asp Ser Ile Val Thr Glu Trp
                100                 105                 110
Asp Leu Val Cys Asn Ser Asn Lys Leu Lys Glu Met Ala Gln Ser Ile
            115                 120                 125
Phe Met Ala Gly Ile Leu Ile Gly Gly Leu Val Leu Gly Asp Leu Ser
    130                 135                 140
Asp Arg Phe Gly Arg Arg Pro Ile Leu Thr Cys Ser Tyr Leu Leu Leu
145                 150                 155                 160
Ala Ala Ser Gly Ser Gly Ala Ala Phe Ser Pro Thr Phe Pro Ile Tyr
                165                 170                 175
Met Val Phe Arg Phe Leu Cys Gly Phe Gly Ile Ser Gly Ile Thr Leu
            180                 185                 190
Ser Thr Val Ile Leu Asn Val Glu Trp Val Pro Thr Arg Met Arg Ala
        195                 200                 205
Ile Met Ser Thr Ala Leu Gly Tyr Cys Tyr Thr Phe Gly Gln Phe Ile
    210                 215                 220
Leu Pro Gly Leu Ala Tyr Ala Ile Pro Gln Trp Arg Trp Leu Gln Leu
225                 230                 235                 240
Thr Val Ser Ile Pro Phe Phe Val Phe Phe Leu Ser Ser Trp Trp Thr
                245                 250                 255
Pro Glu Ser Ile Arg Trp Leu Val Leu Ser Gly Lys Ser Ser Lys Ala
            260                 265                 270
Leu Lys Ile Leu Arg Arg Val Ala Val Phe Asn Gly Lys Lys Glu Glu
    275                 280                 285
Gly Glu Arg Leu Ser Leu Glu Glu Leu Lys Leu Asn Leu Gln Lys Glu
290                 295                 300
Ile Ser Leu Ala Lys Ala Lys Tyr Thr Ala Ser Asp Leu Phe Arg Ile
305                 310                 315                 320
Pro Met Leu Arg Arg Met Thr Phe Cys Leu Ser Leu Ala Trp Phe Ala
                325                 330                 335
Thr Gly Phe Ala Tyr Tyr Ser Leu Ala Met Gly Val Glu Glu Phe Gly
            340                 345                 350
Val Asn Leu Tyr Ile Leu Gln Ile Ile Phe Gly Gly Val Asp Val Pro
        355                 360                 365
Ala Lys Phe Ile Thr Ile Leu Ser Leu Ser Tyr Leu Gly Arg His Thr
    370                 375                 380
Thr Gln Ala Ala Ala Leu Leu Leu Ala Gly Gly Ala Ile Leu Ala Leu
385                 390                 395                 400
Thr Phe Val Pro Leu Asp Leu Gln Thr Val Arg Thr Val Leu Ala Val
                405                 410                 415
Phe Gly Lys Gly Cys Leu Ser Ser Phe Ser Cys Leu Phe Leu Tyr
            420                 425                 430
Thr Ser Glu Leu Tyr Pro Thr Val Ile Arg Gln Thr Gly Met Gly Val
        435                 440                 445
Ser Asn Leu Trp Thr Arg Val Gly Ser Met Val Ser Pro Leu Val Lys
    450                 455                 460
```

-continued

```
Ile Thr Gly Glu Val Gln Pro Phe Ile Pro Asn Ile Ile Tyr Gly Ile
465                 470                 475                 480

Thr Ala Leu Leu Gly Gly Ser Ala Ala Leu Phe Leu Pro Glu Thr Leu
            485                 490                 495

Asn Gln Pro Leu Pro Glu Thr Ile Glu Asp Leu Glu Asn Trp Ser Leu
        500                 505                 510

Arg Ala Lys Lys Pro Lys Gln Glu Pro Glu Val Glu Lys Ala Ser Gln
    515                 520                 525

Arg Ile Pro Leu Gln Pro His Gly Pro Gly Leu Gly Ser Ser
530                 535                 540
```

<210> SEQ ID NO 11
<211> LENGTH: 554
<212> TYPE: PRT
<213> ORGANISM: Homo sapiens

<400> SEQUENCE: 11

```
Met Ala Phe Gln Asp Leu Leu Gly His Ala Gly Asp Leu Trp Arg Phe
1               5                   10                  15

Gln Ile Leu Gln Thr Val Phe Leu Ser Ile Phe Ala Val Ala Thr Tyr
            20                  25                  30

Leu His Phe Met Leu Glu Asn Phe Thr Ala Phe Ile Pro Gly His Arg
        35                  40                  45

Cys Trp Val His Ile Leu Asp Asn Asp Thr Val Ser Asp Asn Asp Thr
    50                  55                  60

Gly Ala Leu Ser Gln Asp Ala Leu Leu Arg Ile Ser Ile Pro Leu Asp
65                  70                  75                  80

Ser Asn Met Arg Pro Glu Lys Cys Arg Arg Phe Val His Pro Gln Trp
                85                  90                  95

Gln Leu Leu His Leu Asn Gly Thr Phe Pro Asn Thr Ser Asp Ala Asp
            100                 105                 110

Met Glu Pro Cys Val Asp Gly Trp Val Tyr Asp Arg Ile Ser Phe Ser
        115                 120                 125

Ser Thr Ile Gly Asp Leu Lys Trp Asp Leu Val Cys Asp Ser Gln Ser
    130                 135                 140

Leu Thr Ser Val Ala Lys Phe Val Phe Met Ala Gly Met Met Leu Gly
145                 150                 155                 160

Gly Ile Leu Gly Val His Leu Ser Asp Arg Phe Gly Arg Ser Phe Val
                165                 170                 175

Leu Arg Trp Cys Tyr Leu Gln Val Ala Ile Val Gly Thr Cys Ala Ala
            180                 185                 190

Leu Ala Pro Thr Phe Leu Ile Tyr Cys Ser Val Arg Phe Leu Ser Gly
        195                 200                 205

Ile Ala Ala Met Ser Phe Ile Thr Asn Thr Ile Met Leu Ile Ala Glu
    210                 215                 220

Trp Ala Thr His Arg Phe Gln Ala Met Gly Ile Thr Leu Gly Met Cys
225                 230                 235                 240

Pro Ser Gly Ile Ala Phe Met Thr Leu Ala Gly Leu Ala Phe Ala Ile
                245                 250                 255

Arg Asp Trp His Ile Leu Gln Leu Val Val Ser Val Pro Tyr Phe Val
            260                 265                 270

Ile Phe Leu Thr Ser Ser Trp Leu Leu Glu Ser Ala Arg Trp Leu Ile
        275                 280                 285

Ile Asn Asn Lys Pro Glu Glu Gly Leu Lys Glu Leu Arg Lys Ala Ala
    290                 295                 300
```

-continued

```
His Arg Ser Gly Met Lys Asn Ala Arg Asp Thr Leu Thr Leu Glu Ile
305                 310                 315                 320

Leu Lys Ser Thr Met Lys Lys Glu Leu Glu Ala Ala Gln Lys Lys Lys
            325                 330                 335

Pro Ser Leu Cys Glu Met Leu His Met Pro Asn Ile Cys Lys Arg Ile
        340                 345                 350

Ser Leu Leu Ser Phe Thr Arg Phe Ala Asn Phe Met Ala Tyr Phe Gly
    355                 360                 365

Leu Asn Leu His Val Gln His Leu Gly Asn Asn Val Phe Leu Leu Gln
370                 375                 380

Thr Leu Phe Gly Ala Val Ile Leu Leu Ala Asn Cys Val Ala Pro Trp
385                 390                 395                 400

Ala Leu Lys Tyr Met Asn Arg Arg Ala Ser Gln Met Leu Leu Met Phe
                405                 410                 415

Leu Leu Ala Ile Cys Leu Leu Ala Ile Ile Phe Val Pro Gln Glu Met
            420                 425                 430

Gln Thr Leu Arg Glu Val Leu Ala Thr Leu Gly Leu Gly Ala Ser Ala
        435                 440                 445

Leu Ala Asn Thr Leu Ala Phe Ala His Gly Asn Glu Val Ile Pro Thr
    450                 455                 460

Ile Ile Arg Ala Arg Ala Met Gly Ile Asn Ala Thr Phe Ala Asn Ile
465                 470                 475                 480

Ala Gly Ala Leu Ala Pro Leu Met Met Ile Leu Ser Val Tyr Ser Pro
                485                 490                 495

Pro Leu Pro Trp Ile Ile Tyr Gly Val Phe Pro Phe Ile Ser Gly Phe
            500                 505                 510

Ala Phe Leu Leu Leu Pro Glu Thr Arg Asn Lys Pro Leu Phe Asp Thr
        515                 520                 525

Ile Gln Asp Glu Lys Asn Glu Arg Lys Asp Pro Arg Glu Pro Lys Gln
    530                 535                 540

Glu Asp Pro Arg Val Glu Val Thr Gln Phe
545                 550

<210> SEQ ID NO 12
<211> LENGTH: 541
<212> TYPE: PRT
<213> ORGANISM: Homo sapiens

<400> SEQUENCE: 12

Met Ala Phe Glu Glu Leu Leu Ser Gln Val Gly Gly Leu Gly Arg Phe
1               5                   10                  15

Gln Met Leu His Leu Val Phe Ile Leu Pro Ser Leu Met Leu Leu Ile
            20                  25                  30

Pro His Ile Leu Leu Glu Asn Phe Ala Ala Ala Ile Pro Gly His Arg
        35                  40                  45

Cys Trp Val His Met Leu Asp Asn Asn Thr Gly Ser Gly Asn Glu Thr
    50                  55                  60

Gly Ile Leu Ser Glu Asp Ala Leu Leu Arg Ile Ser Ile Pro Leu Asp
65                  70                  75                  80

Ser Asn Leu Arg Pro Glu Lys Cys Arg Arg Phe Val His Pro Gln Trp
                85                  90                  95

Gln Leu Leu His Leu Asn Gly Thr Ile His Ser Thr Ser Glu Ala Asp
            100                 105                 110

Thr Glu Pro Cys Val Asp Gly Trp Val Tyr Asp Gln Ser Tyr Phe Pro
```

```
              115                 120                 125
Ser Thr Ile Val Thr Lys Trp Asp Leu Val Cys Asp Tyr Gln Ser Leu
    130                 135                 140

Lys Ser Val Val Gln Phe Leu Leu Thr Gly Met Leu Val Gly Gly
145                 150                 155                 160

Ile Ile Gly Gly His Val Ser Asp Arg Phe Gly Arg Phe Ile Leu
                165                 170                 175

Arg Trp Cys Leu Leu Gln Leu Ala Ile Thr Asp Thr Cys Ala Ala Phe
            180                 185                 190

Ala Pro Thr Phe Pro Val Tyr Cys Val Leu Arg Phe Leu Ala Gly Phe
            195                 200                 205

Ser Ser Met Ile Ile Ser Asn Asn Ser Leu Pro Ile Thr Glu Trp
    210                 215                 220

Ile Arg Pro Asn Ser Lys Ala Leu Val Val Ile Leu Ser Ser Gly Ala
225                 230                 235                 240

Leu Ser Ile Gly Gln Ile Ile Leu Gly Gly Leu Ala Tyr Val Phe Arg
                245                 250                 255

Asp Trp Gln Thr Leu His Val Val Ala Ser Val Pro Phe Leu Gly Leu
            260                 265                 270

Leu Leu Leu Gln Arg Trp Leu Val Glu Ser Ala Arg Trp Leu Ile Ile
        275                 280                 285

Thr Asn Lys Leu Asp Glu Gly Leu Lys Ala Leu Arg Lys Val Ala Arg
290                 295                 300

Thr Asn Gly Ile Lys Asn Ala Glu Glu Thr Leu Asn Ile Glu Val Val
305                 310                 315                 320

Arg Ser Thr Met Gln Glu Glu Leu Asp Ala Ala Gln Thr Lys Thr Thr
                325                 330                 335

Val Cys Asp Leu Phe Arg Asn Pro Ser Met Arg Lys Arg Ile Cys Ile
            340                 345                 350

Leu Val Phe Leu Arg Phe Ala Asn Thr Ile Pro Phe Tyr Gly Thr Met
            355                 360                 365

Val Asn Leu Gln His Val Gly Ser Asn Ile Phe Leu Leu Gln Val Leu
    370                 375                 380

Tyr Gly Ala Val Ala Leu Ile Val Arg Cys Leu Ala Leu Leu Thr Leu
385                 390                 395                 400

Asn His Met Gly Arg Arg Ile Ser Gln Ile Leu Phe Met Phe Leu Val
                405                 410                 415

Gly Leu Ser Ile Leu Ala Asn Thr Phe Val Pro Lys Glu Met Gln Thr
            420                 425                 430

Leu Arg Val Ala Leu Ala Cys Leu Gly Ile Gly Cys Ser Ala Ala Thr
            435                 440                 445

Phe Ser Ser Val Ala Val His Phe Ile Glu Leu Ile Pro Thr Val Leu
    450                 455                 460

Arg Ala Arg Ala Ser Gly Ile Asp Leu Thr Ala Ser Arg Ile Gly Ala
465                 470                 475                 480

Ala Leu Ala Pro Leu Leu Met Thr Leu Thr Val Phe Phe Thr Thr Leu
                485                 490                 495

Pro Trp Ile Ile Tyr Gly Ile Phe Pro Ile Ile Gly Gly Leu Ile Val
            500                 505                 510

Phe Leu Leu Pro Glu Thr Lys Asn Leu Pro Leu Pro Asp Thr Ile Lys
        515                 520                 525

Asp Val Glu Asn Gln Lys Lys Asn Leu Lys Glu Lys Ala
```

What is claimed is:

1. An isolated, enriched, or purified nucleic acid molecule comprising a nucleic acid molecule of SEQ ID NO:2.
2. The isolated, enriched, or purified nucleic acid molecule of claim 1, wherein said nucleic acid molecule is SEQ ID NO:2.
3. An isolated, enriched, or purified nucleic acid molecule comprising a nucleic acid molecule which encodes a human OAT polypeptide comprising SEQ ID NO:8.
4. An isolated, enriched, or purified nucleic acid molecule which is complementary to any of the nucleic acid molecules of claim 1 or 3.
5. The nucleic acid molecule of claim 1 or 3, further comprising a vector or promoter effective to initiate transcription in a host cell.
6. The nucleic acid molecule of claim 5, wherein said promoter comprises an inducible promoter.
7. The isolated, enriched, or purified nucleic acid molecule of claim 3, wherein said nucleic acid molecule encodes a polypeptide that is SEQ ID NO:8.
8. An amphibian oocyte containing a nucleic acid molecule encoding for a human OAT polypeptide according to claim 3.
9. The amphibian oocyte of claim 8 that is a *Xenopus laevis* oocyte.
10. An isolated nucleic acid molecule comprising a nucleotide sequence that has at least 83% identity to nucleotide sequence contained in SEQ ID NO:2, wherein the percent identity is calculated using the GAP-Alignment program in the GCG software package, using a gap weight of 5.0 and a length weight of 0.3 wherein said nucleotide sequence encodes a polypeptide having OAT activity.
11. An isolated nucleic acid molecule of claim 10 wherein said nucleic acid molecule hybridizes to a nucleic acid molecule comprising the nucleic acid sequence of SEQ ID NO:2 under highly stringent conditions as follows: hybridization in 50% formamide, 5×SSC, 50 mM $NaH_3PO_4$, pH 6.8, 0.5% SDS, 0.1 mg/mL sonicated salmon sperm DNA, and 5×Denhardt's solution at 42° C. overnight; washing with 2×SSC, 0.1% SDS at 45° C.; and washing with 0.2×SSC, 0.1% SDS at 45° C.
12. A nucleic acid probe for the detection, isolation, purification, enrichment, or amplification of a nucleic acid molecule encoding human OAT in a sample, wherein said nucleic acid probe is SEQ ID NO:2 from nucleotide 1370–1638.
13. A recombinant cell comprising a nucleic acid molecule encoding a human OAT polypeptide wherein said nucleic acid molecule is SEQ ID NO:2.
14. The cell of claim 13, wherein said cell is stably transformed.
15. The cell of claim 13 or 14, wherein said cell is a mammalian cell.
16. The cell of claim 13 or 14, wherein said nucleic acid is expressed from an inducible promoter.
17. The cell of claim 16, wherein said promoter is inducible with ecdysone.
18. The cell of claim 13 or 14, wherein said cell is a yeast cell.
19. The cell of claim 13 or 14, wherein said cell is an insect cell.
20. A method of preparing an hOAT polypeptide comprising:
    culturing the recombinant cell of claim 14 under conditions that permit expression of the hOAT polypeptide; and isolating said polypeptide.

* * * * *